US 8,486,913 B2
Jul. 16, 2013

(12) United States Patent
Croce et al.

(10) Patent No.: US 8,486,913 B2
(45) Date of Patent: Jul. 16, 2013

(54) MICRORNA FINGERPRINTS DURING HUMAN MEGAKARYOCYTOPOIESIS

(75) Inventors: Carlo M. Croce, Columbus, OH (US);
Ramiro Garzon, Columbus, OH (US);
George A. Calin, Pearland, TX (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 13/595,204

(22) Filed: Aug. 27, 2012

(65) Prior Publication Data
US 2012/0322859 A1   Dec. 20, 2012

Related U.S. Application Data

(62) Division of application No. 13/169,184, filed on Jun. 27, 2011, which is a division of application No. 12/293,471, filed as application No. PCT/US2007/006824 on Mar. 19, 2007, now Pat. No. 7,985,584.

(60) Provisional application No. 60/743,585, filed on Mar. 20, 2006.

(51) Int. Cl.
*A61K 48/00* (2006.01)

(52) U.S. Cl.
USPC ......... 514/44; 536/24.5; 536/24.31; 536/24.1

(58) Field of Classification Search
None
See application file for complete search history.

(56) References Cited

U.S. PATENT DOCUMENTS

| 7,888,010 B2 | 2/2011 | Brown et al. |
| 7,919,245 B2 | 4/2011 | Brown et al. |
| 2007/0092882 A1 | 4/2007 | Wang et al. |
| 2007/0213292 A1 | 9/2007 | Stoffel et al. |
| 2009/0131356 A1 | 5/2009 | Bader et al. |
| 2010/0099200 A1 | 4/2010 | Nazabal et al. |
| 2010/0104662 A1 | 4/2010 | Oren et al. |
| 2010/0196426 A1 | 8/2010 | Skog et al. |

FOREIGN PATENT DOCUMENTS

| CA | 2533701 A1 | 2/2005 |
| FR | 2877350 A1 | 11/2004 |
| WO | 2005013901 A3 | 2/2005 |
| WO | 2005079397 A2 | 9/2005 |
| WO | 2005103298 A2 | 11/2005 |
| WO | 2007016548 A2 | 2/2007 |
| WO | 2007112754 A2 | 10/2007 |
| WO | 2008/029295 A2 | 3/2008 |
| WO | 2008/036168 A2 | 3/2008 |
| WO | 2008073915 A2 | 6/2008 |

OTHER PUBLICATIONS

Grier et al. (Journal of Pathology 2005, vol. 205: 154-171).*
Hudlebusch et al. (Leukemia & Lymphoma 2004, vol. 45: 1215-1217).*

EP Search Report, Application No. 12165636.7 dated Jun. 8, 2012.
EP Search Report, Application No. 12165638.3 dated Jun. 12, 2012.
Australian Government, Examiner's First Report, Appln. No. 2007243475, Dated Mar. 30, 2012.
Australian Office Action, Application No. 2006291165 dated Feb. 13, 2012.
Australian Office Action, Application No. 2007227423 dated Apr. 13, 2012.
Australian Office Action, Application No. 2007205234 dated Sep. 20, 2011.
Australian Office Action, Application No. 2006291165 dated Aug. 23, 2011.
Australian Office Action, Application No. 2008248319 dated Jul. 12, 2012.
Australian Office Action, Application No. 2007314212 dated Aug. 28, 2012.
Australian Office Action, Application No. 2007272947 dated May 21, 2012.
Australian Office Action, Application No. 2008266014 dated Jul. 6, 2012.
Australian Office Action, Application No. 2007205257 dated Dec. 22, 2011.
Australian Office Action, Application No. 2007205257 dated Jul. 16, 2012.
Australian Office Action, Application No. 2007346101 dated Jun. 21, 2012.
Canadian Office Action, Application No. 2,617,581, dated Apr. 2, 2012.
Canadian Office Action, Application No. 2,635,616, dated Feb. 27, 20112.
Chinese Office Action, Application No. 200780033066.9 dated Jun. 26, 2012.
Chinese Office Action, Application No. 200880112585.9 dated May 24, 2012.
Chinese Office Action, Application No. 20088011920639 dated May 3, 2012.
Chinese Office Action, Application No. 200880116343.7 dated Jan. 31, 2011.
Chinese Office Action, Application No. 200880108625.2 dated Aug. 21, 2012.
Chinese Office Action, Application No. 200680039776.8 dated Jun. 30, 2011.
Communication Concerning Office Action Received from Japanese Patent Office dated Jan. 30, 2012, Japanese Patent Application No. 2008-531200.
EP Search Report, Application No. 12165734.0 dated Aug. 27, 2012.
EP Search Report, Application No. 11196261.9 dated Feb. 28, 2012.
EP Search Report, Application No. 12165740.7 dated Aug. 27, 2012.
EP Search Report, Application No. 09830750.7 dated Aug. 27, 2012.
EP Search Report, Application No. 09715356.3 dated Jul. 12, 2012.
EP Search Report, Application No. 11196190.0 dated Apr. 24, 2012.
EP Search Report, Application No. 11196256.9 dated Feb. 28, 2012.
EP Search Report, Application No. 11196250.2 dated Apr. 24, 2012.
EP Search Report, Application No. 11196253.6 dated Apr. 24, 2012.

(Continued)

*Primary Examiner* — Kimberly Chong
(74) *Attorney, Agent, or Firm* — MacMillan, Sobanski & Todd, LLC

(57) ABSTRACT

Described herein is a method of decreasing expression of HOXA1 in a subject having a cancer and/or myeloproliferative disorder associated with overexpression of a HOXA1 gene product where an effective amount of at least one miR-10a gene product or an isolated variant or biologically-active fragment thereof is administered to the subject sufficient to decrease expression of the HOXA1 gene product in the subject.

7 Claims, 17 Drawing Sheets
(11 of 17 Drawing Sheet(s) Filed in Color)

OTHER PUBLICATIONS

EP Search Report, Application No. 11196262.7 dated Feb. 28, 2012.
EP Search Report, Application No. 12154298.9 dated Jun. 4, 2012.
EP Search Report, Application No. 11196264-3 dated Feb. 28, 2012.
EP Search Report, Application No. 11196254.4 dated Feb. 28, 2012.
EP Search Report, Application No. 12154304.5 dated Jun. 26, 2012.
EP Search Report, Application No. 12154342.5 dated Jul. 6, 2012.
EP Search Report, Application No. 12154321.9 dated Jul. 20, 2012.
EP Search Report, Application No. 11196265.0 dated Mar. 5, 2012.
European Communication Pursuant to Article 94(3) EPC, Application No. 08799295.4, dated Nov. 18, 2011.
European Communication Pursuant to Article 94(3) EPC, Application No. 08767439.6, dated Feb. 12, 2011.
European Communication Pursuant to Article 94(3)EPC, Application No. 06814375.9 dated Oct. 14, 2011.
European Communication Pursuant to Article 94(3) EPC, Application No. 06800599.0 dated Nov. 25, 2011.
European Communication Pursuant to Article 94(3) EPC, Application No. 07867402.5, dated Apr. 10, 2012.
European Communication Pursuant to Article 94(3) EPC, Application No. 07717903.4, dated Apr. 25, 2012.
European Communication Pursuant to Article 94(3) EPC, Application No. 07716208.9, dated Sep. 13, 2011.
European Communication Pursuant to Article 94(3) EPC, Application No. 08841700.1, dated Jun. 1, 2012.
European Seach Report, Application No. 09714868.8 dated Aug. 1, 2011.
European Search Report, Application No. 09713926.5 dated Jul. 21, 2011.
European Search Report, Application No. 08713330.2, dated Jul. 22, 2011.
European Search Report, Application No. 08770974.4, dated Oct. 21, 2011.
Japanese Office Action dated Feb. 24, 2012, Japanese Patent Application No. 2008-549532.
Japanese Office Action dated Feb. 22, 2012, Japanese Patent Application No. 2008-549549.
Japanese Office Action dated Jan. 4, 2012, Japanese Patent Application No. 2008-5251070.
Japanese Office Action dated Feb. 24, 2012, Japanese Patent Application No. 2008-549555.
PCT International Preliminary Report on Patentability, PCT/US2010/057758 filed Nov. 23, 2010, dated Jun. 7, 2012.
PCT International Preliminary Report on Patentability, PCT/US2010/025173 filed Feb. 24, 2010, dated Sep. 9, 2011.
PCT International Search Report and the Written Opinion, PCT/US2012/020911 filed Jan. 11, 2012, dated Apr. 25, 2012.
PCT International Search Report and the Written Opinion, PCT/US2012/28016 filed Mar. 7, 2012, dated Aug. 3, 2012.
PCT Invitation to Pay Additional Fees, PCT/US2012/028016 filed Mar. 7, 2012, dated May 29, 2012.
Aiba, M. "Pathology of the Breast Carcinoma from the Viewpoint of the Proliferative Activity and Grade of Malignancy," JP J Cancer Clin, 2000, pp. 475-181, vol. 46, No. 5.
Braun et al., "p53-Responsive MicroRNAs 192 and 215 are Capable of Inducing Cell Cycle Arrest," Cancer Research, 2008, pp. 10094-10104, vol. 68.
Butz, H. et al., "Down-Regulation of Wee1 Kinase by a Specific Subset of MicroRNA Sporadic Pituitary Adenomas," Journal of Clinical Endocrinol Metab, Oct. 2010, pp. E181-E191, vol. 95, No. 10.
Dahiya, N. et al., "MicroRNA Expression and Identification of Putative miRNA Targets in Ovarian Cancer," Plos One, Jan. 2008, pp. 1-11, vol. 3, No. 6.
Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.
Eiriksdottir, G. et al., "Mapping Loss of Heterozygosity at Chromosome 13q: Loss at 13q12-q13 is Associated wit Breast Tumour Progression and Poor Prognosis," European Journal of Cancer, 1998, pp. 2076-2081, vol. 34, No. 13.
Fujuta, S. et al., "miR-21 Gene Expression Triggered by AP-1 is Sustained Through a Double-Negative Feedback Mechanism," J. Mol. Biol., Abstract, 2008, pp. 492-504, vol. 378.
Gailiun, M., "Single MicroRNA Causes Cancer in Transgenic Mice," Research Communications, The Ohio State University, Apr. 2006.
Garofalo, M. et al., "MicroRNA Signatures of TRAIL Resistance in Human Non-Small Cell Lung Cancer," Oncogene, 2007, pp. 3854-3855, vol. 27.
Jazbutyte, V. et al., "MicroNRA-21: From Cancer to Cardiovascular Disease," Current Drug Targets, Abstract, 2010, pp. 926-935, vol. 11.
Lawrie, C. H. "MicroRNAs and Haematology: Small Molecules, Big Function," British Journal of Haematology, Jun. 2007, pp. 503-512, vol. 137, No. 6.
Lawrie, C.H., "MicroRNA, Expression in Lymphoma," Expert Opinoin on Biological Therapy, Sep. 2007, pp. 1363-1374, vol. 7, No. 9.
Lee, Y.S. et al., "MicroRNAs: Small but Potent Onogenes or Tumor Suppressors," Current Opinion in Investigational Drugs, Jun. 2006, pp. 560-564, vol. 7, No. 6.
Li, Z. et al., "Inhibition of PRL-3 Gene Expression in Gastric Cancer Cell Line SGC7901 via MicroRNA Suppressed Reduces Peritoneal Metastasis," Biochemical and Biophysical Research, Sep. 2006, pp. 229-237, vol. 348, No. 1.
Martin, M. et al., "MicroRNA-155 Regulates Human Angiotensin II Type 1 Receptor Expression in Fibroblasts," The Journal of Biological Chemistry, Jul. 2006, pp. 18277-18284, vol. 281, No. 27.
Mazurek, N. et al., "Phosphorylated Galectin-3 Mediates Tumor Necrosis Factor-Related Apoptosis-Inducing Ligand Signaling by Regulating Phosphatase and Tensin Homologue Deleted on Chromosome 10 in Human Breast Carcinoma Cells," The Journal of Biological Chemistry, Jul. 2007, pp. 21337-21348, vol. 282, No. 29.
Nakajima, G. et al., "Non-Coding MicroRNAs HAS-LET-7G and HAS-MIR-181b are Associated with Chemoresponse to S-1 in Colon Cancer," Cancer Genomics & Proteomics, Sep. 2006, pp. 317-324, vol. 3, No. 5.
O'Connell, R. et al., "Inositol Phosphatase SHIP1 is a Primary Target of miR-155," PNAS, Apr. 2009, pp. 7113-7118, vol. 106, No. 17.
Okada, H. et al., "MicroRNAs in Immune Regulation—Opportunities for Cancer Immunotherapy," The International Journal of Biochemistry & Cell Biology, 2010, pp. 1256-1261, vol. 42.
Partha, D. et al., "Early Detection of Ovarian Cancer," NIH Public Access Author Manuscript, Jun. 2008, pp. 1-17, Retrieved from the Internet.
Petrocca, F. et al., "MicroRNAs Deregulation in Gastric Cancer," PNAS, Apr. 2006, p. 1338, vol. 47, Abstract # 5690.
Pichiorri et al., "Downregulation of p53-Inducible MicroRNAs 192, 194 and 215 Impairs the p53/MDM2 Autoregulatory Loop in Multiple Myeloma Development," Cancer Cell, 2010, pp. 367-381, vol. 18.
Ribas, J. et al., "The Transcriptional Regulation of miR-21, Its Multiple Transcripts, and Their Implication in Prostate Cancer," Cell Cycle, 2010, pp. 923-929, vol. 9.
Rossi, S. et al., "MicroRNA Fingerprinting of CLL Patients with Chromosome 17p Deletion Identify a miR-21 Score that Stratifies Early Survival," Blood, Aug. 2010, pp. 945-952, vol. 116, No. 6.
Ryu, J.K. et al., "Aberrant MicroRNA-155 Expression is an Early Event in the Multistep Progression of Pancreatic Adenocarcinoma," Pancreatology, 2010, pp. 66-73, vol. 10.
Shih, K.K. et al., "Exosomal MicroRNAs Step into the Biomarker Arena," Gynecologic Oncology, Jul. 2008, pp. 1-2, vol. 110, No. 1.
Stamatopoulos, B. et al., "MicroRNA-29c and MicroRNA-233 Down-Regulation has In Vivo Significance in Chronic Lymphocytic Leukemia and Improves Disease Risk Stratification," Blood, May 2009, pp. 5237-5245, vol. 113, No. 21.
Thomson, M., Supplementary data for "A Custon Microarray Platform for Analysis of MicroRNA Gene Expression," Nature Methods, Oct. 2004, pp. 47-53, vol. 1, No. 1.
Vassilev et al., "In Vivo Activation of the p53 Pathway by Small-Molecule Antagonists of MDM2," Science, 2004, pp. 844-848, vol. 303.

Watson, D.I. et al., "MicroRNA Expression Profiles in Barrett's Oesophagus," RACS Annual Scientific Congress, 2007, pp. A45, vol. 77.

Wiemer et al., "The Role of MicroRNAs in Cancer: No Small Matter," European Journal of Cancer, Jun. 12, 2007, vol. 43, No. 10, pp. 1529-1544.

Williams, C.S., "OncomiRs: The Discovery and Progress of MicroRNAs in Cancers," Molecular Cancer, Sep. 2007, pp. 259-269, vol. 6, No. 4.

Xi, Y. et al., "Prognostic Values of MicroRNAs in Colorectal Cancer," Biomarker Insights, Jan. 2006, pp. 113-121, vol. 1.

Zhao et al., "p53 Mediates the Negative Regulation of MDM2 by Orphan Receptor TR3," The EMBO Journal, 2006, pp. 5703-5715, vol. 25.

* cited by examiner

HOX A1 GENE EXPRESSION

```
                          SEQUENCE LISTING

<160> NUMBER OF SEQ ID NOS: 507

<210> SEQ ID NO 1
<211> LENGTH: 90
<212> TYPE: RNA
<213> ORGANISM: Homo sapiens

<400> SEQUENCE: 1
cacuguggga ugagguagua gguuguauag uuuuaggguc acacccacca cugggagaua      60
acuauacaau cuacugucuu uccuaacgug                                      90

<210> SEQ ID NO 2
<211> LENGTH: 72
<212> TYPE: RNA
<213> ORGANISM: Homo sapiens

<400> SEQUENCE: 2
agguugaggu aguagguugu auaguuuaga auuacaucaa gggagauaac uguacagccu      60
ccuagcuuuc cu                                                         72

<210> SEQ ID NO 3
<211> LENGTH: 74
<212> TYPE: RNA
<213> ORGANISM: Homo sapiens

<400> SEQUENCE: 3
gggugaggua guagguugua uaguuugggg cucugcccug cuaugggaua acuauacaau      60
cuacugucuu uccu                                                       74

<210> SEQ ID NO 4
<211> LENGTH: 107
<212> TYPE: RNA
<213> ORGANISM: Homo sapiens

<400> SEQUENCE: 4
gugacugcau gcucccaggu ugagguagua gguuguauag uuuagaauua cacaagggag      60
auaacuguac agccuccuag cuuuccuugg ucuugcacu aaacaac                    107

<210> SEQ ID NO 5
<211> LENGTH: 85
<212> TYPE: RNA
<213> ORGANISM: Homo sapiens

<400> SEQUENCE: 5
ggcggggugu gguaguaggu ugugugguuu cagggcagug auguugcccc ucggaagaua      60
acuauacaac cuacugccuu cccug                                           85

<210> SEQ ID NO 6
<211> LENGTH: 84
<212> TYPE: RNA
```

```
<213> ORGANISM: Homo sapiens

<400> SEQUENCE: 6
gcauccgggu ugagguagua gguuguaugg uuuagaguua cacccuggga guuaacugua    60
caaccuucua gcuuccuug gagc                                            84

<210> SEQ ID NO 7
<211> LENGTH: 87
<212> TYPE: RNA
<213> ORGANISM: Homo sapiens

<400> SEQUENCE: 7
ccuaggaaga gguaguaggu ugcauaguuu uagggcaggg auuuugccca caaggaggua    60
acuauacgac cugcugccuu ucuuagg                                        87

<210> SEQ ID NO 8
<211> LENGTH: 85
<212> TYPE: RNA
<213> ORGANISM: Homo sapiens

<400> SEQUENCE: 8
cuaggaagag guaguaguuu gcauaguuuu agggcaaaga uuuugcccac aaguaguuag    60
cuauacgacc ugcagccuuu uguag                                          85

<210> SEQ ID NO 9
<211> LENGTH: 85
<212> TYPE: RNA
<213> ORGANISM: Homo sapiens

<400> SEQUENCE: 9
cuggcugagg uaguaguuug ugcuguuggu cggguuguga cauugcccgc uguggagaua    60
acugcgcaag cuacugccuu gcuag                                          85

<210> SEQ ID NO 10
<211> LENGTH: 79
<212> TYPE: RNA
<213> ORGANISM: Homo sapiens

<400> SEQUENCE: 10
cccgggcuga gguaggaggu uguauaguug aggaggacac ccaaggagau cacuauacgg    60
ccuccuagcu uuccccagg                                                 79

<210> SEQ ID NO 11
<211> LENGTH: 87
<212> TYPE: RNA
<213> ORGANISM: Homo sapiens

<400> SEQUENCE: 11
ucagagugag guaguagauu guauaguugu ggguaguga uuuuacccug uucaggagau     60
aacuauacaa ucuauugccu ucccuga                                        87

<210> SEQ ID NO 12
<211> LENGTH: 89
<212> TYPE: RNA
<213> ORGANISM: Homo sapiens

<400> SEQUENCE: 12
cugugggaug agguaguaga uuguauaguu gugggguagu gauuuacccc uguucaggag    60
auaacuauac aaucuauugc cuucccuga                                      89
```

```
<210> SEQ ID NO 13
<211> LENGTH: 85
<212> TYPE: RNA
<213> ORGANISM: Homo sapiens

<400> SEQUENCE: 13
cugugggaug agguaguaga uuguauaguu uuagggucau accccaucuu ggagauaacu    60
auacagucua cugucuuucc cacgg                                         85

<210> SEQ ID NO 14
<211> LENGTH: 108
<212> TYPE: RNA
<213> ORGANISM: Homo sapiens

<400> SEQUENCE: 14
uugccugauu ccaggcugag guaguaguuu guacaguuug agggucuaug auaccacccg    60
guacaggaga uaacuguaca ggccacugcc uugccaggaa cagcgcgc                108

<210> SEQ ID NO 15
<211> LENGTH: 85
<212> TYPE: RNA
<213> ORGANISM: Homo sapiens

<400> SEQUENCE: 15
cuggcugagg uaguaguuug ugcuguuggu cgggumguga cauugcccgc uguggagaua    60
acugcgcaag cuacugccuu gcuag                                         85

<210> SEQ ID NO 16
<211> LENGTH: 85
<212> TYPE: RNA
<213> ORGANISM: Homo sapiens

<400> SEQUENCE: 16
accuacucag aguacauacu ucuuuaugua cccauaugaa cauacaaugc uauggaaugu    60
aaagaaguau guauuuuugg uaggc                                         85

<210> SEQ ID NO 17
<211> LENGTH: 108
<212> TYPE: RNA
<213> ORGANISM: Homo sapiens

<400> SEQUENCE: 17
cagcuaacaa cuuaguaaua ccuacucaga guacauacuu cuuuauguac ccauaugaac    60
auacaaugcu auggaaugua aagaaguaug uauuuuggu aggcaaua                 108

<210> SEQ ID NO 18
<211> LENGTH: 85
<212> TYPE: RNA
<213> ORGANISM: Homo sapiens

<400> SEQUENCE: 18
gccugcuugg gaaacauacu ucuuuauaug cccauaugga ccugcuaagc uauggaaugu    60
aaagaaguau guaucucagg ccggg                                         85

<210> SEQ ID NO 19
<211> LENGTH: 71
<212> TYPE: RNA
<213> ORGANISM: Homo sapiens

<400> SEQUENCE: 19
```

```
ugggaaacau acuucuuuau augcccauau ggaccugcua agcuauggaa uguaaagaag    60
uauguaucuc a                                                         71

<210> SEQ ID NO 20
<211> LENGTH: 85
<212> TYPE: RNA
<213> ORGANISM: Homo sapiens

<400> SEQUENCE: 20
accuacucag aguacauacu ucuuuaugua cccauaugaa cauacaaugc uauggaaugu    60
aaagaaguau guauuuuugg uaggc                                          85

<210> SEQ ID NO 21
<211> LENGTH: 108
<212> TYPE: RNA
<213> ORGANISM: Homo sapiens

<400> SEQUENCE: 21
uggauguugg ccaguucug uguggaagac uagugauuuu guuguuuuua gauaacuaaa     60
ucgacaacaa aucacagucu gccauauggc acaggccaug ccucuaca               108

<210> SEQ ID NO 22
<211> LENGTH: 110
<212> TYPE: RNA
<213> ORGANISM: Homo sapiens

<400> SEQUENCE: 22
uuggauguug gccaguucu guguggaaga cuagugauuu uguuguuuuu agauaacuaa     60
aucgacaaca aaucacaguc ugccauaugg cacaggccau gccucuacag             110

<210> SEQ ID NO 23
<211> LENGTH: 110
<212> TYPE: RNA
<213> ORGANISM: Homo sapiens

<400> SEQUENCE: 23
cuggauacag aguggaccgg cuggccccau cuggaagacu agugauuuug uuguugucuu    60
acugcgcuca acaacaaauc ccagucuacc uaauggugcc agccaucgca             110

<210> SEQ ID NO 24
<211> LENGTH: 110
<212> TYPE: RNA
<213> ORGANISM: Homo sapiens

<400> SEQUENCE: 24
agauuagagu ggcuguggguc uagugcugug uggaagacua gugauuuugu uguucugaug   60
uacuacgaca acaagucaca gccggccuca uagcgcagac ucccuucgac             110

<210> SEQ ID NO 25
<211> LENGTH: 89
<212> TYPE: RNA
<213> ORGANISM: Homo sapiens

<400> SEQUENCE: 25 cggggguuggu uguuaucuuu gguuaucuag cuguaugagu ggguggagu cuucauaaag    60 cuagauaacc gaaaguaaaa auaaccccca                                     89

<210> SEQ ID NO 26
<211> LENGTH: 87
<212> TYPE: RNA
```

```
<213> ORGANISM: Homo sapiens

<400> SEQUENCE: 26
ggaagcgagu uguuaucuuu gguuaucuag cuguaugagu guauuggucu ucauaaagcu    60
agauaaccga aaguaaaaac uccuuca                                       87

<210> SEQ ID NO 27
<211> LENGTH: 90
<212> TYPE: RNA
<213> ORGANISM: Homo sapiens

<400> SEQUENCE: 27
ggaggcccgu uucucucuuu gguuaucuag cuguaugagu gccacagagc cgucauaaag    60
cuagauaacc gaaaguagaa augauucuca                                    90

<210> SEQ ID NO 28
<211> LENGTH: 110
<212> TYPE: RNA
<213> ORGANISM: Homo sapiens

<400> SEQUENCE: 28
gaucugucug ucuucuguau auacccugua gauccgaauu uguguaagga auuuguggu     60 cacaaauucg uaucuagggg aauauguagu ugacauaaac acuccgcucu              110

<210> SEQ ID NO 29
<211> LENGTH: 110
<212> TYPE: RNA
<213> ORGANISM: Homo sapiens

<400> SEQUENCE: 29
ccagagguug uaacguuguc uauauauacc cuguagaacc gaauugugu gguauccgua     60 uagucacaga uucgauucua ggggaauaua uggucgaugc aaaaacuuca              110

<210> SEQ ID NO 30
<211> LENGTH: 108
<212> TYPE: RNA
<213> ORGANISM: Homo sapiens

<400> SEQUENCE: 30
gcgcgaaugu guguuuaaaa aaauaaaac cuuggaguaa aguagcagca cauaaugguu     60 uggauuuu gaaaaggugc aggccauauu gugcugccuc aaaaauac                  108

<210> SEQ ID NO 31
<211> LENGTH: 83
<212> TYPE: RNA
<213> ORGANISM: Homo sapiens

<400> SEQUENCE: 31
ccuuggagua aaguagcagc acauaauggu uuguggauuu ugaaaaggug caggccauau    60
ugugcugccu caaaaauaca agg                                           83

<210> SEQ ID NO 32
<211> LENGTH: 64
<212> TYPE: RNA
<213> ORGANISM: Homo sapiens

<400> SEQUENCE: 32
cuguagcagc acaucauggu uuacaugcua cagucaagau gcgaaucauu auuugcugcu    60
cuag                                                                64
```

```
<210> SEQ ID NO 33
<211> LENGTH: 98
<212> TYPE: RNA
<213> ORGANISM: Homo sapiens

<400> SEQUENCE: 33
uugaggccuu aaaguacugu agcagcacau caugguuuac augcuacagu caagaugcga    60
aucauuauuu gcugcucuag aaauuuaagg aaauucau                           98

<210> SEQ ID NO 34
<211> LENGTH: 89
<212> TYPE: RNA
<213> ORGANISM: Homo sapiens

<400> SEQUENCE: 34
gucagcagug ccuuagcagc acguaaauau uggcguuaag auucuaaaau uaucuccagu    60
auuaacugug cugcugaagu aagguugac                                     89

<210> SEQ ID NO 35
<211> LENGTH: 81
<212> TYPE: RNA
<213> ORGANISM: Homo sapiens

<400> SEQUENCE: 35
guuccacucu agcagcacgu aaauauuggc guagugaaau auauauuaaa caccaauauu    60
acugugcugc uuuaguguga c                                             81

<210> SEQ ID NO 36
<211> LENGTH: 81
<212> TYPE: RNA
<213> ORGANISM: Homo sapiens

<400> SEQUENCE: 36
gcagugccuu agcagcacgu aaauauuggc guuaagauuc uaaaauuauc uccaguauua    60
acugugcugc ugaaguaagg u                                             81

<210> SEQ ID NO 37
<211> LENGTH: 84
<212> TYPE: RNA
<213> ORGANISM: Homo sapiens

<400> SEQUENCE: 37
gucagaauaa ugucaaagug cuuacagugc agguagugau augugcaucu acugcaguga    60
aggcacuugu agcauuaugg ugac                                          84

<210> SEQ ID NO 38
<211> LENGTH: 71
<212> TYPE: RNA
<213> ORGANISM: Homo sapiens

<400> SEQUENCE: 38
uguucuaagg ugcaucuagu gcagauagug aaguagauua gcaucuacug cccuaagugc    60
uccuucuggc a                                                        71

<210> SEQ ID NO 39
<211> LENGTH: 81
<212> TYPE: RNA
<213> ORGANISM: Homo sapiens

<400> SEQUENCE: 39
```

```
uuuuuguucu aaggugcauc uagugcagau agugaaguag auuagcaucu acugcccuaa    60
gugcuccuuc uggcauaaga a                                             81

<210> SEQ ID NO 40
<211> LENGTH: 82
<212> TYPE: RNA
<213> ORGANISM: Homo sapiens

<400> SEQUENCE: 40
gcaguccucu guuaguuuug cauaguugca cuacaagaag aauguaguug ugcaaaucua    60
ugcaaaacug augguggccu gc                                            82

<210> SEQ ID NO 41
<211> LENGTH: 80
<212> TYPE: RNA
<213> ORGANISM: Homo sapiens

<400> SEQUENCE: 41
caguccucug uuaguuuugc auaguugcac uacaagaaga auguaguugu gcaaaucuau    60
gcaaaacuga ugguggccug                                               80

<210> SEQ ID NO 42
<211> LENGTH: 87
<212> TYPE: RNA
<213> ORGANISM: Homo sapiens

<400> SEQUENCE: 42 cacguucua ugguuaguuu ugcagguuug cauccagcug ugugauauuc ugcugugcaa     60
auccaugcaa aacugacugu gguagug                                       87

<210> SEQ ID NO 43
<211> LENGTH: 96
<212> TYPE: RNA
<213> ORGANISM: Homo sapiens

<400> SEQUENCE: 43
acauugcuac uuacaauuag uuuugcaggu uugcauuuca gcguauauau guauaugugg    60
cugugcaaau ccaugcaaaa cugauuguga uaaugu                             96

<210> SEQ ID NO 44
<211> LENGTH: 80
<212> TYPE: RNA
<213> ORGANISM: Homo sapiens

<400> SEQUENCE: 44 uucuauggu aguuuugcag guuugcaucc agcuguguga uauucugcug ugcaaaucca     60
ugcaaaacug acugugguag                                               80

<210> SEQ ID NO 45
<211> LENGTH: 81
<212> TYPE: RNA
<213> ORGANISM: Homo sapiens

<400> SEQUENCE: 45
uuacaauuag uuuugcaggu uugcauuuca gcguauauau guauaugugg cugugcaaau    60
ccaugcaaaa cugauuguga u                                             81

<210> SEQ ID NO 46
<211> LENGTH: 71
<212> TYPE: RNA
```

<213> ORGANISM: Homo sapiens

<400> SEQUENCE: 46
guagcacuaa agugcuuaua gugcagguag uguuuaguua ucuacugcau uaugagcacu    60
uaaaguacug c    71

<210> SEQ ID NO 47
<211> LENGTH: 72
<212> TYPE: RNA
<213> ORGANISM: Homo sapiens

<400> SEQUENCE: 47
ugucggguag cuuaucagac ugauguugac uguugaaucu cauggcaaca ccagucgaug    60
ggcugucuga ca    72

<210> SEQ ID NO 48
<211> LENGTH: 81
<212> TYPE: RNA
<213> ORGANISM: Homo sapiens

<400> SEQUENCE: 48
accuugucgg guagcuuauc agacugaugu ugacuguuga aucucauggc aacaccaguc    60
gaugggcugu cugacauuuu g    81

<210> SEQ ID NO 49
<211> LENGTH: 85
<212> TYPE: RNA
<213> ORGANISM: Homo sapiens

<400> SEQUENCE: 49
ggcugagccg caguaguucu ucaguggcaa gcuuuauguc cugacccagc uaaagcugcc    60
aguugaagaa cuguugcccu cugcc    85

<210> SEQ ID NO 50
<211> LENGTH: 73
<212> TYPE: RNA
<213> ORGANISM: Homo sapiens

<400> SEQUENCE: 50
ggccggcugg gguuccuggg gaugggauuu gcuuccuguc acaaaucaca uugccaggga    60
uuuccaaccg acc    73

<210> SEQ ID NO 51
<211> LENGTH: 97
<212> TYPE: RNA
<213> ORGANISM: Homo sapiens

<400> SEQUENCE: 51
cucaggugcu cuggcugcuu ggguuccugg caugcugauu ugacuuaa gauuaaaauc    60 acauugccag ggauuaccac gcaaccacga ccuuggc    97

<210> SEQ ID NO 52
<211> LENGTH: 81
<212> TYPE: RNA
<213> ORGANISM: Homo sapiens

<400> SEQUENCE: 52
ccacggccgg cuggguucc uggggauggg auuugcuucc ugucacaaau cacauugcca    60
gggauuucca accgacccug a    81

```
<210> SEQ ID NO 53
<211> LENGTH: 68
<212> TYPE: RNA
<213> ORGANISM: Homo sapiens

<400> SEQUENCE: 53
cuccggugcc uacugagcug auaucaguuc ucauuuuaca cacuggcuca guucagcagg      60
aacaggag                                                              68

<210> SEQ ID NO 54
<211> LENGTH: 73
<212> TYPE: RNA
<213> ORGANISM: Homo sapiens

<400> SEQUENCE: 54
cucugccucc cgugccuacu gagcugaaac acaguugguu uguguacacu ggcucaguuc      60
agcaggaaca ggg                                                        73

<210> SEQ ID NO 55
<211> LENGTH: 81
<212> TYPE: RNA
<213> ORGANISM: Homo sapiens

<400> SEQUENCE: 55
cccugggcuc ugccucccgu gccuacugag cugaaacaca guuggguugu guacacuggc      60
ucaguucagc aggaacaggg g                                               81

<210> SEQ ID NO 56
<211> LENGTH: 71
<212> TYPE: RNA
<213> ORGANISM: Homo sapiens

<400> SEQUENCE: 56
cccuccggug ccuacugagc ugauaucagu ucucauuuua cacacuggcu caguucagca      60
ggaacagcau c                                                          71

<210> SEQ ID NO 57
<211> LENGTH: 84
<212> TYPE: RNA
<213> ORGANISM: Homo sapiens

<400> SEQUENCE: 57
ggccaguguu gagaggcgga dacuugggca auugcuggac gcugcccugg gcauugcacu      60
ugucucgguc ugacagugcc ggcc                                            84

<210> SEQ ID NO 58
<211> LENGTH: 86
<212> TYPE: RNA
<213> ORGANISM: Homo sapiens

<400> SEQUENCE: 58 aggccgugc cucguucaag uaauccagga uaggcugugc aggucccaau ggccuaucuu      60
gguuacuugc acgggacgc gggccu                                           86

<210> SEQ ID NO 59
<211> LENGTH: 77
<212> TYPE: RNA
<213> ORGANISM: Homo sapiens

<400> SEQUENCE: 59
```

```
guggccucgu ucaaguaauc caggauaggc ugugcagguc ccaaugggcc uauucuuggu    60
uacuugcacg gggacgc                                                   77

<210> SEQ ID NO 60
<211> LENGTH: 84
<212> TYPE: RNA
<213> ORGANISM: Homo sapiens

<400> SEQUENCE: 60
ggcuguggcu ggauucaagu aauccaggau aggcuguuuc caucugugag gccuauucuu    60
gauuacuugu uucuggaggc agcu                                           84

<210> SEQ ID NO 61
<211> LENGTH: 77
<212> TYPE: RNA
<213> ORGANISM: Homo sapiens

<400> SEQUENCE: 61
ccgggaccca guucaaguaa uucaggauag guugugugcu guccagccug uucuccauua    60
cuuggcucgg ggaccgg                                                   77

<210> SEQ ID NO 62
<211> LENGTH: 78
<212> TYPE: RNA
<213> ORGANISM: Homo sapiens

<400> SEQUENCE: 62
cugaggagca gggcuuagcu gcuugugagc agggccaca ccaagucgug uucacagugg     60
cuaaguuccg cccccccag                                                 78

<210> SEQ ID NO 63
<211> LENGTH: 73
<212> TYPE: RNA
<213> ORGANISM: Homo sapiens

<400> SEQUENCE: 63
aggugcagag cuuagcugau uggugaacag ugauuggutu ccgcuuuguu cacaguggcu    60
aaguucugca ccu                                                       73

<210> SEQ ID NO 64
<211> LENGTH: 97
<212> TYPE: RNA
<213> ORGANISM: Homo sapiens

<400> SEQUENCE: 64
accucucuaa caaggugcag agcuuagcug auuggugaac agugauuggu uccgcuuug     60 uucacagugg cuaaguucug caccugaaga gaaggug                             97

<210> SEQ ID NO 65
<211> LENGTH: 80
<212> TYPE: RNA
<213> ORGANISM: Homo sapiens

<400> SEQUENCE: 65
ccugaggagc agggcuuagc ugcuugugag cagggccac accaagucgu guucacagug     60
gcuaaguucc gcccccccagg                                               80

<210> SEQ ID NO 66
<211> LENGTH: 86
<212> TYPE: RNA
```

<213> ORGANISM: Homo sapiens

<400> SEQUENCE: 66
gguccuugcc cucaaggagc ucacagucua uugaguuacc uuucugacuu ucccacuaga    60
uugugagcuc cuggagggca ggcacu    86

<210> SEQ ID NO 67
<211> LENGTH: 108
<212> TYPE: RNA
<213> ORGANISM: Homo sapiens

<400> SEQUENCE: 67
ccuucuguga cccuuagag gaugacugau ucuuuuggu guucagaguc aauauaauuu    60
ucuagcacca ucugaaaucg guuauaauga uggggaaga gcaccaug    108

<210> SEQ ID NO 68
<211> LENGTH: 64
<212> TYPE: RNA
<213> ORGANISM: Homo sapiens

<400> SEQUENCE: 68
augacugauu ucuuuuggug uucagaguca auauaauuuu cuagcaccau cugaaaucgg    60
uuau    64

<210> SEQ ID NO 69
<211> LENGTH: 81
<212> TYPE: RNA
<213> ORGANISM: Homo sapiens

<400> SEQUENCE: 69
cuucaggaag cugguuucau auggugguuu agauuuaaau agugauuguc uagcaccauu    60
ugaaaucagu guucuugggg g    81

<210> SEQ ID NO 70
<211> LENGTH: 81
<212> TYPE: RNA
<213> ORGANISM: Homo sapiens

<400> SEQUENCE: 70
cuucuggaag cugguuucac augguggcuu agauuuuucc aucuuuguau cuagcaccau    60
uugaaaucag uguuuuagga g    81

<210> SEQ ID NO 71
<211> LENGTH: 110
<212> TYPE: RNA
<213> ORGANISM: Homo sapiens

<400> SEQUENCE: 71
accacuggcc caucucuuac acaggcugac cgauuucucc ugguguucag agucuguuuu    60
ugucuagcac cauuugaaau cgguuaugau guaggggaa aagcagcagc    110

<210> SEQ ID NO 72
<211> LENGTH: 71
<212> TYPE: RNA
<213> ORGANISM: Homo sapiens

<400> SEQUENCE: 72
gcgacuguaa acauccucga cuggaagcug ugaagccaca gaugggcuuu cagucggaug    60
uuugcagcug c    71

```
<210> SEQ ID NO 73
<211> LENGTH: 60
<212> TYPE: RNA
<213> ORGANISM: Homo sapiens

<400> SEQUENCE: 73
auguaaacau ccuacacuca gcuguaauac auggauuggc ugggaggugg auguuuacgu      60

<210> SEQ ID NO 74
<211> LENGTH: 88
<212> TYPE: RNA
<213> ORGANISM: Homo sapiens

<400> SEQUENCE: 74
accaaguuuc aguucaugua aacauccuac acucagcugu aauacaugga uuggcuggga      60
gguggauguu uacuucagcu gacuugga                                        88

<210> SEQ ID NO 75
<211> LENGTH: 72
<212> TYPE: RNA
<213> ORGANISM: Homo sapiens

<400> SEQUENCE: 75
agauacugua aacauccuac acucucagcu guggaaagua agaaagcugg gagaaggcug      60
uuuacucuuu cu                                                         72

<210> SEQ ID NO 76
<211> LENGTH: 70
<212> TYPE: RNA
<213> ORGANISM: Homo sapiens

<400> SEQUENCE: 76
guuguuguaa acaucccga cuggaagcug uaagacacag cuaagcuuuc agucagaugu      60
uugcugcuac                                                            70

<210> SEQ ID NO 77
<211> LENGTH: 64
<212> TYPE: RNA
<213> ORGANISM: Homo sapiens

<400> SEQUENCE: 77
cuguaaacau ccuugacugg aagcuguaag guguucagag gagcuuucag ucggauguuu      60
acag                                                                  64

<210> SEQ ID NO 78
<211> LENGTH: 71
<212> TYPE: RNA
<213> ORGANISM: Homo sapiens

<400> SEQUENCE: 78
ggagaggagg caagaugcug gcauagcugu ugaacuggga accugcuaug ccaacauauu      60
gccaucuuuc c                                                          71

<210> SEQ ID NO 79
<211> LENGTH: 70
<212> TYPE: RNA
<213> ORGANISM: Homo sapiens

<400> SEQUENCE: 79
ggagauauug cacauuacua aguugcaugu ugucacggcc ucaaugcaau uuagugugug      60
```
ugauauuuuc                                                          70

<210> SEQ ID NO 80
<211> LENGTH: 110
<212> TYPE: RNA
<213> ORGANISM: Homo sapiens

<400> SEQUENCE: 80
gggggccgag agaggcgggc ggccccgcgg ugcauugcug uugcauugca cgugugugag    60
gcgggugcag ugccucggca gugcagcccg gagccggccc cuggcaccac              110

<210> SEQ ID NO 81
<211> LENGTH: 88
<212> TYPE: RNA
<213> ORGANISM: Homo sapiens

<400> SEQUENCE: 81
accaaguuuc aguucaugua aacauccuac acucagcugu aauacaugga uuggcuggga    60 ggugauguu uacuucagcu gacuugga                                       88

<210> SEQ ID NO 82
<211> LENGTH: 69
<212> TYPE: RNA
<213> ORGANISM: Homo sapiens

<400> SEQUENCE: 82
cuguggugca uuguaguugc auugcauguu cuggugguac ccaugcaaug uuccacagu    60 gcaucacag                                                           69

<210> SEQ ID NO 83
<211> LENGTH: 110
<212> TYPE: RNA
<213> ORGANISM: Homo sapiens

<400> SEQUENCE: 83
ggccagcugu gaguguuucu uuggcagugu cuuagcuggu uguugagc aauaguaagg      60 aagcaaucag caaguauacu gcccuagaag ugcugcacgu uguggggccc              110

<210> SEQ ID NO 84
<211> LENGTH: 84
<212> TYPE: RNA
<213> ORGANISM: Homo sapiens

<400> SEQUENCE: 84
gugcucgguu uguaggcagu gucauuagcu gauuguacug ggugguuac aaucacuaac     60 uccacugcca ucaaaacaag gcac                                          84

<210> SEQ ID NO 85
<211> LENGTH: 77
<212> TYPE: RNA
<213> ORGANISM: Homo sapiens

<400> SEQUENCE: 85
agucuaguua cuaggcagug uaguuagcug auugcuaaua guaccaauca cuaaccacac    60
ggccagguaa aaagauu                                                  77

<210> SEQ ID NO 86
<211> LENGTH: 82
<212> TYPE: RNA
<213> ORGANISM: Homo sapiens

<400> SEQUENCE: 86
ucagaauaau gucaaagugc uuacagugca gguagugaua ugugcaucua cugcagugaa    60
ggcacuugua gcauuauggu ga    82

<210> SEQ ID NO 87
<211> LENGTH: 78
<212> TYPE: RNA
<213> ORGANISM: Homo sapiens

<400> SEQUENCE: 87
cuuucuacac agguugggau cgguugcaau gcuguguuuc uguaugguau ugcacuuguc    60
ccggccuguu gaguuugg    78

<210> SEQ ID NO 88
<211> LENGTH: 75
<212> TYPE: RNA
<213> ORGANISM: Homo sapiens

<400> SEQUENCE: 88
ucaucccugg gugggauuu guugcauuac uuguguucua uauaaaguau ugcacuuguc    60
ccggccugug gaaga    75

<210> SEQ ID NO 89
<211> LENGTH: 80
<212> TYPE: RNA
<213> ORGANISM: Homo sapiens

<400> SEQUENCE: 89 cuggggcuc caaagugcug uucgugcagg uagugugauu acccaaccua cugcugagcu    60
agcacuuccc gagccccgg    80

<210> SEQ ID NO 90
<211> LENGTH: 81
<212> TYPE: RNA
<213> ORGANISM: Homo sapiens

<400> SEQUENCE: 90
aacacagugg gcacucaaua aaugucuguu gaauugaaau gcguuacauu caacgggau    60 uuauugagca cccacucugu g    81

<210> SEQ ID NO 91
<211> LENGTH: 78
<212> TYPE: RNA
<213> ORGANISM: Homo sapiens

<400> SEQUENCE: 91
uggccgauuu uggcacuagc acauuuuugc uugugucucu ccgcucugag caaucaugug    60
cagugccaau augggaaa    78

<210> SEQ ID NO 92
<211> LENGTH: 80
<212> TYPE: RNA
<213> ORGANISM: Homo sapiens

<400> SEQUENCE: 92
gugagcgacu guaaacaucc ucgacuggaa gcugugaagc cacagauggg cuuucagucg    60
gauguuugca gcugccuacu    80

<210> SEQ ID NO 93

```
<211> LENGTH: 80
<212> TYPE: RNA
<213> ORGANISM: Homo sapiens

<400> SEQUENCE: 93
gugagguagu aaguuguauu guugugggu agggauauua ggccccaauu agaagauaac    60
uauacaacuu acuacuuucc                                              80

<210> SEQ ID NO 94
<211> LENGTH: 70
<212> TYPE: RNA
<213> ORGANISM: Homo sapiens

<400> SEQUENCE: 94
ggcacccacc cguagaaccg accuugcggg gccuucgccg cacacaagcu cgucucgug    60 gguccguguc                                                         70

<210> SEQ ID NO 95
<211> LENGTH: 81
<212> TYPE: RNA
<213> ORGANISM: Homo sapiens

<400> SEQUENCE: 95
cccauuggca uaaacccgua gauccgaucu uguggugaag uggaccgcac aagcucgcuu    60
cuaugggucu gugucagugu g                                             81

<210> SEQ ID NO 96
<211> LENGTH: 108
<212> TYPE: RNA
<213> ORGANISM: Homo sapiens

<400> SEQUENCE: 96
aagagagaag auauugaggc cuguugccac aaacccguag auccgaacuu gugguauuag    60
uccgcacaag cuuguaucua uagguaugug ucguuaggc aaucucac                108

<210> SEQ ID NO 97
<211> LENGTH: 80
<212> TYPE: RNA
<213> ORGANISM: Homo sapiens

<400> SEQUENCE: 97
ccuguugcca caaacccgua gauccgaacu ugguauua guccgcacaa gcuuguaucu    60
auagguaugu gucuguuagg                                              80

<210> SEQ ID NO 98
<211> LENGTH: 110
<212> TYPE: RNA
<213> ORGANISM: Homo sapiens

<400> SEQUENCE: 98
aggcugcccu ggcucaguua ucacagugcu gaugcugucu auucuaaagg uacaguacug    60
ugauaacuga aggauggcag ccaucuuacc uuccaucaga ggagccucac              110

<210> SEQ ID NO 99
<211> LENGTH: 57
<212> TYPE: RNA
<213> ORGANISM: Homo sapiens

<400> SEQUENCE: 99
ucaguuauca cagugcugau gcugccauu cuaaagguac aguacuguga uaacuga       57
```

```
<210> SEQ ID NO 100
<211> LENGTH: 75
<212> TYPE: RNA
<213> ORGANISM: Homo sapiens

<400> SEQUENCE: 100
ugcccuggcu caguuaucac agugcugaug cugucuauuc uaaagguaca guacugugau      60
aacugaagga uggca                                                      75

<210> SEQ ID NO 101
<211> LENGTH: 79
<212> TYPE: RNA
<213> ORGANISM: Homo sapiens

<400> SEQUENCE: 101
acuguccuuu uucgguuauc augguaccga ugcuguauau cugaaaggua caguacugug      60
auaacugaag aauggugu                                                   79

<210> SEQ ID NO 102
<211> LENGTH: 75
<212> TYPE: RNA
<213> ORGANISM: Homo sapiens

<400> SEQUENCE: 102
uguccuuuuu cgguuaucau gguaccgaug cuguauaucu gaaagguaca guacugugau      60
aacugaagaa uggug                                                      75

<210> SEQ ID NO 103
<211> LENGTH: 81
<212> TYPE: RNA
<213> ORGANISM: Homo sapiens

<400> SEQUENCE: 103
cuucuggaag cugguuucac auggugggcuu agauuuuucc aucuuuguau cuagcaccau      60
uugaaaucag uguuuuagga g                                               81

<210> SEQ ID NO 104
<211> LENGTH: 81
<212> TYPE: RNA
<213> ORGANISM: Homo sapiens

<400> SEQUENCE: 104
cuucaggaag cugguuucau auggugguuu agauuuaaau agugauuguc uagcaccauu      60
ugaaaucagu guucuugggg g                                               81

<210> SEQ ID NO 105
<211> LENGTH: 78
<212> TYPE: RNA
<213> ORGANISM: Homo sapiens

<400> SEQUENCE: 105
uugugcuuuc agcuucuuua cagugcugcc uuguagcauu caggucaagc aacauuguac      60
agggcuauga aagaacca                                                   78

<210> SEQ ID NO 106
<211> LENGTH: 78
<212> TYPE: RNA
<213> ORGANISM: Homo sapiens

<400> SEQUENCE: 106
```

```
uacugcccuc ggcuucuuua cagugcugcc uuguugcaua uggaucaagc agcauuguac    60
agggcuauga aggcauug                                                 78

<210> SEQ ID NO 107
<211> LENGTH: 78
<212> TYPE: RNA
<213> ORGANISM: Homo sapiens

<400> SEQUENCE: 107
aaaugucaga cagcccaucg acuguguug ccaugagauu caacagucaa caucagucug     60
auaagcuacc cgacaagg                                                 78

<210> SEQ ID NO 108
<211> LENGTH: 81
<212> TYPE: RNA
<213> ORGANISM: Homo sapiens

<400> SEQUENCE: 108
ugugcaucgu ggucaaaugc ucagacuccu guggugcug cucaugcacc acggauguuu    60
gagcaugugc uacggugucu a                                             81

<210> SEQ ID NO 109
<211> LENGTH: 81
<212> TYPE: RNA
<213> ORGANISM: Homo sapiens

<400> SEQUENCE: 109
ugugcaucgu ggucaaaugc ucagacuccu guggugcug cuuaugcacc acggauguuu    60
gagcaugugc uauggugucu a                                             81

<210> SEQ ID NO 110
<211> LENGTH: 81
<212> TYPE: RNA
<213> ORGANISM: Homo sapiens

<400> SEQUENCE: 110
ccuuggccau guaaaagugc uuacagugca gguagcuuuu ugagaucuac ugcaauguaa    60
gcacuucuua cauuaccaug g                                             81

<210> SEQ ID NO 111
<211> LENGTH: 82
<212> TYPE: RNA
<213> ORGANISM: Homo sapiens

<400> SEQUENCE: 111
ccugccgggg cuaaagugcu gacagugcag auaguggucc ucccgugcu accgcacugu     60 ggguacuugc ugcuccagca gg                                            82

<210> SEQ ID NO 112
<211> LENGTH: 81
<212> TYPE: RNA
<213> ORGANISM: Homo sapiens

<400> SEQUENCE: 112
cucucugcuu ucagcuucuu uacaguguug ccuuguggca uggaguucaa gcagcauugu    60
acagggcuau caaagcacag a                                             81

<210> SEQ ID NO 113
<211> LENGTH: 90
<212> TYPE: RNA
```

-continued

<213> ORGANISM: Homo sapiens

<400> SEQUENCE: 113
acacugcaag aacaauaagg auuuuuaggg gcauuaugac ugagucagaa aacacagcug    60 cccugaaag ucccucauuu uucuugcugu                                     90

<210> SEQ ID NO 114
<211> LENGTH: 80
<212> TYPE: RNA
<213> ORGANISM: Homo sapiens

<400> SEQUENCE: 114
acugcaagag caauaaggau uuuuaggggc auuaugauag uggaauggaa acacaucugc    60
ccccaaaagu cccucauuuu                                               80

<210> SEQ ID NO 115
<211> LENGTH: 85
<212> TYPE: RNA
<213> ORGANISM: Homo sapiens

<400> SEQUENCE: 115
ccuuagcaga gcuguggagu gugacaaugg uguuugguc uaaacuauca aacgccauua    60
ucacacuaaa uagcuacugc uaggc                                         85

<210> SEQ ID NO 116
<211> LENGTH: 66
<212> TYPE: RNA
<213> ORGANISM: Homo sapiens

<400> SEQUENCE: 116
agcuguggag ugugacaaug guguuugugu ccaaacuauc aaacgccauu aucacacuaa    60
auagcu                                                              66

<210> SEQ ID NO 117
<211> LENGTH: 61
<212> TYPE: RNA
<213> ORGANISM: Homo sapiens

<400> SEQUENCE: 117
acauuauuac uuuuggguacg cgcugugaca cuucaaacuc guaccgugag uaauaaugcg    60
c                                                                   61

<210> SEQ ID NO 118
<211> LENGTH: 85
<212> TYPE: RNA
<213> ORGANISM: Homo sapiens

<400> SEQUENCE: 118
aggccucucu cuccguguuc acagcggacc uugauuuaaa uguccauaca auuaaggcac    60
gcggugaaug ccaagaaugg ggcug                                         85

<210> SEQ ID NO 119
<211> LENGTH: 110
<212> TYPE: RNA
<213> ORGANISM: Homo sapiens

<400> SEQUENCE: 119
aucaagauua gaggcucugc ucccguguu cacagcggac cuugauuuaa ugcauacaa    60 uuaaggcacg cggugaaugc caagagcgga gccuacggcu gcacuugaag              110

```
<210> SEQ ID NO 120
<211> LENGTH: 87
<212> TYPE: RNA
<213> ORGANISM: Homo sapiens

<400> SEQUENCE: 120
ugagggcccc ucugcguguu cacagcggac cuugauuuaa ugucuauaca auuaaggcac    60
gcggugaaug ccaagagagg cgccucc                                        87

<210> SEQ ID NO 121
<211> LENGTH: 68
<212> TYPE: RNA
<213> ORGANISM: Homo sapiens

<400> SEQUENCE: 121
cucugcgugu ucacagcgga ccuugauuua augucuauac aauuaaggca cgcggugaau    60
gccaagag                                                              68

<210> SEQ ID NO 122
<211> LENGTH: 67
<212> TYPE: RNA
<213> ORGANISM: Homo sapiens

<400> SEQUENCE: 122
cucuccgugu ucacagcgga ccuugauuua augucauaca auuaaggcac gcggugaaug    60
ccaagag                                                               67

<210> SEQ ID NO 123
<211> LENGTH: 86
<212> TYPE: RNA
<213> ORGANISM: Homo sapiens

<400> SEQUENCE: 123
ugccagucuc uaggucccug agacccuuua accugugagg acauccaggg ucacaggkuga    60 gguucuuggg agccuggcgu cuggcc                                          86

<210> SEQ ID NO 124
<211> LENGTH: 65
<212> TYPE: RNA
<213> ORGANISM: Homo sapiens

<400> SEQUENCE: 124
ggucccugag acccuuuaac cugugaggac auccaggguc acaggugagg uucuugggag    60
ccugg                                                                 65

<210> SEQ ID NO 125
<211> LENGTH: 88
<212> TYPE: RNA
<213> ORGANISM: Homo sapiens

<400> SEQUENCE: 125
ugcgcuccuc ucaguccccug agacccuaac uugugauguu uaccguuuaa auccacgggu    60
uaggcucuug ggagcugcga gucgugcu                                        88

<210> SEQ ID NO 126
<211> LENGTH: 89
<212> TYPE: RNA
<213> ORGANISM: Homo sapiens

<400> SEQUENCE: 126
```
accagacuuu uccuagcccu gagacccua acuugugagg uauuuagua acaucacaag        60 ucaggcucuu gggaccuagg cggagggga                                        89

<210> SEQ ID NO 127
<211> LENGTH: 85
<212> TYPE: RNA
<213> ORGANISM: Homo sapiens

<400> SEQUENCE: 127
cgcuggcgac gggacauuau uacuuuuggu acgcgcugug acacuucaaa cucguaccgu      60
gaguaauaau gcgccgucca cggca                                           85

<210> SEQ ID NO 128
<211> LENGTH: 61
<212> TYPE: RNA
<213> ORGANISM: Homo sapiens

<400> SEQUENCE: 128
acauuauuac uuuugguacg cgcugugaca cuucaaacuc guaccgugag uaauaaugcg      60
c                                                                     61

<210> SEQ ID NO 129
<211> LENGTH: 97
<212> TYPE: RNA
<213> ORGANISM: Homo sapiens

<400> SEQUENCE: 129
ugugaucacu gucuccagcc ugcugaagcu cagagggcuc ugauucagaa agaucaucgg      60
auccgucuga gcuuggcugg ucggaagucu caucauc                              97

<210> SEQ ID NO 130
<211> LENGTH: 70
<212> TYPE: RNA
<213> ORGANISM: Homo sapiens

<400> SEQUENCE: 130
ccagccugcu gaagcucaga gggcucugau ucagaaagau caucggaucc gucugagcuu      60
ggcuggucgg                                                            70

<210> SEQ ID NO 131
<211> LENGTH: 82
<212> TYPE: RNA
<213> ORGANISM: Homo sapiens

<400> SEQUENCE: 131
ugagcuguug gauucggggc cguagcacug ucugagaggu uuacauuucu cacagugaac      60
cggucucuuu uucagcugcu uc                                              82

<210> SEQ ID NO 132
<211> LENGTH: 110
<212> TYPE: RNA
<213> ORGANISM: Homo sapiens

<400> SEQUENCE: 132
gcccggcagc cacugugcag ugggaagggg ggccgauaca cuguacgaga gugaguagca      60
ggucucacag ugaaccgguc ucuuucccua cugugucaca cuccuaaugg                110

<210> SEQ ID NO 133
<211> LENGTH: 70
<212> TYPE: RNA

<213> ORGANISM: Homo sapiens

<400> SEQUENCE: 133

```
guuggauucg gggccguagc acugucugag agguuuacau uucucacagu gaaccggucu    60
cuuuuucagc                                                           70
```

<210> SEQ ID NO 134
<211> LENGTH: 74
<212> TYPE: RNA
<213> ORGANISM: Homo sapiens

<400> SEQUENCE: 134

```
uggaucuuuu ugcggucugg gcuugcuguu ccucucaaca guaugucagga agcccuuacc   60
ccaaaaagua ucua                                                      74
```

<210> SEQ ID NO 135
<211> LENGTH: 90
<212> TYPE: RNA
<213> ORGANISM: Homo sapiens

<400> SEQUENCE: 135

```
ugcccuucgc gaaucuuuuu gcggucuggg cuugcuguac auaacucaau agccggaagc    60
ccuuaccccca aaaagcauuu gcggagggcg                                    90
```

<210> SEQ ID NO 136
<211> LENGTH: 89
<212> TYPE: RNA
<213> ORGANISM: Homo sapiens

<400> SEQUENCE: 136

```
ugcugcuggc cagagcucuu uucacauugu gcuacugucu gcaccuguca cuagcagugc    60
aauguuaaaa gggcauuggc cguguagug                                      89
```

<210> SEQ ID NO 137
<211> LENGTH: 110
<212> TYPE: RNA
<213> ORGANISM: Homo sapiens

<400> SEQUENCE: 137

```
gccaggaggc gggguugguu guuaucuuug guuaucuagc uguaugagug guguggaguc    60
uucauaaagc uagauaaccg aaaguaaaaa uaaccccaua cacugcgcag               110
```

<210> SEQ ID NO 138
<211> LENGTH: 110
<212> TYPE: RNA
<213> ORGANISM: Homo sapiens

<400> SEQUENCE: 138

```
cacggcgcgg cagcggcacu ggcuaaggga ggcccguuuc ucucuuuggu uaucuagcug    60
uaugagugcc acagagccgu cauaaagcua gauaaccgaa aguagaaaug               110
```

<210> SEQ ID NO 139
<211> LENGTH: 72
<212> TYPE: RNA
<213> ORGANISM: Homo sapiens

<400> SEQUENCE: 139

```
guuguuaucu uugguuaucu agcuguauga guguauuggu cuucauaaag cuagauaacc    60
gaaaguaaaa ac                                                        72
```

```
<210> SEQ ID NO 140
<211> LENGTH: 101
<212> TYPE: RNA
<213> ORGANISM: Homo sapiens

<400> SEQUENCE: 140
ccgcccccgc gucuccaggg caaccguggc uuucgauugu acuguggga acuggaggua      60 acagucuaca gccauggucg ccccgcagca cgcccacgcg c                        101

<210> SEQ ID NO 141
<211> LENGTH: 66
<212> TYPE: RNA
<213> ORGANISM: Homo sapiens

<400> SEQUENCE: 141
gggcaaccgu ggcuuucgau uguuacugug gaacuggag guaacagucu acagccaugg      60
ucgccc                                                               66

<210> SEQ ID NO 142
<211> LENGTH: 88
<212> TYPE: RNA
<213> ORGANISM: Homo sapiens

<400> SEQUENCE: 142
acaaugcuuu gcuagagcug guaaaaugga accaaaucgc cucuucaaug gauuuggucc      60
ccuucaacca gcuguagcua ugcauuga                                        88

<210> SEQ ID NO 143
<211> LENGTH: 102
<212> TYPE: RNA
<213> ORGANISM: Homo sapiens

<400> SEQUENCE: 143
gggagccaaa ugcuuugcua gagcugguaa aauggaacca aaucgacugu ccaauggauu      60 uggucccuu caaccagcug uagcugugca uugauggcgc cg                        102

<210> SEQ ID NO 144
<211> LENGTH: 68
<212> TYPE: RNA
<213> ORGANISM: Homo sapiens

<400> SEQUENCE: 144
gcuagagcug guaaaaugga accaaaucgc cucuucaaug gauuuggucc ccuucaacca      60
gcuguagc                                                              68

<210> SEQ ID NO 145
<211> LENGTH: 119
<212> TYPE: RNA
<213> ORGANISM: Homo sapiens

<400> SEQUENCE: 145
ccucagaaga aagaugcccc cugcucuggc uggucaaacg gaaccaaguc cgucuuccug      60
agagguuugg uccccuucaa ccagcuacag cagggcuggc aaugcccagu ccuuggaga     119

<210> SEQ ID NO 146
<211> LENGTH: 80
<212> TYPE: RNA
<213> ORGANISM: Homo sapiens

<400> SEQUENCE: 146
```

```
gcccccugcu cuggcugguc aaacggaacc aaguccgucu uccugagagg uuuggucccc    60
uucaaccagc uacagcaggg                                               80

<210> SEQ ID NO 147
<211> LENGTH: 73
<212> TYPE: RNA
<213> ORGANISM: Homo sapiens

<400> SEQUENCE: 147
cagggugugu gacugguuga ccagaggggc augcacugug uuacccugu gggccaccua    60 gucaccaacc cuc                                                      73

<210> SEQ ID NO 148
<211> LENGTH: 71
<212> TYPE: RNA
<213> ORGANISM: Homo sapiens

<400> SEQUENCE: 148
agggugugug acugguugac cagaggggca ugcacugugu ucacccugug gccaccuag    60 ucaccaaccc u                                                        71

<210> SEQ ID NO 149
<211> LENGTH: 90
<212> TYPE: RNA
<213> ORGANISM: Homo sapiens

<400> SEQUENCE: 149
aggccucgcu guucucuaug gcuuuuuauu ccuaugugau ucuacugcuc acucauauag    60
ggauuggagc cguggcgcac ggcggggaca                                    90

<210> SEQ ID NO 150
<211> LENGTH: 100
<212> TYPE: RNA
<213> ORGANISM: Homo sapiens

<400> SEQUENCE: 150
agauaaauuc acucuagugc uuuauggcuu uuuauuccua ugugauagua auaaagucuc    60
auguagggau ggaagccaug aaauacauug ugaaaaauca                         100

<210> SEQ ID NO 151
<211> LENGTH: 60
<212> TYPE: RNA
<213> ORGANISM: Homo sapiens

<400> SEQUENCE: 151
cuauggcuuu uuauuccuau gugauucuac ugcucacuca auaugggauu ggagccgugg    60

<210> SEQ ID NO 152
<211> LENGTH: 97
<212> TYPE: RNA
<213> ORGANISM: Homo sapiens

<400> SEQUENCE: 152
cacucugcug uggccuaugg cuuuucauuc cuaugugauu gcugucccaa acucauguag    60
ggcuaaaagc caugggcuac agugaggggc gagcucc                            97

<210> SEQ ID NO 153
<211> LENGTH: 82
<212> TYPE: RNA
<213> ORGANISM: Homo sapiens
```

```
<400> SEQUENCE: 153
ugagcccucg gaggacucca uuuguuuuga ugauggauuc uuaugcucca ucaucgucuc    60
aaaugagucu ucagagggu cu                                              82

<210> SEQ ID NO 154
<211> LENGTH: 62
<212> TYPE: RNA
<213> ORGANISM: Homo sapiens

<400> SEQUENCE: 154
gaggacucca uuuguuuuga ugauggauuc uuaugcucca ucaucgucuc aaaugagucu    60
uc                                                                   62

<210> SEQ ID NO 155
<211> LENGTH: 73
<212> TYPE: RNA
<213> ORGANISM: Homo sapiens

<400> SEQUENCE: 155
cuucggugac ggguauucuu gggugauaa uacggauuac guuguuauug cuuaagaaua     60
cgcguagucg agg                                                       73

<210> SEQ ID NO 156
<211> LENGTH: 99
<212> TYPE: RNA
<213> ORGANISM: Homo sapiens

<400> SEQUENCE: 156
cccuggcaug guguggug ggcagcuggug uugugaauca ggccguugcc aaucagagaa     60
cggcuacuuc acaacaccag ggccacacca cacuacagg                           99

<210> SEQ ID NO 157
<211> LENGTH: 84
<212> TYPE: RNA
<213> ORGANISM: Homo sapiens

<400> SEQUENCE: 157
cguugcugca gcuggguug ugaaucaggc cgacgagcag cgcauccucu uacccggcua     60
uuucacgaca ccaggguugc auca                                           84

<210> SEQ ID NO 158
<211> LENGTH: 71
<212> TYPE: RNA
<213> ORGANISM: Homo sapiens

<400> SEQUENCE: 158
cagcuggugu ugugaaucag gccgacgagc agcgcauccu cuuacccggc uauuucacga    60
caccaggguu g                                                         71

<210> SEQ ID NO 159
<211> LENGTH: 68
<212> TYPE: RNA
<213> ORGANISM: Homo sapiens

<400> SEQUENCE: 159
guguauucua cagugcacgu gucccagug uggcucggag gcuggagacg cggcccuguu     60
ggaguaac                                                             68

<210> SEQ ID NO 160
```

```
<211> LENGTH: 100
<212> TYPE: RNA
<213> ORGANISM: Homo sapiens

<400> SEQUENCE: 160
ugugucucuc ucuguguccu gccaguggu uuacccuaug guagguuacg ucaugcuguu    60
cuaccacagg guagaaccac ggacaggaua ccggggcacc                        100

<210> SEQ ID NO 161
<211> LENGTH: 72
<212> TYPE: RNA
<213> ORGANISM: Homo sapiens

<400> SEQUENCE: 161
uccugccagu gguuuuaccc uaugguaggu uacgucaugc uguucuacca caggguagaa    60
ccacggacag ga                                                       72

<210> SEQ ID NO 162
<211> LENGTH: 70
<212> TYPE: RNA
<213> ORGANISM: Homo sapiens

<400> SEQUENCE: 162
ccugccagug guuuuacccu augguagguu acgucaugcu guucuaccac agggguagaac    60 cacggacagg                                                         70

<210> SEQ ID NO 163
<211> LENGTH: 95
<212> TYPE: RNA
<213> ORGANISM: Homo sapiens

<400> SEQUENCE: 163
cggccggccc uggguccauc uuccaguaca guguuggaug gucuaauugu gaagcuccua    60
acacugucug guaaagaugg cucccggguc gguuc                             95

<210> SEQ ID NO 164
<211> LENGTH: 72
<212> TYPE: RNA
<213> ORGANISM: Homo sapiens

<400> SEQUENCE: 164
ggguccaucu uccaguacag uguuggaugg ucuaauugug aagcccuaa cacugucugg     60 uaaagauggc cc                                                      72

<210> SEQ ID NO 165
<211> LENGTH: 64
<212> TYPE: RNA
<213> ORGANISM: Homo sapiens

<400> SEQUENCE: 165
acccauaaag uagaaagcac acuaacagc acuggagggu guaguguuuc cuacuuuaug      60
gaug                                                              64

<210> SEQ ID NO 166
<211> LENGTH: 106
<212> TYPE: RNA
<213> ORGANISM: Homo sapiens

<400> SEQUENCE: 166
gcgcagcgcc cugucuccca gccugaggug cagugcugca ucucggucagguugggaguc    60
```
ugagaugaag cacuguagcu caggaagaga gaaguuguuc ugcagc                106

<210> SEQ ID NO 167
<211> LENGTH: 63
<212> TYPE: RNA
<213> ORGANISM: Homo sapiens

<400> SEQUENCE: 167 ccugagguge agugcugcau cucuggucag uugggagucu gagaugaagc acuguagcuc    60
agg                                                                 63

<210> SEQ ID NO 168
<211> LENGTH: 86
<212> TYPE: RNA
<213> ORGANISM: Homo sapiens

<400> SEQUENCE: 168
uggggcccug gcugggauau caucauauac uguaaguuug cgaugagaca cuacaguaua    60
gaugauguac uaguccgggc accccc                                        86

<210> SEQ ID NO 169
<211> LENGTH: 66
<212> TYPE: RNA
<213> ORGANISM: Homo sapiens

<400> SEQUENCE: 169
ggcugggaua ucaucauaua cuguaaguuu gcgaugagac acuacaguau agaugaugua    60
cuaguc                                                              66

<210> SEQ ID NO 170
<211> LENGTH: 88
<212> TYPE: RNA
<213> ORGANISM: Homo sapiens

<400> SEQUENCE: 170
caccuugucc ucacggucca guuuucccag gaaucccuua gaugcuaaga uggggauucc    60
uggaaauacu guucuugagg ucaugguu                                      88

<210> SEQ ID NO 171
<211> LENGTH: 70
<212> TYPE: RNA
<213> ORGANISM: Homo sapiens

<400> SEQUENCE: 171
cucacggucc aguuuuccca ggaaucccuu agaugcuaag auggggauuc cuggaaauac    60
uguucuugag                                                          70

<210> SEQ ID NO 172
<211> LENGTH: 99
<212> TYPE: RNA
<213> ORGANISM: Homo sapiens

<400> SEQUENCE: 172
ccgaugugua uccucagcuu ugagaacuga auuccauggg uugugucagu gucagaccuc    60
ugaaauucag uucuucagcu gggauaucuc ugucaucgu                          99

<210> SEQ ID NO 173
<211> LENGTH: 65
<212> TYPE: RNA
<213> ORGANISM: Homo sapiens -continued

<400> SEQUENCE: 173
agcuuugaga acugaauucc auggguugug ucaguguca g accugugaaa uucaguucuu    60
cagcu    65

<210> SEQ ID NO 174
<211> LENGTH: 72
<212> TYPE: RNA
<213> ORGANISM: Homo sapiens

<400> SEQUENCE: 174
aaucuaaaga caacauuucu gcacacacac cagacuaugg aagccagugu guggaaaugc    60
uucugcuaga uu    72

<210> SEQ ID NO 175
<211> LENGTH: 68
<212> TYPE: RNA
<213> ORGANISM: Homo sapiens

<400> SEQUENCE: 175
gaggcaaagu ucugagacac uccgacucug aguaugauag aagucagugc acuacagaac    60
uuugucuc    68

<210> SEQ ID NO 176
<211> LENGTH: 99
<212> TYPE: RNA
<213> ORGANISM: Homo sapiens

<400> SEQUENCE: 176
caagcacgau uagcauuuga ggugaaguuc uguuauacac ucaggcugug gcucucugaa    60
agucagugca ucacagaacu uugucucgaa agcuuucua    99

<210> SEQ ID NO 177
<211> LENGTH: 70
<212> TYPE: RNA
<213> ORGANISM: Homo sapiens

<400> SEQUENCE: 177
aagcacgauu agcauuugag gugaaguucu guuauacacu caggcugugg cucucugaaa    60
gucagugcau    70

<210> SEQ ID NO 178
<211> LENGTH: 89
<212> TYPE: RNA
<213> ORGANISM: Homo sapiens

<400> SEQUENCE: 178
gccggcgccc gagcucuggc uccgugucuu cacucccgug cuuguccgag gagggaggga    60
gggacggggg cugugcuggg gcagcugga    89

<210> SEQ ID NO 179
<211> LENGTH: 53
<212> TYPE: RNA
<213> ORGANISM: Homo sapiens

<400> SEQUENCE: 179
gcucuggcuc cgugucuuca cucccgugcu guccgagga gggagggagg gac    53

<210> SEQ ID NO 180
<211> LENGTH: 84
<212> TYPE: RNA

```
<213> ORGANISM: Homo sapiens

<400> SEQUENCE: 180
cuccccaugg cccugucucc aacccuugu accagugcug ggcucagacc cugguacagg      60 ccuggggac agggaccugg ggac                                             84

<210> SEQ ID NO 181
<211> LENGTH: 64
<212> TYPE: RNA
<213> ORGANISM: Homo sapiens

<400> SEQUENCE: 181
cccugucucc aacccuugu accagugcug ggcucagacc cugguacagg ccuggggac       60 aggg                                                                  64

<210> SEQ ID NO 182
<211> LENGTH: 72
<212> TYPE: RNA
<213> ORGANISM: Homo sapiens

<400> SEQUENCE: 182 uuccugccc ucgaggagcu cacagucuag uaugucucau ccccuacuag acugaagcuc      60
cuugaggaca gg                                                         72

<210> SEQ ID NO 183
<211> LENGTH: 69
<212> TYPE: RNA
<213> ORGANISM: Homo sapiens

<400> SEQUENCE: 183
ccuguccuca aggagcuuca gucuaguagg ggaugagaca uacuagacug ugagcuccuc     60
gagggcagg                                                             69

<210> SEQ ID NO 184
<211> LENGTH: 87
<212> TYPE: RNA
<213> ORGANISM: Homo sapiens

<400> SEQUENCE: 184
uguccccccc ggcccagguu cugugauaca cuccgacucg ggcucuggag cagucagugc     60
augacagaac uugggcccgg aaggacc                                         87

<210> SEQ ID NO 185
<211> LENGTH: 71
<212> TYPE: RNA
<213> ORGANISM: Homo sapiens

<400> SEQUENCE: 185
ggcccagguu cugugauaca cuccgacucg ggcucuggag cagucagugc augacagaac     60
uugggccccg g                                                          71

<210> SEQ ID NO 186
<211> LENGTH: 90
<212> TYPE: RNA
<213> ORGANISM: Homo sapiens

<400> SEQUENCE: 186
cucacagcug ccagugucau uuuugugauc ugcagcuagu auucucacuc caguugcaua     60
gucacaaaag ugaucauugg caggugtggc                                      90
```

```
<210> SEQ ID NO 187
<211> LENGTH: 71
<212> TYPE: RNA
<213> ORGANISM: Homo sapiens

<400> SEQUENCE: 187
ucucucucuc ccuacacagcu gccaguguca uugucacaaa agugaucauu ggcaggugug      60
gcugcugcau g                                                           71

<210> SEQ ID NO 188
<211> LENGTH: 87
<212> TYPE: RNA
<213> ORGANISM: Homo sapiens

<400> SEQUENCE: 188
agcgguggcc agugucauuu uugugauguu gcagcuagua auaugagccc agugcauag       60 ucacaaaagu gaucauugga aacugug                                          87

<210> SEQ ID NO 189
<211> LENGTH: 69
<212> TYPE: RNA
<213> ORGANISM: Homo sapiens

<400> SEQUENCE: 189
cagugucauu uuugugaugu ugcagcuagu aauaugagcc caguugcaua gucacaaaag      60
ugaucauug                                                              69

<210> SEQ ID NO 190
<211> LENGTH: 84
<212> TYPE: RNA
<213> ORGANISM: Homo sapiens

<400> SEQUENCE: 190
gugguacuug aagauaggu auccguguug ccuucgcuuu auuugugacg aaucauacac       60
gguugaccua uuuuucagua ccaa                                             84

<210> SEQ ID NO 191
<211> LENGTH: 66
<212> TYPE: RNA
<213> ORGANISM: Homo sapiens

<400> SEQUENCE: 191
gaagauaggu uauccguguu gccuucgcuu uauuugugac gaaucauaca cgguugaccu      60
auuuuu                                                                 66

<210> SEQ ID NO 192
<211> LENGTH: 65
<212> TYPE: RNA
<213> ORGANISM: Homo sapiens

<400> SEQUENCE: 192
cuguuaaugc uaaucgugau aggguuuuu gccuccaacu gacuccuaca uauuagcauu       60
aacag                                                                  65

<210> SEQ ID NO 193
<211> LENGTH: 82
<212> TYPE: RNA
<213> ORGANISM: Homo sapiens

<400> SEQUENCE: 193
```
ccuaacacug ucugguaaag auggcucccg ggugguucu cucggcagua accuucaggg    60
agcccugaag accauggagg ac                                           82

<210> SEQ ID NO 194
<211> LENGTH: 110
<212> TYPE: RNA
<213> ORGANISM: Homo sapiens

<400> SEQUENCE: 194
gccgagaccg agugcacagg gcucugaccu augaauugac agccagugcu cucgucuccc    60
cucuggcugc caauuccaua ggucacaggu auguucgccu caaugccagc               110

<210> SEQ ID NO 195
<211> LENGTH: 80
<212> TYPE: RNA
<213> ORGANISM: Homo sapiens

<400> SEQUENCE: 195
ucccgccccc uguaacagca acuccaugug gaagugccca cugguuccag uggggcugcu    60
guuaucuggg gcgagggcca                                              80

<210> SEQ ID NO 196
<211> LENGTH: 70
<212> TYPE: RNA
<213> ORGANISM: Homo sapiens

<400> SEQUENCE: 196
aaagcugggu ugagagggcg aaaaaggaug aggugacugg ucugggcuac gcuaugcugc    60
ggcgcucggg                                                         70

<210> SEQ ID NO 197
<211> LENGTH: 64
<212> TYPE: RNA
<213> ORGANISM: Homo sapiens

<400> SEQUENCE: 197
cauuggccuc cuaagccagg gauugugggu ucgagucccca cccgggguaa agaaaggccg    60
aauu                                                               64

<210> SEQ ID NO 198
<211> LENGTH: 70
<212> TYPE: RNA
<213> ORGANISM: Homo sapiens

<400> SEQUENCE: 198
ccuaagccag ggauuguggg uucgagucccc accuggggua gaggugaaag uuccuuuuac    60
ggaauuuuuu                                                         70

<210> SEQ ID NO 199
<211> LENGTH: 108
<212> TYPE: RNA
<213> ORGANISM: Homo sapiens

<400> SEQUENCE: 199
caaugucagc agugccuuag cagcacguaa auauuggcgu uaagauucua aaauuaucuc    60
caguauuaac ugugcugcug aaguaagguu gaccauacuc uacaguug                108

<210> SEQ ID NO 200
<211> LENGTH: 81
<212> TYPE: RNA

```
<213> ORGANISM: Homo sapiens

<400> SEQUENCE: 200
gggcuuucaa gucacuagug guuccguuua guagaugauu gugcauuguu ucaaaauggu    60
gcccuaguga cuacaaagcc c                                              81

<210> SEQ ID NO 201
<211> LENGTH: 70
<212> TYPE: RNA
<213> ORGANISM: Homo sapiens

<400> SEQUENCE: 201
acgcaagugu ccuaggguga gcucagggag cacagaaacc uccagguggaa cagaagggca    60 aaagcucauu                                                           70

<210> SEQ ID NO 202
<211> LENGTH: 70
<212> TYPE: RNA
<213> ORGANISM: Homo sapiens

<400> SEQUENCE: 202
caugugucac uuucaggugg aguuucaaga gucccuuccu gguuccaccgu cuccuuugcu    60 cuuccacaac                                                           70

<210> SEQ ID NO 203
<211> LENGTH: 110
<212> TYPE: RNA
<213> ORGANISM: Homo sapiens

<400> SEQUENCE: 203
agaagggcua ucaggccagc cuucagagga cuccaaggaa cauucaacgc ugucggugag    60
uuugggauuu gaaaaaacca cugaccguug acuguaccuu gggguccuua              110

<210> SEQ ID NO 204
<211> LENGTH: 110
<212> TYPE: RNA
<213> ORGANISM: Homo sapiens

<400> SEQUENCE: 204
ccugugcaga gauuauuuuu uaaaagguca caaucaacau ucauugcugu cgguggguug    60
aacugugugg acaagcucac ugaacaauga augcaacugu ggccccgcuu              110

<210> SEQ ID NO 205
<211> LENGTH: 89
<212> TYPE: RNA
<213> ORGANISM: Homo sapiens

<400> SEQUENCE: 205
cugauggcug cacucaacau ucauugcugu cgguggguuu gagucugaau caacucacug    60
aucaaugaau gcaaacugcg gaccaaaca                                      89

<210> SEQ ID NO 206
<211> LENGTH: 110
<212> TYPE: RNA
<213> ORGANISM: Homo sapiens

<400> SEQUENCE: 206
cggaaaauuu gccaggguu uggggggaaca uucaaccugu cggugaguuu ggcagcuca     60 ggcaaaccau cgaccguuga guggaccccug aggccuggaa uugccauccu             110
```

```
<210> SEQ ID NO 207
<211> LENGTH: 110
<212> TYPE: RNA
<213> ORGANISM: Homo sapiens

<400> SEQUENCE: 207
gagcugcuug ccuccccccg uuuuuggcaa ugguagaacu cacacuggug agguaacagg     60
auccgguggu ucuagacuug ccaacuaugg ggcgaggacu cagccggcac               110

<210> SEQ ID NO 208
<211> LENGTH: 70
<212> TYPE: RNA
<213> ORGANISM: Homo sapiens

<400> SEQUENCE: 208
uuuuuggcaa ugguagaacu cacacuggug agguaacagg auccgguggu ucuagacuug     60
ccaacuaugg                                                             70

<210> SEQ ID NO 209
<211> LENGTH: 110
<212> TYPE: RNA
<213> ORGANISM: Homo sapiens

<400> SEQUENCE: 209
ccgcagagug ugacuccugu ucuguguaug gcacugguag aauucacugu gaacagucuc     60
agucagugaa uuaccgaagg gccauaaaca gagcagagac agauccacga               110

<210> SEQ ID NO 210
<211> LENGTH: 84
<212> TYPE: RNA
<213> ORGANISM: Homo sapiens

<400> SEQUENCE: 210
ccagucacgu ccccuuauca cuuuuccagc ccagcuuugu gacuguaagu guuggacgga     60
gaacugauaa ggguaggguga uuga                                            84

<210> SEQ ID NO 211
<211> LENGTH: 65
<212> TYPE: RNA
<213> ORGANISM: Homo sapiens

<400> SEQUENCE: 211
ccuuaucacu uuccagccc agcuuuguga cuguaagugu uggacggaga acugauaagg      60
guagg                                                                   65

<210> SEQ ID NO 212
<211> LENGTH: 82
<212> TYPE: RNA
<213> ORGANISM: Homo sapiens

<400> SEQUENCE: 212 aggggggcgag ggauuggaga gaaaggcagu uccugauggu ccccuccca ggggcuggcu     60 uuccucuggu ccuuccccucc ca                                              82

<210> SEQ ID NO 213
<211> LENGTH: 66
<212> TYPE: RNA
<213> ORGANISM: Homo sapiens

<400> SEQUENCE: 213
```

-continued

```
agggauugga gagaaaggca guuccugaug guccccuccc caggggcugg cuuccucug    60 guccuu                                                              66

<210> SEQ ID NO 214
<211> LENGTH: 86
<212> TYPE: RNA
<213> ORGANISM: Homo sapiens

<400> SEQUENCE: 214
ugcuuguaac uuccaaaga auucuccuuu ugggcuuucu gguuuauuu uaagcccaaa     60 ggugaauuuu uugggaaguu ugagcu                                        86

<210> SEQ ID NO 215
<211> LENGTH: 71
<212> TYPE: RNA
<213> ORGANISM: Homo sapiens

<400> SEQUENCE: 215 acuuccaaa gaauucuccu uugggcuuu cugguuuuau uuuaagccca aaggugaauu     60
uuuugggaag u                                                        71

<210> SEQ ID NO 216
<211> LENGTH: 109
<212> TYPE: RNA
<213> ORGANISM: Homo sapiens

<400> SEQUENCE: 216
ggucgggcuc accaugacac agugugagac ucgggcuaca acacaggacc cggggcgcug   60
cucugacccc ucgugucuug guugcagcc ggagggacgc agguccgca               109

<210> SEQ ID NO 217
<211> LENGTH: 86
<212> TYPE: RNA
<213> ORGANISM: Homo sapiens

<400> SEQUENCE: 217
ugcucccucu cucacauccc uugcauggug gagggugagc uuucugaaaa ccccucccac   60 augcagggu ugcaggaugg cgagcc                                         86

<210> SEQ ID NO 218
<211> LENGTH: 68
<212> TYPE: RNA
<213> ORGANISM: Homo sapiens

<400> SEQUENCE: 218
ucucacaucc cuugcauggu ggagggugag cuuucugaaa accccuccca caugcagggu   60
uugcagga                                                            68

<210> SEQ ID NO 219
<211> LENGTH: 102
<212> TYPE: RNA
<213> ORGANISM: Homo sapiens

<400> SEQUENCE: 219
cugucgauug gacccgcccu ccggugccua cugagcugau ucaguucuc auuuacaca     60 cuggcucagu ucagcaggaa caggagucga gcccuugagc aa                    102

<210> SEQ ID NO 220
<211> LENGTH: 68
<212> TYPE: RNA
```

```
<213> ORGANISM: Homo sapiens

<400> SEQUENCE: 220
cuccggugcc uacugagcug auaucaguuc ucauuuuaca cacuggcuca guucagcagg    60
aacaggag                                                             68

<210> SEQ ID NO 221
<211> LENGTH: 85
<212> TYPE: RNA
<213> ORGANISM: Homo sapiens

<400> SEQUENCE: 221
ugcaggccuc ugugugauau guuugauaua uuagguuguu auuuaaucca acuauauauc    60
aaacauauuc cuacaguguc uugcc                                          85

<210> SEQ ID NO 222
<211> LENGTH: 67
<212> TYPE: RNA
<213> ORGANISM: Homo sapiens

<400> SEQUENCE: 222
cugugugaua uguuugauau auuagguugu uauuuaaucc aacuauauau caaacauauu    60
ccuacag                                                              67

<210> SEQ ID NO 223
<211> LENGTH: 92
<212> TYPE: RNA
<213> ORGANISM: Homo sapiens

<400> SEQUENCE: 223
cggcuggaca gcgggcaacg gaaucccaaa agcagcuguu gucccagag cauuccagcu     60 gcgcuuggau uucgucccu gcucuccugc cu                                   92

<210> SEQ ID NO 224
<211> LENGTH: 74
<212> TYPE: RNA
<213> ORGANISM: Homo sapiens

<400> SEQUENCE: 224
agcgggcaac ggaaucccaa aagcagcugu ugucuccaga gcauuccagc ugcgcuugga    60
uuucgucccc ugcu                                                      74

<210> SEQ ID NO 225
<211> LENGTH: 108
<212> TYPE: RNA
<213> ORGANISM: Homo sapiens

<400> SEQUENCE: 225
ccgagaccga gugcacaggg cucugaccua ugaauugaca gccagugcuc ucgucucccc    60
ucuggcugcc aauuccauag gucacaggua uguucgccuc aaugccag                108

<210> SEQ ID NO 226
<211> LENGTH: 110
<212> TYPE: RNA
<213> ORGANISM: Homo sapiens

<400> SEQUENCE: 226
gccgagaccg agugcacagg gcucugaccu augaauugac agccagugcu cucgucuccc    60
cucuggcugc caauuccaua ggucacaggu auguucgccu caaugccagc              110
```

```
<210> SEQ ID NO 227
<211> LENGTH: 88
<212> TYPE: RNA
<213> ORGANISM: Homo sapiens

<400> SEQUENCE: 227
cgaggauggg agcugagggc ugggucuuug cgggcgagau gagggugucg gaucaacugg      60
ccuacaaagu cccaguucuc ggcccccg                                        88

<210> SEQ ID NO 228
<211> LENGTH: 58
<212> TYPE: RNA
<213> ORGANISM: Homo sapiens

<400> SEQUENCE: 228
gcugggucuu ugcgggcgag augagggugu cggaucaacu ggccuacaaa gucccagu       58

<210> SEQ ID NO 229
<211> LENGTH: 85
<212> TYPE: RNA
<213> ORGANISM: Homo sapiens

<400> SEQUENCE: 229
augguguuau caaguguaac agcaacucca uguggacugu guaccaauuu ccaguggaga      60
ugcuguuacu uuugaugguu accaa                                           85

<210> SEQ ID NO 230
<211> LENGTH: 63
<212> TYPE: RNA
<213> ORGANISM: Homo sapiens

<400> SEQUENCE: 230
guguaacagc aacuccaugu ggacugugua ccaauuucca guggagaugc uguuacuuuu      60
gau                                                                   63

<210> SEQ ID NO 231
<211> LENGTH: 87
<212> TYPE: RNA
<213> ORGANISM: Homo sapiens

<400> SEQUENCE: 231
agcuucccug gcucuagcag cacagaaaua uuggcacagg gaagcgaguc ugccaauauu      60
ggcugugcug cuccaggcag gguggug                                         87

<210> SEQ ID NO 232
<211> LENGTH: 58
<212> TYPE: RNA
<213> ORGANISM: Homo sapiens

<400> SEQUENCE: 232
uagcagcaca gaaauauugg cacagggaag cgagucugcc aauauuggcu gugcugcu       58

<210> SEQ ID NO 233
<211> LENGTH: 110
<212> TYPE: RNA
<213> ORGANISM: Homo sapiens

<400> SEQUENCE: 233
cuagagcuug aauuggaacu gcugagugaa uuagguaguu ucauguuguu gggccugggu      60
uucugaacac aacaacauua aaccacccga uucacggcag uuacugcucc                110
```

-continued

```
<210> SEQ ID NO 234
<211> LENGTH: 70
<212> TYPE: RNA
<213> ORGANISM: Homo sapiens

<400> SEQUENCE: 234
gugaauuagg uaguuucaug uuguugggcc uggguuucug aacacaacaa cauuaaacca      60
cccgauucac                                                            70

<210> SEQ ID NO 235
<211> LENGTH: 110
<212> TYPE: RNA
<213> ORGANISM: Homo sapiens

<400> SEQUENCE: 235
ugcucgcuca gcugaucugu ggcuuaggua guuucauguu guugggauug aguuuugaac      60
ucggcaacaa gaaacugccu gaguuacauc agucgguuuu cgucgagggc                110

<210> SEQ ID NO 236
<211> LENGTH: 70
<212> TYPE: RNA
<213> ORGANISM: Homo sapiens

<400> SEQUENCE: 236
gugaauuagg uaguuucaug uuguugggcc uggguuucug aacacaacaa cauuaaacca      60
cccgauucac                                                            70

<210> SEQ ID NO 237
<211> LENGTH: 84
<212> TYPE: RNA
<213> ORGANISM: Homo sapiens

<400> SEQUENCE: 237
acuggucggu gauuuaggua guuccuguu guugggaucc accuuucucu cgacagcacg       60
acacugccuu cauuacuuca guug                                            84

<210> SEQ ID NO 238
<211> LENGTH: 75
<212> TYPE: RNA
<213> ORGANISM: Homo sapiens

<400> SEQUENCE: 238
ggcugugccg gguagagagg gcagugggag guaagagcuc uucacccuuc accaccuucu      60
ccacccagca uggcc                                                      75

<210> SEQ ID NO 239
<211> LENGTH: 60
<212> TYPE: RNA
<213> ORGANISM: Homo sapiens

<400> SEQUENCE: 239
gugcaugugu auguaugugu gcaugugcau guguaugugu augagugcau gcgugugugc      60

<210> SEQ ID NO 240
<211> LENGTH: 62
<212> TYPE: RNA
<213> ORGANISM: Homo sapiens

<400> SEQUENCE: 240
ucauuggucc agaggggaga uagguuccug ugauuuuucc uucuucucua uagaauaaau      60
```

```
ga                                                             62

<210> SEQ ID NO 241
<211> LENGTH: 71
<212> TYPE: RNA
<213> ORGANISM: Homo sapiens

<400> SEQUENCE: 241
gccaacccag uguucagacu accuguucag gaggcucuca auguguacag uagucugcac    60
auugguuagg c                                                        71

<210> SEQ ID NO 242
<211> LENGTH: 110
<212> TYPE: RNA
<213> ORGANISM: Homo sapiens

<400> SEQUENCE: 242
aggaagcuuc uggagauccu gcuccgucgc cccaguguuc agacuaccug uucaggacaa    60
ugccguugua caguagucug cacauugguu agacugggca agggagagca              110

<210> SEQ ID NO 243
<211> LENGTH: 110
<212> TYPE: RNA
<213> ORGANISM: Homo sapiens

<400> SEQUENCE: 243
ccagaggaca ccuccacucc gucuacccag uguuuagacu aucguucag gacucccaaa     60 uuguacagua gucugcacau ugguuaggcu gggcuggguu agacccucgg              110

<210> SEQ ID NO 244
<211> LENGTH: 71
<212> TYPE: RNA
<213> ORGANISM: Homo sapiens

<400> SEQUENCE: 244
gccaacccag uguucagacu accuguucag gaggcucuca auguguacag uagucugcac    60
auugguuagg c                                                        71

<210> SEQ ID NO 245
<211> LENGTH: 70
<212> TYPE: RNA
<213> ORGANISM: Homo sapiens

<400> SEQUENCE: 245
gccguggcca ucuuacuggg cagcauugga uggagucagg ucucuaauac ugccugguaa    60
ugaugacggc                                                          70

<210> SEQ ID NO 246
<211> LENGTH: 95
<212> TYPE: RNA
<213> ORGANISM: Homo sapiens

<400> SEQUENCE: 246
ccagcucggg cagccguggc caucuuacug ggcagcauug gauggaguca ggucucuaau    60
acugccuggu aaugaugacg gcggagcccu gcacg                              95

<210> SEQ ID NO 247
<211> LENGTH: 68
<212> TYPE: RNA
<213> ORGANISM: Homo sapiens
```

-continued

```
<400> SEQUENCE: 247
cccucgucuu acccagcagu guuugggugc gguugggagu cucuaauacu gccggguaau     60
gauggagg                                                              68

<210> SEQ ID NO 248
<211> LENGTH: 72
<212> TYPE: RNA
<213> ORGANISM: Homo sapiens

<400> SEQUENCE: 248
guuccuuuuu ccuaugcaua uacuucuuug aggaucuggc cuaaagaggu auagggcaug     60
ggaagaugga gc                                                         72

<210> SEQ ID NO 249
<211> LENGTH: 110
<212> TYPE: RNA
<213> ORGANISM: Homo sapiens

<400> SEQUENCE: 249 guguuggga cucgcgcgcu ggguccagug guucuuaaca guucaacagu ucguagcgc       60 aauugugaaa uguuuaggac cacuagaccc ggcgggcgcg gcgacagcga                110

<210> SEQ ID NO 250
<211> LENGTH: 110
<212> TYPE: RNA
<213> ORGANISM: Homo sapiens

<400> SEQUENCE: 250
ggcuacaguc uuucuucaug ugacucgugg acuucccuuu gucauccuau gccugagaau     60
auaugaagga ggcugggaag gcaaagggac guucaauugu caucacuggc                110

<210> SEQ ID NO 251
<211> LENGTH: 110
<212> TYPE: RNA
<213> ORGANISM: Homo sapiens

<400> SEQUENCE: 251
aaagauccuc agacaaucca ugugcuucuc uugucccuuca uuccaccgga gucugucuca   60
uacccaacca gauuucagug gagugaaguu caggaggcau ggagcugaca                110

<210> SEQ ID NO 252
<211> LENGTH: 86
<212> TYPE: RNA
<213> ORGANISM: Homo sapiens

<400> SEQUENCE: 252
ugcuucccga ggccacaugc uucuuuauau ccccauaugg auuacuuugc uauggaaugu    60
aaggaagugu gugguuucgg caagug                                         86

<210> SEQ ID NO 253
<211> LENGTH: 69
<212> TYPE: RNA
<213> ORGANISM: Homo sapiens

<400> SEQUENCE: 253
aggccacaug cuucuuuaua uccccauaug gauuacuuug cuauggaaug uaaggaagug    60
ugugguuuu                                                            69

<210> SEQ ID NO 254
```

```
<211> LENGTH: 71
<212> TYPE: RNA
<213> ORGANISM: Homo sapiens

<400> SEQUENCE: 254
ugacgggcga gcuuuggcc cggguuauac cugaugcuca cguauaagac gagcaaaaag      60
cuuguugguc a                                                          71

<210> SEQ ID NO 255
<211> LENGTH: 110
<212> TYPE: RNA
<213> ORGANISM: Homo sapiens

<400> SEQUENCE: 255
acccggcagu gccuccaggc gcagggcagc cccugcccac cgcacacugc gcugcccag       60 acccacugug cgugugacag cggcugaucu gugccugggc agcgcgaccc               110

<210> SEQ ID NO 256
<211> LENGTH: 110
<212> TYPE: RNA
<213> ORGANISM: Homo sapiens

<400> SEQUENCE: 256
ucaccuggcc augugacuug ugggcuuccc uuugucaucc uucgccuagg gcucugagca      60
gggcagggac agcaaagggg ugcucaguug ucacuuccca cagcacggag               110

<210> SEQ ID NO 257
<211> LENGTH: 110
<212> TYPE: RNA
<213> ORGANISM: Homo sapiens

<400> SEQUENCE: 257
cggggcaccc cgcccggaca gcgcgccggc accuggcuc uagacugcuu acugcccggg      60
ccgcccucag uaacagucuc cagucacggc caccgacgcc uggccccgcc               110

<210> SEQ ID NO 258
<211> LENGTH: 110
<212> TYPE: RNA
<213> ORGANISM: Homo sapiens

<400> SEQUENCE: 258
ccugugcaga gauuauuuuu uaaaagguca caaucaacau ucauugcugu cgguggguug      60
aacugugugg acaagcucac ugaacaauga augcaacugu ggccccgcuu               110

<210> SEQ ID NO 259
<211> LENGTH: 108
<212> TYPE: RNA
<213> ORGANISM: Homo sapiens

<400> SEQUENCE: 259
gaguuuugag guugcuucag ugaacauuca acgcugucgg ugaguuugga auuaaaauca      60
aaaccaucga ccguugauug uacccuaugg cuaaccauca ucuacucc                 108

<210> SEQ ID NO 260
<211> LENGTH: 110
<212> TYPE: RNA
<213> ORGANISM: Homo sapiens

<400> SEQUENCE: 260
ggccuggcug gacagaguug ucaugugucu gccugucuac acuugcugug cagaacaucc     60
```

| | |
|---|---|
| gcucaccugu acagcaggca cagacaggca gucacaugac aaccccagccu | 110 |

<210> SEQ ID NO 261
<211> LENGTH: 110
<212> TYPE: RNA
<213> ORGANISM: Homo sapiens

<400> SEQUENCE: 261

| | |
|---|---|
| aucauucaga aaugguauac aggaaaauga ccuaugaauu gacagacaau auagcugagu | 60 |
| uugucuguca uuucuuuagg ccaauauucu guaugacugu gcuacuucaa | 110 |

<210> SEQ ID NO 262
<211> LENGTH: 110
<212> TYPE: RNA
<213> ORGANISM: Homo sapiens

<400> SEQUENCE: 262

| | |
|---|---|
| gauggcugug aguuggcuua aucucagcug gcaacuguga gauguucaua caaucccuca | 60 |
| cagggucuc ugggauuaug cuaaacagag caauuuccua gcccucacga | 110 |

<210> SEQ ID NO 263
<211> LENGTH: 110
<212> TYPE: RNA
<213> ORGANISM: Homo sapiens

<400> SEQUENCE: 263

| | |
|---|---|
| aguauaauua uuacauaguu uuugaugucg cagauacugc aucaggaacu gauuggauaa | 60 |
| gaaucaguca ccaucaguuc cuaaugcauu gccuucagca ucuaaacaag | 110 |

<210> SEQ ID NO 264
<211> LENGTH: 110
<212> TYPE: RNA
<213> ORGANISM: Homo sapiens

<400> SEQUENCE: 264

| | |
|---|---|
| gugauaaugu agcgagauuu ucuguugugc uugaucuaac caugugguug cgagguauga | 60 |
| guaaaacaug guuccgucaa gcaccaugga acgucacgca gcuuucuaca | 110 |

<210> SEQ ID NO 265
<211> LENGTH: 110
<212> TYPE: RNA
<213> ORGANISM: Homo sapiens

<400> SEQUENCE: 265

| | |
|---|---|
| gaccagucgc ugcggggcuu uccuuugugc uugaucuaac cauggguggg aacgauggaa | 60 |
| acggaacaug guucugucaa gcaccgcgga aagcaccgug cucuccugca | 110 |

<210> SEQ ID NO 266
<211> LENGTH: 110
<212> TYPE: RNA
<213> ORGANISM: Homo sapiens

<400> SEQUENCE: 266

| | |
|---|---|
| ccgccccggg ccgcggcucc ugauugucca aacgcaauuc ucgagucuau ggcuccggcc | 60 |
| gagaguugag ucuggacguc ccgagccgcc gcccccaaac cucgagcggg | 110 |

<210> SEQ ID NO 267
<211> LENGTH: 110
<212> TYPE: RNA
<213> ORGANISM: Homo sapiens

<400> SEQUENCE: 267
ccgccccggg ccgcggcucc ugauugucca aacgcaauuc ucgagcuau ggcuccggcc    60 gagaguugag ucuggacguc ccgagccgcc gcccccaaac cucgagcggg             110

<210> SEQ ID NO 268
<211> LENGTH: 97
<212> TYPE: RNA
<213> ORGANISM: Homo sapiens

<400> SEQUENCE: 268
acucaggggc uucgccacug auuguccaaa cgcaauucuu guacgagucu gcggccaacc   60
gagaauugug gcuggacauc uggcugag uccggg                              97

<210> SEQ ID NO 269
<211> LENGTH: 110
<212> TYPE: RNA
<213> ORGANISM: Homo sapiens

<400> SEQUENCE: 269
gacagugugg cauuguaggg ucccacaccg uaucugacac uuugggcgag ggcaccaugc   60
ugaaggyguu caugaugcgg ucuggaacu ccucacggau cuuacugaug             110

<210> SEQ ID NO 270
<211> LENGTH: 110
<212> TYPE: RNA
<213> ORGANISM: Homo sapiens

<400> SEQUENCE: 270
ugaacaucca ggucuggggc augaaccugg cauacaaugu agauuucugu guucguuagg   60
caacagcuac auugucugcu ggguuucagg cuaccuggaa acauguucuc             110

<210> SEQ ID NO 271
<211> LENGTH: 110
<212> TYPE: RNA
<213> ORGANISM: Homo sapiens

<400> SEQUENCE: 271
gcugcuggaa gguguaggua cccucaaugg cucaguagcc aguguagauc cugucuuucg   60
uaaucagcag cuacaucugg cuacggguc ucgauggca cuucuagcu               110

<210> SEQ ID NO 272
<211> LENGTH: 110
<212> TYPE: RNA
<213> ORGANISM: Homo sapiens

<400> SEQUENCE: 272
ccuggccucc ugcagugcca cgcuccgugu auuugacaag cugaguugga cacuccaugu   60
gguagagugu caguuuguca aauacccaa gugcggcaca ugcuuaccag             110

<210> SEQ ID NO 273
<211> LENGTH: 81
<212> TYPE: RNA
<213> ORGANISM: Homo sapiens

<400> SEQUENCE: 273
gggcuuucaa gucacuagug guuccguuua guagaugauu gugcauuguu ucaaaauggu   60
gcccuaguga cuacaaagcc c                                             81

<210> SEQ ID NO 274

```
<211> LENGTH: 60
<212> TYPE: RNA
<213> ORGANISM: Homo sapiens

<400> SEQUENCE: 274
caaucuuccu uuaucauggu auugauuuuu cagugcuucc cuuugugug agagaagaua    60

<210> SEQ ID NO 275
<211> LENGTH: 80
<212> TYPE: RNA
<213> ORGANISM: Homo sapiens

<400> SEQUENCE: 275
aggacccuuc cagagggccc ccccucaauc cuguugugcc uaauucagag gguugggugg    60
aggcucuccu gaagggcucu                                              80

<210> SEQ ID NO 276
<211> LENGTH: 63
<212> TYPE: RNA
<213> ORGANISM: Homo sapiens

<400> SEQUENCE: 276
aagaaauggu uuaccguccc acauacauuu ugaauaugua ugugggaugg uaaaccgcuu    60
cuu                                                                63

<210> SEQ ID NO 277
<211> LENGTH: 86
<212> TYPE: RNA
<213> ORGANISM: Homo sapiens

<400> SEQUENCE: 277
acugcuaacg aaugcucuga cuuuauugca cuacuguacu uuacagcuag cagugcaaua    60
guauugucaa agcaucugaa agcagg                                        86

<210> SEQ ID NO 278
<211> LENGTH: 69
<212> TYPE: RNA
<213> ORGANISM: Homo sapiens

<400> SEQUENCE: 278
ccaccacuua aacguggaug uacuugcuuu gaaacuaaag aaguaagugc uuccauguuu    60
uggugaugg                                                          69

<210> SEQ ID NO 279
<211> LENGTH: 73
<212> TYPE: RNA
<213> ORGANISM: Homo sapiens

<400> SEQUENCE: 279
gcucccuuca acuuuaacau ggaagugcuu ucugugacuu uaaaaguaag ugcuuccaug    60
uuuuaguagg agu                                                     73

<210> SEQ ID NO 280
<211> LENGTH: 68
<212> TYPE: RNA
<213> ORGANISM: Homo sapiens

<400> SEQUENCE: 280
ccuuugcuuu aacauggggg uaccugcugu gugaaacaaa aguaagugcu uccauguuuc    60
aguggagg                                                           68
```

-continued

```
<210> SEQ ID NO 281
<211> LENGTH: 68
<212> TYPE: RNA
<213> ORGANISM: Homo sapiens

<400> SEQUENCE: 281
ccucuacuuu aacauggagg cacuugcugu gacaugacaa aaauaagugc uuccauguuu    60
gagugugg                                                            68

<210> SEQ ID NO 282
<211> LENGTH: 82
<212> TYPE: RNA
<213> ORGANISM: Homo sapiens

<400> SEQUENCE: 282
gcuucgcucc ccuccgccuu cucuucccgg uucuucccgg agucgggaaa agcugggpuug   60 agagggcgaa aaaggaugag gu                                            82

<210> SEQ ID NO 283
<211> LENGTH: 59
<212> TYPE: RNA
<213> ORGANISM: Homo sapiens

<400> SEQUENCE: 283
uuggccuccu aagccaggga uugugggpuuc gagucccacc cggggpuaaag aaaggccga   59

<210> SEQ ID NO 284
<211> LENGTH: 86
<212> TYPE: RNA
<213> ORGANISM: Homo sapiens

<400> SEQUENCE: 284
uugguacuug gagagaggug guccguggcg cguucgcuuu auuuauggcg cacauuacac    60
ggucgaccuc uuugcaguau cuaauc                                        86

<210> SEQ ID NO 285
<211> LENGTH: 83
<212> TYPE: RNA
<213> ORGANISM: Homo sapiens

<400> SEQUENCE: 285
cugacuaugc cucccgcau ccccuagggc auugguguaa agcuggagac ccacugcccc     60
aggugcugcu gggggpuugua guc                                          83

<210> SEQ ID NO 286
<211> LENGTH: 98
<212> TYPE: RNA
<213> ORGANISM: Homo sapiens

<400> SEQUENCE: 286
auacagugcu ugguuccuag uaggugucca guaaguguuu ugacauaau uuguuuauug     60 aggaccuccu aucaaucaag cacugugcua ggcucugg                           98

<210> SEQ ID NO 287
<211> LENGTH: 95
<212> TYPE: RNA
<213> ORGANISM: Homo sapiens

<400> SEQUENCE: 287
cucaucuguc uguugggcug gaggcagggc cuuugugaag gcggguggug cucagaucgc    60
```

```
cucugggccc uuccuccagc cccgaggcgg auuca                          95
```

<210> SEQ ID NO 288
<211> LENGTH: 75
<212> TYPE: RNA
<213> ORGANISM: Homo sapiens

<400> SEQUENCE: 288

```
uggaguggggg gggcaggagg ggcucaggga gaaagugcau acagcccug gcccucucug   60 cccuuccguc cccug                                                   75
```

<210> SEQ ID NO 289
<211> LENGTH: 94
<212> TYPE: RNA
<213> ORGANISM: Homo sapiens

<400> SEQUENCE: 289

```
cuuuggcgau cacugccucu cugggccugu gucuuaggcu cugcaagauc aaccgagcaa   60
agcacacggc cugcagagag gcagcgcucu gccc                              94
```

<210> SEQ ID NO 290
<211> LENGTH: 94
<212> TYPE: RNA
<213> ORGANISM: Homo sapiens

<400> SEQUENCE: 290

```
gaguuugguu uuguuugggu uguucuagg uaugguccca gggaucccag aucaaaccag    60
gccccugggc cuauccuaga accaaccuaa gcuc                              94
```

<210> SEQ ID NO 291
<211> LENGTH: 94
<212> TYPE: RNA
<213> ORGANISM: Homo sapiens

<400> SEQUENCE: 291

```
uguuuugagc gggggucaag agcaauaacg aaaaauguuu gucauaaacc guuuucauu    60 auugcuccug accuccucuc auuugcuaua uuca                              94
```

<210> SEQ ID NO 292
<211> LENGTH: 93
<212> TYPE: RNA
<213> ORGANISM: Homo sapiens

<400> SEQUENCE: 292

```
guagucagua guuggggggu gggaacggcu ucauacagga guugaugcac aguuauccag   60
cuccuauaug augccuuucu ucauccccuu caa                               93
```

<210> SEQ ID NO 293
<211> LENGTH: 67
<212> TYPE: RNA
<213> ORGANISM: Homo sapiens

<400> SEQUENCE: 293

```
ucuccaacaa uauccuggug cugagugaug acucaggcga cuccagcauc agugauuuug   60
uugaaga                                                            67
```

<210> SEQ ID NO 294
<211> LENGTH: 94
<212> TYPE: RNA
<213> ORGANISM: Homo sapiens

```
<400> SEQUENCE: 294
cggggcggcc gcucucccug uccuccagga gcucacgugu gccugccugu gagcgccucg    60
acgacagagc cggcgccugc cccagugucu gcgc                                94

<210> SEQ ID NO 295
<211> LENGTH: 95
<212> TYPE: RNA
<213> ORGANISM: Homo sapiens

<400> SEQUENCE: 295
uuguaccugg ugugauuaua aagcaaugag acugauuguc auaugucguu ugugggaucc    60
gucucaguua cuuuauagcc auaccuggua ucuua                               95

<210> SEQ ID NO 296
<211> LENGTH: 99
<212> TYPE: RNA
<213> ORGANISM: Homo sapiens

<400> SEQUENCE: 296
gaaacugggc ucaaggugag gggugcuauc ugugauugag ggacaugguu aauggaauug    60
ucucacacag aaaucgcacc cgucaccuug gccuacuua                           99

<210> SEQ ID NO 297
<211> LENGTH: 98
<212> TYPE: RNA
<213> ORGANISM: Homo sapiens

<400> SEQUENCE: 297
acccaaaccc uaggucugcu gacuccuagu ccagggcucg ugauggcugg ugggcccuga    60
acgagggguc uggaggccug gguuugaaua ucgacagc                            98

<210> SEQ ID NO 298
<211> LENGTH: 86
<212> TYPE: RNA
<213> ORGANISM: Homo sapiens

<400> SEQUENCE: 298
gucugucugc ccgcaugccu gccucucugu ugcucugaag gaggcagggg cugggccugc    60
agcugccugg gcagagcggc uccugc                                         86

<210> SEQ ID NO 299
<211> LENGTH: 68
<212> TYPE: RNA
<213> ORGANISM: Homo sapiens

<400> SEQUENCE: 299
ccauuacugu ugcuaauaug caacucuguu gaauauaaau uggaauugca cuuuagcaau    60
ggugaugg                                                             68

<210> SEQ ID NO 300
<211> LENGTH: 66
<212> TYPE: RNA
<213> ORGANISM: Homo sapiens

<400> SEQUENCE: 300
aaaaggugga uauuccuucu auguuuaugu uauuuauggu uaaacauaga ggaaauucca    60
cguuuu                                                               66

<210> SEQ ID NO 301
```

```
<211> LENGTH: 70
<212> TYPE: RNA
<213> ORGANISM: Homo sapiens

<400> SEQUENCE: 301
uugaagggag aucgaccgug uuauauucgc uuuauugacu ucgaauaaua caugguugau      60
cuuucucag                                                             70

<210> SEQ ID NO 302
<211> LENGTH: 75
<212> TYPE: RNA
<213> ORGANISM: Homo sapiens

<400> SEQUENCE: 302
agacagagaa gccaggucac gucucugcag uuacacagcu cacgagugcc ugcuggggug      60
gaaccugguc ugucu                                                      75

<210> SEQ ID NO 303
<211> LENGTH: 67
<212> TYPE: RNA
<213> ORGANISM: Homo sapiens

<400> SEQUENCE: 303
guggcacuca aacugugggg gcacuuucug cucucuggug aaagugccgc caucuuuga       60 guguuac                                                               67

<210> SEQ ID NO 304
<211> LENGTH: 67
<212> TYPE: RNA
<213> ORGANISM: Homo sapiens

<400> SEQUENCE: 304
gugggccuca aauguggagc acuauucuga uguccaagug gaaagugcug cgacauuuga      60
gcgucac                                                               67

<210> SEQ ID NO 305
<211> LENGTH: 69
<212> TYPE: RNA
<213> ORGANISM: Homo sapiens

<400> SEQUENCE: 305
gggauacuca aaauggggc gcuuuccuuu uugucuguac ugggaagugc uucgauuuug       60
ggguguccc                                                             69

<210> SEQ ID NO 306
<211> LENGTH: 72
<212> TYPE: RNA
<213> ORGANISM: Homo sapiens

<400> SEQUENCE: 306
uacaucggcc auuauaauac aaccugauaa guguuauagc acuuaucaga uuguauugua      60
auugucugug ua                                                         72

<210> SEQ ID NO 307
<211> LENGTH: 102
<212> TYPE: RNA
<213> ORGANISM: Homo sapiens

<400> SEQUENCE: 307
auggagcugc ucacccugug ggccucaaau guggaggaac uauucugaug uccaagugga      60
```

```
aagugcugcg acauuugagc gucaccggug acgcccauau ca                    102

<210> SEQ ID NO 308
<211> LENGTH: 101
<212> TYPE: RNA
<213> ORGANISM: Homo sapiens

<400> SEQUENCE: 308 gcaucccuc agccugugge acucaaacug uggggggcacu uucugcucuc uggugaaagu  60
gccgccaucu uuugagguguu accgcuugag aagacucaac c                    101

<210> SEQ ID NO 309
<211> LENGTH: 102
<212> TYPE: RNA
<213> ORGANISM: Homo sapiens

<400> SEQUENCE: 309
cgaggagcuc auacugggau acucaaaaug ggggcgcuuu ccuuuuuguc uguuacuggg  60
aagugcuucg auuuuggggu gucccuguuu gaguagggca uc                    102

<210> SEQ ID NO 310
<211> LENGTH: 22
<212> TYPE: RNA
<213> ORGANISM: Homo sapiens

<400> SEQUENCE: 310
ugagguagua gguuguauag uu                                          22

<210> SEQ ID NO 311
<211> LENGTH: 22
<212> TYPE: RNA
<213> ORGANISM: Homo sapiens

<400> SEQUENCE: 311
ugagguagua gguugugugg uu                                          22

<210> SEQ ID NO 312
<211> LENGTH: 22
<212> TYPE: RNA
<213> ORGANISM: Homo sapiens

<400> SEQUENCE: 312
ugagguagua gguuguaugg uu                                          22

<210> SEQ ID NO 313
<211> LENGTH: 21
<212> TYPE: RNA
<213> ORGANISM: Homo sapiens

<400> SEQUENCE: 313
agagguagua gguugcauag u                                           21

<210> SEQ ID NO 314
<211> LENGTH: 21
<212> TYPE: RNA
<213> ORGANISM: Homo sapiens

<400> SEQUENCE: 314
ugagguagga gguuguauag u                                           21

<210> SEQ ID NO 315
<211> LENGTH: 22
<212> TYPE: RNA
```

<213> ORGANISM: Homo sapiens

<400> SEQUENCE: 315
ugagguagua gauuguauag uu                                    22

<210> SEQ ID NO 316
<211> LENGTH: 21
<212> TYPE: RNA
<213> ORGANISM: Homo sapiens

<400> SEQUENCE: 316
ugagguagua guuuguacag u                                     21

<210> SEQ ID NO 317
<211> LENGTH: 19
<212> TYPE: RNA
<213> ORGANISM: Homo sapiens

<400> SEQUENCE: 317
ugagguagua guuugugcu                                        19

<210> SEQ ID NO 318
<211> LENGTH: 21
<212> TYPE: RNA
<213> ORGANISM: Homo sapiens

<400> SEQUENCE: 318
uggaauguaa agaaguaugu a                                     21

<210> SEQ ID NO 319
<211> LENGTH: 21
<212> TYPE: RNA
<213> ORGANISM: Homo sapiens

<400> SEQUENCE: 319
uggaagacua gugauuuugu u                                     21

<210> SEQ ID NO 320
<211> LENGTH: 23
<212> TYPE: RNA
<213> ORGANISM: Homo sapiens

<400> SEQUENCE: 320
ucuuugguua ucuagcugua uga                                   23

<210> SEQ ID NO 321
<211> LENGTH: 21
<212> TYPE: RNA
<213> ORGANISM: Homo sapiens

<400> SEQUENCE: 321
uaaagcuaga uaaccgaaag u                                     21

<210> SEQ ID NO 322
<211> LENGTH: 23
<212> TYPE: RNA
<213> ORGANISM: Homo sapiens

<400> SEQUENCE: 322
uacccuguag auccgaauuu gug                                   23

<210> SEQ ID NO 323
<211> LENGTH: 22
<212> TYPE: RNA

<213> ORGANISM: Homo sapiens

<400> SEQUENCE: 323
uacccuguag aaccgaauuu gu    22

<210> SEQ ID NO 324
<211> LENGTH: 22
<212> TYPE: RNA
<213> ORGANISM: Homo sapiens

<400> SEQUENCE: 324
uagcagcaca uaaugguuug ug    22

<210> SEQ ID NO 325
<211> LENGTH: 22
<212> TYPE: RNA
<213> ORGANISM: Homo sapiens

<400> SEQUENCE: 325
uagcagcaca ucaugguuua ca    22

<210> SEQ ID NO 326
<211> LENGTH: 22
<212> TYPE: RNA
<213> ORGANISM: Homo sapiens

<400> SEQUENCE: 326
uagcagcacg uaaauauugg cg    22

<210> SEQ ID NO 327
<211> LENGTH: 24
<212> TYPE: RNA
<213> ORGANISM: Homo sapiens

<400> SEQUENCE: 327
caaagugcuu acagugcagg uagu    24

<210> SEQ ID NO 328
<211> LENGTH: 20
<212> TYPE: RNA
<213> ORGANISM: Homo sapiens

<400> SEQUENCE: 328
acugcaguga aggcacuugu    20

<210> SEQ ID NO 329
<211> LENGTH: 22
<212> TYPE: RNA
<213> ORGANISM: Homo sapiens

<400> SEQUENCE: 329
uaaggugcau cuagugcaga ua    22

<210> SEQ ID NO 330
<211> LENGTH: 23
<212> TYPE: RNA
<213> ORGANISM: Homo sapiens

<400> SEQUENCE: 330
ugugcaaauc uaugcaaaac uga    23

<210> SEQ ID NO 331
<211> LENGTH: 23
<212> TYPE: RNA

<213> ORGANISM: Homo sapiens

<400> SEQUENCE: 331
ugugcaaauc caugcaaaac uga                                    23

<210> SEQ ID NO 332
<211> LENGTH: 22
<212> TYPE: RNA
<213> ORGANISM: Homo sapiens

<400> SEQUENCE: 332
uaaagugcuu auagugcagg ua                                     22

<210> SEQ ID NO 333
<211> LENGTH: 22
<212> TYPE: RNA
<213> ORGANISM: Homo sapiens

<400> SEQUENCE: 333
uagcuuauca gacugauguu ga                                     22

<210> SEQ ID NO 334
<211> LENGTH: 22
<212> TYPE: RNA
<213> ORGANISM: Homo sapiens

<400> SEQUENCE: 334
aagcugccag uugaagaacu gu                                     22

<210> SEQ ID NO 335
<211> LENGTH: 21
<212> TYPE: RNA
<213> ORGANISM: Homo sapiens

<400> SEQUENCE: 335
aucacauugc cagggauuuc c                                      21

<210> SEQ ID NO 336
<211> LENGTH: 23
<212> TYPE: RNA
<213> ORGANISM: Homo sapiens

<400> SEQUENCE: 336
aucacauugc cagggauuac cac                                    23

<210> SEQ ID NO 337
<211> LENGTH: 22
<212> TYPE: RNA
<213> ORGANISM: Homo sapiens

<400> SEQUENCE: 337
uggcucaguu cagcaggaac ag                                     22

<210> SEQ ID NO 338
<211> LENGTH: 22
<212> TYPE: RNA
<213> ORGANISM: Homo sapiens

<400> SEQUENCE: 338
cauugcacuu gucucggucu ga                                     22

<210> SEQ ID NO 339
<211> LENGTH: 22
<212> TYPE: RNA

<213> ORGANISM: Homo sapiens

<400> SEQUENCE: 339
uucaaguaau ccaggauagg cu                                              22

<210> SEQ ID NO 340
<211> LENGTH: 21
<212> TYPE: RNA
<213> ORGANISM: Homo sapiens

<400> SEQUENCE: 340
uucaaguaau ucaggauagg u                                               21

<210> SEQ ID NO 341
<211> LENGTH: 22
<212> TYPE: RNA
<213> ORGANISM: Homo sapiens

<400> SEQUENCE: 341
uucacagugg cuaaguuccg cc                                              22

<210> SEQ ID NO 342
<211> LENGTH: 20
<212> TYPE: RNA
<213> ORGANISM: Homo sapiens

<400> SEQUENCE: 342
uucacagugg cuaaguucug                                                 20

<210> SEQ ID NO 343
<211> LENGTH: 22
<212> TYPE: RNA
<213> ORGANISM: Homo sapiens

<400> SEQUENCE: 343
aaggagcuca cagucuauug ag                                              22

<210> SEQ ID NO 344
<211> LENGTH: 22
<212> TYPE: RNA
<213> ORGANISM: Homo sapiens

<400> SEQUENCE: 344
cuagcaccau cugaaaucgg uu                                              22

<210> SEQ ID NO 345
<211> LENGTH: 20
<212> TYPE: RNA
<213> ORGANISM: Homo sapiens

<400> SEQUENCE: 345
uagcaccauu ugaaaucagu                                                 20

<210> SEQ ID NO 346
<211> LENGTH: 22
<212> TYPE: RNA
<213> ORGANISM: Homo sapiens

<400> SEQUENCE: 346
uagcaccauu ugaaaucggu ua                                              22

<210> SEQ ID NO 347
<211> LENGTH: 23
<212> TYPE: RNA

<213> ORGANISM: Homo sapiens

<400> SEQUENCE: 347
uguaaacauc cucgacugga agc					23

<210> SEQ ID NO 348
<211> LENGTH: 22
<212> TYPE: RNA
<213> ORGANISM: Homo sapiens

<400> SEQUENCE: 348
cuuucagucg gauguuugca gc					22

<210> SEQ ID NO 349
<211> LENGTH: 21
<212> TYPE: RNA
<213> ORGANISM: Homo sapiens

<400> SEQUENCE: 349
uguaaacauc cuacacucag c					21

<210> SEQ ID NO 350
<211> LENGTH: 23
<212> TYPE: RNA
<213> ORGANISM: Homo sapiens

<400> SEQUENCE: 350
uguaaacauc cuacacucuc agc					23

<210> SEQ ID NO 351
<211> LENGTH: 22
<212> TYPE: RNA
<213> ORGANISM: Homo sapiens

<400> SEQUENCE: 351
uguaaacauc cccgacugga ag					22

<210> SEQ ID NO 352
<211> LENGTH: 20
<212> TYPE: RNA
<213> ORGANISM: Homo sapiens

<400> SEQUENCE: 352
uguaaacauc cuugacugga					20

<210> SEQ ID NO 353
<211> LENGTH: 21
<212> TYPE: RNA
<213> ORGANISM: Homo sapiens

<400> SEQUENCE: 353
ggcaagaugc uggcauagcu g					21

<210> SEQ ID NO 354
<211> LENGTH: 21
<212> TYPE: RNA
<213> ORGANISM: Homo sapiens

<400> SEQUENCE: 354
uauugcacau uacuaaguug c					21

<210> SEQ ID NO 355
<211> LENGTH: 19
<212> TYPE: RNA

<213> ORGANISM: Homo sapiens

<400> SEQUENCE: 355
gugcauugua guugcauug                                    19

<210> SEQ ID NO 356
<211> LENGTH: 22
<212> TYPE: RNA
<213> ORGANISM: Homo sapiens

<400> SEQUENCE: 356
uggcaguguc uuagcugguu gu                                22

<210> SEQ ID NO 357
<211> LENGTH: 22
<212> TYPE: RNA
<213> ORGANISM: Homo sapiens

<400> SEQUENCE: 357
aggcaguguc auuagcugau ug                                22

<210> SEQ ID NO 358
<211> LENGTH: 22
<212> TYPE: RNA
<213> ORGANISM: Homo sapiens

<400> SEQUENCE: 358
aggcagugua guuagcugau ug                                22

<210> SEQ ID NO 359
<211> LENGTH: 22
<212> TYPE: RNA
<213> ORGANISM: Homo sapiens

<400> SEQUENCE: 359
uauugcacuu gucccggccu gu                                22

<210> SEQ ID NO 360
<211> LENGTH: 22
<212> TYPE: RNA
<213> ORGANISM: Homo sapiens

<400> SEQUENCE: 360
aaagugcugu ucgugcaggu ag                                22

<210> SEQ ID NO 361
<211> LENGTH: 22
<212> TYPE: RNA
<213> ORGANISM: Homo sapiens

<400> SEQUENCE: 361
uucaacgggu auuuauugag ca                                22

<210> SEQ ID NO 362
<211> LENGTH: 22
<212> TYPE: RNA
<213> ORGANISM: Homo sapiens

<400> SEQUENCE: 362
uuuggcacua gcacauuuuu gc                                22

<210> SEQ ID NO 363
<211> LENGTH: 22
<212> TYPE: RNA

```
<213> ORGANISM: Homo sapiens

<400> SEQUENCE: 363
ugagguagua aguuguauug uu                                          22

<210> SEQ ID NO 364
<211> LENGTH: 22
<212> TYPE: RNA
<213> ORGANISM: Homo sapiens

<400> SEQUENCE: 364
aacccguaga uccgaucuug ug                                          22

<210> SEQ ID NO 365
<211> LENGTH: 22
<212> TYPE: RNA
<213> ORGANISM: Homo sapiens

<400> SEQUENCE: 365
cacccguaga accgaccuug cg                                          22

<210> SEQ ID NO 366
<211> LENGTH: 22
<212> TYPE: RNA
<213> ORGANISM: Homo sapiens

<400> SEQUENCE: 366
uacaguacug ugauaacuga ag                                          22

<210> SEQ ID NO 367
<211> LENGTH: 22
<212> TYPE: RNA
<213> ORGANISM: Homo sapiens

<400> SEQUENCE: 367
uacaguacug ugauaacuga ag                                          22

<210> SEQ ID NO 368
<211> LENGTH: 23
<212> TYPE: RNA
<213> ORGANISM: Homo sapiens

<400> SEQUENCE: 368
agcagcauug uacagggcua uga                                         23

<210> SEQ ID NO 369
<211> LENGTH: 20
<212> TYPE: RNA
<213> ORGANISM: Homo sapiens

<400> SEQUENCE: 369
ucaaaugcuc agacuccugu                                             20

<210> SEQ ID NO 370
<211> LENGTH: 24
<212> TYPE: RNA
<213> ORGANISM: Homo sapiens

<400> SEQUENCE: 370
aaaagugcuu acagugcagg uagc                                        24

<210> SEQ ID NO 371
<211> LENGTH: 21
<212> TYPE: RNA
```

<213> ORGANISM: Homo sapiens

<400> SEQUENCE: 371
uaaagugcug acagugcaga u                                          21

<210> SEQ ID NO 372
<211> LENGTH: 23
<212> TYPE: RNA
<213> ORGANISM: Homo sapiens

<400> SEQUENCE: 372
agcagcauug uacagggcua uca                                        23

<210> SEQ ID NO 373
<211> LENGTH: 23
<212> TYPE: RNA
<213> ORGANISM: Homo sapiens

<400> SEQUENCE: 373
uggaguguga caauggguguu ugu                                       23

<210> SEQ ID NO 374
<211> LENGTH: 22
<212> TYPE: RNA
<213> ORGANISM: Homo sapiens

<400> SEQUENCE: 374
uuaaggcacg cggugaaugc ca                                         22

<210> SEQ ID NO 375
<211> LENGTH: 23
<212> TYPE: RNA
<213> ORGANISM: Homo sapiens

<400> SEQUENCE: 375
ucccugagac ccuuuaaccu gug                                        23

<210> SEQ ID NO 376
<211> LENGTH: 22
<212> TYPE: RNA
<213> ORGANISM: Homo sapiens

<400> SEQUENCE: 376
ucccugagac ccuaacuugu ga                                         22

<210> SEQ ID NO 377
<211> LENGTH: 21
<212> TYPE: RNA
<213> ORGANISM: Homo sapiens

<400> SEQUENCE: 377
cauuauuacu uuugguacgc g                                          21

<210> SEQ ID NO 378
<211> LENGTH: 21
<212> TYPE: RNA
<213> ORGANISM: Homo sapiens

<400> SEQUENCE: 378
ucguaccgug aguaauaaug c                                          21

<210> SEQ ID NO 379
<211> LENGTH: 22
<212> TYPE: RNA

<213> ORGANISM: Homo sapiens

<400> SEQUENCE: 379
ucggauccgu cugagcuugg cu                                        22

<210> SEQ ID NO 380
<211> LENGTH: 22
<212> TYPE: RNA
<213> ORGANISM: Homo sapiens

<400> SEQUENCE: 380
ucacagugaa ccggucucuu uu                                        22

<210> SEQ ID NO 381
<211> LENGTH: 22
<212> TYPE: RNA
<213> ORGANISM: Homo sapiens

<400> SEQUENCE: 381
ucacagugaa ccggucucuu uc                                        22

<210> SEQ ID NO 382
<211> LENGTH: 21
<212> TYPE: RNA
<213> ORGANISM: Homo sapiens

<400> SEQUENCE: 382
cuuuuugcgg ucugggcuug c                                         21

<210> SEQ ID NO 383
<211> LENGTH: 20
<212> TYPE: RNA
<213> ORGANISM: Homo sapiens

<400> SEQUENCE: 383
cagugcaaug uuaaaagggc                                           20

<210> SEQ ID NO 384
<211> LENGTH: 22
<212> TYPE: RNA
<213> ORGANISM: Homo sapiens

<400> SEQUENCE: 384
cagugcaaug augaaagggc au                                        22

<210> SEQ ID NO 385
<211> LENGTH: 22
<212> TYPE: RNA
<213> ORGANISM: Homo sapiens

<400> SEQUENCE: 385
uaacagucua cagccauggu cg                                        22

<210> SEQ ID NO 386
<211> LENGTH: 22
<212> TYPE: RNA
<213> ORGANISM: Homo sapiens

<400> SEQUENCE: 386
uugguccccu ucaaccagcu gu                                        22

<210> SEQ ID NO 387
<211> LENGTH: 21
<212> TYPE: RNA

<213> ORGANISM: Homo sapiens

<400> SEQUENCE: 387 uuggucccu ucaaccagcu a                                      21

<210> SEQ ID NO 388
<211> LENGTH: 21
<212> TYPE: RNA
<213> ORGANISM: Homo sapiens

<400> SEQUENCE: 388
ugugacuggu ugaccagagg g                                     21

<210> SEQ ID NO 389
<211> LENGTH: 23
<212> TYPE: RNA
<213> ORGANISM: Homo sapiens

<400> SEQUENCE: 389
uauggcuuuu uauuccuaug uga                                   23

<210> SEQ ID NO 390
<211> LENGTH: 22
<212> TYPE: RNA
<213> ORGANISM: Homo sapiens

<400> SEQUENCE: 390
uauggcuuuu cauuccuaug ug                                    22

<210> SEQ ID NO 391
<211> LENGTH: 23
<212> TYPE: RNA
<213> ORGANISM: Homo sapiens

<400> SEQUENCE: 391
acuccauuug uuuugaugau gga                                   23

<210> SEQ ID NO 392
<211> LENGTH: 22
<212> TYPE: RNA
<213> ORGANISM: Homo sapiens

<400> SEQUENCE: 392
uauugcuuaa gaauacgcgu ag                                    22

<210> SEQ ID NO 393
<211> LENGTH: 17
<212> TYPE: RNA
<213> ORGANISM: Homo sapiens

<400> SEQUENCE: 393
agcugguguu gugaauc                                          17

<210> SEQ ID NO 394
<211> LENGTH: 18
<212> TYPE: RNA
<213> ORGANISM: Homo sapiens

<400> SEQUENCE: 394
ucuacagugc acgugucu                                         18

<210> SEQ ID NO 395
<211> LENGTH: 21
<212> TYPE: RNA

```
<213> ORGANISM: Homo sapiens

<400> SEQUENCE: 395
agugguuuua cccuauggua g                                            21

<210> SEQ ID NO 396
<211> LENGTH: 21
<212> TYPE: RNA
<213> ORGANISM: Homo sapiens

<400> SEQUENCE: 396
aacacugucu gguaaagaug g                                            21

<210> SEQ ID NO 397
<211> LENGTH: 23
<212> TYPE: RNA
<213> ORGANISM: Homo sapiens

<400> SEQUENCE: 397
uguaguguuu ccuacuuuau gga                                          23

<210> SEQ ID NO 398
<211> LENGTH: 20
<212> TYPE: RNA
<213> ORGANISM: Homo sapiens

<400> SEQUENCE: 398
cauaaaguag aaagcacuac                                              20

<210> SEQ ID NO 399
<211> LENGTH: 22
<212> TYPE: RNA
<213> ORGANISM: Homo sapiens

<400> SEQUENCE: 399
ugagaugaag cacguagcu ca                                            22

<210> SEQ ID NO 400
<211> LENGTH: 22
<212> TYPE: RNA
<213> ORGANISM: Homo sapiens

<400> SEQUENCE: 400
uacaguauag augauguacu ag                                           22

<210> SEQ ID NO 401
<211> LENGTH: 24
<212> TYPE: RNA
<213> ORGANISM: Homo sapiens

<400> SEQUENCE: 401
guccaguuuu cccaggaauc ccuu                                         24

<210> SEQ ID NO 402
<211> LENGTH: 22
<212> TYPE: RNA
<213> ORGANISM: Homo sapiens

<400> SEQUENCE: 402
ugagaacuga auuccauggg uu                                           22

<210> SEQ ID NO 403
<211> LENGTH: 20
<212> TYPE: RNA
```

```
<213> ORGANISM: Homo sapiens

<400> SEQUENCE: 403
guguguggaa augcuucugc                                                   20

<210> SEQ ID NO 404
<211> LENGTH: 22
<212> TYPE: RNA
<213> ORGANISM: Homo sapiens

<400> SEQUENCE: 404
ucagugcacu acagaacuuu gu                                                22

<210> SEQ ID NO 405
<211> LENGTH: 22
<212> TYPE: RNA
<213> ORGANISM: Homo sapiens

<400> SEQUENCE: 405
ucagugcauc acagaacuuu gu                                                22

<210> SEQ ID NO 406
<211> LENGTH: 22
<212> TYPE: RNA
<213> ORGANISM: Homo sapiens

<400> SEQUENCE: 406
ucuggcuccg ugucuucacu cc                                                22

<210> SEQ ID NO 407
<211> LENGTH: 22
<212> TYPE: RNA
<213> ORGANISM: Homo sapiens

<400> SEQUENCE: 407
ucucccaacc cuuguaccag ug                                                22

<210> SEQ ID NO 408
<211> LENGTH: 22
<212> TYPE: RNA
<213> ORGANISM: Homo sapiens

<400> SEQUENCE: 408
acuagacuga agcuccuuga gg                                                22

<210> SEQ ID NO 409
<211> LENGTH: 21
<212> TYPE: RNA
<213> ORGANISM: Homo sapiens

<400> SEQUENCE: 409
ucagugcaug acagaacuug g                                                 21

<210> SEQ ID NO 410
<211> LENGTH: 20
<212> TYPE: RNA
<213> ORGANISM: Homo sapiens

<400> SEQUENCE: 410
uugcauaguc acaaaaguga                                                   20

<210> SEQ ID NO 411
<211> LENGTH: 22
<212> TYPE: RNA
```

<213> ORGANISM: Homo sapiens

<400> SEQUENCE: 411
uagguuaucc guguugccuu cg                                              22

<210> SEQ ID NO 412
<211> LENGTH: 22
<212> TYPE: RNA
<213> ORGANISM: Homo sapiens

<400> SEQUENCE: 412
aaucauacac gguugaccua uu                                              22

<210> SEQ ID NO 413
<211> LENGTH: 22
<212> TYPE: RNA
<213> ORGANISM: Homo sapiens

<400> SEQUENCE: 413
uuaaugcuaa ucgugauagg gg                                              22

<210> SEQ ID NO 414
<211> LENGTH: 23
<212> TYPE: RNA
<213> ORGANISM: Homo sapiens

<400> SEQUENCE: 414
aacauucaac gcugucggug agu                                             23

<210> SEQ ID NO 415
<211> LENGTH: 24
<212> TYPE: RNA
<213> ORGANISM: Homo sapiens

<400> SEQUENCE: 415
aacauucauu gcugucggug gguu                                            24

<210> SEQ ID NO 416
<211> LENGTH: 22
<212> TYPE: RNA
<213> ORGANISM: Homo sapiens

<400> SEQUENCE: 416
aacauucaac cugucgguga gu                                              22

<210> SEQ ID NO 417
<211> LENGTH: 22
<212> TYPE: RNA
<213> ORGANISM: Homo sapiens

<400> SEQUENCE: 417
uuuggcaaug guagaacuca ca                                              22

<210> SEQ ID NO 418
<211> LENGTH: 21
<212> TYPE: RNA
<213> ORGANISM: Homo sapiens

<400> SEQUENCE: 418
ugguucuaga cuugccaacu a                                               21

<210> SEQ ID NO 419
<211> LENGTH: 23
<212> TYPE: RNA

<213> ORGANISM: Homo sapiens

<400> SEQUENCE: 419
uauggcacug guagaauuca cug                                        23

<210> SEQ ID NO 420
<211> LENGTH: 22
<212> TYPE: RNA
<213> ORGANISM: Homo sapiens

<400> SEQUENCE: 420
uggacggaga acugauaagg gu                                         22

<210> SEQ ID NO 421
<211> LENGTH: 18
<212> TYPE: RNA
<213> ORGANISM: Homo sapiens

<400> SEQUENCE: 421
uggagagaaa ggcaguuc                                              18

<210> SEQ ID NO 422
<211> LENGTH: 23
<212> TYPE: RNA
<213> ORGANISM: Homo sapiens

<400> SEQUENCE: 422
caaagaauuc uccuuuuggg cuu                                        23

<210> SEQ ID NO 423
<211> LENGTH: 21
<212> TYPE: RNA
<213> ORGANISM: Homo sapiens

<400> SEQUENCE: 423
ucgugucuug uguugcagcc g                                          21

<210> SEQ ID NO 424
<211> LENGTH: 22
<212> TYPE: RNA
<213> ORGANISM: Homo sapiens

<400> SEQUENCE: 424
caucccuugc augguggagg gu                                         22

<210> SEQ ID NO 425
<211> LENGTH: 23
<212> TYPE: RNA
<213> ORGANISM: Homo sapiens

<400> SEQUENCE: 425
gugccuacug agcugauauc agu                                        23

<210> SEQ ID NO 426
<211> LENGTH: 22
<212> TYPE: RNA
<213> ORGANISM: Homo sapiens

<400> SEQUENCE: 426
ugauauguuu gauauauuag gu                                         22

<210> SEQ ID NO 427
<211> LENGTH: 22
<212> TYPE: RNA

<213> ORGANISM: Homo sapiens

<400> SEQUENCE: 427
caacggaauc ccaaaagcag cu                                        22

<210> SEQ ID NO 428
<211> LENGTH: 21
<212> TYPE: RNA
<213> ORGANISM: Homo sapiens

<400> SEQUENCE: 428
cugaccuaug aauugacagc c                                         21

<210> SEQ ID NO 429
<211> LENGTH: 21
<212> TYPE: RNA
<213> ORGANISM: Homo sapiens

<400> SEQUENCE: 429
aacuggccua caaaguccca g                                         21

<210> SEQ ID NO 430
<211> LENGTH: 22
<212> TYPE: RNA
<213> ORGANISM: Homo sapiens

<400> SEQUENCE: 430
uguaacagca acuccaugug ga                                        22

<210> SEQ ID NO 431
<211> LENGTH: 21
<212> TYPE: RNA
<213> ORGANISM: Homo sapiens

<400> SEQUENCE: 431
uagcagcaca gaaauauugg c                                         21

<210> SEQ ID NO 432
<211> LENGTH: 21
<212> TYPE: RNA
<213> ORGANISM: Homo sapiens

<400> SEQUENCE: 432
uagguaguuu cauguuguug g                                         21

<210> SEQ ID NO 433
<211> LENGTH: 21
<212> TYPE: RNA
<213> ORGANISM: Homo sapiens

<400> SEQUENCE: 433
uagguaguuu ccuguuguug g                                         21

<210> SEQ ID NO 434
<211> LENGTH: 22
<212> TYPE: RNA
<213> ORGANISM: Homo sapiens

<400> SEQUENCE: 434
uucaccaccu ucuccaccca gc                                        22

<210> SEQ ID NO 435
<211> LENGTH: 19
<212> TYPE: RNA

```
<213> ORGANISM: Homo sapiens

<400> SEQUENCE: 435
gguccagagg ggagauagg                                              19

<210> SEQ ID NO 436
<211> LENGTH: 23
<212> TYPE: RNA
<213> ORGANISM: Homo sapiens

<400> SEQUENCE: 436
cccaguguuc agacuaccug uuc                                         23

<210> SEQ ID NO 437
<211> LENGTH: 22
<212> TYPE: RNA
<213> ORGANISM: Homo sapiens

<400> SEQUENCE: 437
uacaguaguc ugcacauugg uu                                          22

<210> SEQ ID NO 438
<211> LENGTH: 23
<212> TYPE: RNA
<213> ORGANISM: Homo sapiens

<400> SEQUENCE: 438
cccaguguuu agacuaucug uuc                                         23

<210> SEQ ID NO 439
<211> LENGTH: 22
<212> TYPE: RNA
<213> ORGANISM: Homo sapiens

<400> SEQUENCE: 439
uaacacuguc ugguaacgau gu                                          22

<210> SEQ ID NO 440
<211> LENGTH: 24
<212> TYPE: RNA
<213> ORGANISM: Homo sapiens

<400> SEQUENCE: 440
cucuaauacu gccugguaau gaug                                        24

<210> SEQ ID NO 441
<211> LENGTH: 22
<212> TYPE: RNA
<213> ORGANISM: Homo sapiens

<400> SEQUENCE: 441
aauacugccg gguaaugaug ga                                          22

<210> SEQ ID NO 442
<211> LENGTH: 22
<212> TYPE: RNA
<213> ORGANISM: Homo sapiens

<400> SEQUENCE: 442
agagguauag ggcaugggaa ga                                          22

<210> SEQ ID NO 443
<211> LENGTH: 22
<212> TYPE: RNA
```

<213> ORGANISM: Homo sapiens

<400> SEQUENCE: 443
gugaaauguu uaggaccacu ag                                              22

<210> SEQ ID NO 444
<211> LENGTH: 22
<212> TYPE: RNA
<213> ORGANISM: Homo sapiens

<400> SEQUENCE: 444
uucccuuugu cauccuaugc cu                                              22

<210> SEQ ID NO 445
<211> LENGTH: 22
<212> TYPE: RNA
<213> ORGANISM: Homo sapiens

<400> SEQUENCE: 445
uccuucauuc caccggaguc ug                                              22

<210> SEQ ID NO 446
<211> LENGTH: 22
<212> TYPE: RNA
<213> ORGANISM: Homo sapiens

<400> SEQUENCE: 446
uggaauguaa ggaagugugu gg                                              22

<210> SEQ ID NO 447
<211> LENGTH: 22
<212> TYPE: RNA
<213> ORGANISM: Homo sapiens

<400> SEQUENCE: 447
auaagacgag caaaaagcuu gu                                              22

<210> SEQ ID NO 448
<211> LENGTH: 21
<212> TYPE: RNA
<213> ORGANISM: Homo sapiens

<400> SEQUENCE: 448
cugugcgugu gacagcggcu g                                               21

<210> SEQ ID NO 449
<211> LENGTH: 22
<212> TYPE: RNA
<213> ORGANISM: Homo sapiens

<400> SEQUENCE: 449
uucccuuugu cauccuucgc cu                                              22

<210> SEQ ID NO 450
<211> LENGTH: 21
<212> TYPE: RNA
<213> ORGANISM: Homo sapiens

<400> SEQUENCE: 450
uaacagucuc cagucacggc c                                               21

<210> SEQ ID NO 451
<211> LENGTH: 22
<212> TYPE: RNA

<213> ORGANISM: Homo sapiens

<400> SEQUENCE: 451
accaucgacc guugauugua cc                                    22

<210> SEQ ID NO 452
<211> LENGTH: 21
<212> TYPE: RNA
<213> ORGANISM: Homo sapiens

<400> SEQUENCE: 452
acagcaggca cagacaggca g                                     21

<210> SEQ ID NO 453
<211> LENGTH: 21
<212> TYPE: RNA
<213> ORGANISM: Homo sapiens

<400> SEQUENCE: 453
augaccuaug aauugacaga c                                     21

<210> SEQ ID NO 454
<211> LENGTH: 21
<212> TYPE: RNA
<213> ORGANISM: Homo sapiens

<400> SEQUENCE: 454
uaaucucagc uggcaacugu g                                     21

<210> SEQ ID NO 455
<211> LENGTH: 24
<212> TYPE: RNA
<213> ORGANISM: Homo sapiens

<400> SEQUENCE: 455
uacugcauca ggaacugauu ggau                                  24

<210> SEQ ID NO 456
<211> LENGTH: 21
<212> TYPE: RNA
<213> ORGANISM: Homo sapiens

<400> SEQUENCE: 456
uugugcuuga ucuaaccaug u                                     21

<210> SEQ ID NO 457
<211> LENGTH: 21
<212> TYPE: RNA
<213> ORGANISM: Homo sapiens

<400> SEQUENCE: 457
ugauugucca aacgcaauuc u                                     21

<210> SEQ ID NO 458
<211> LENGTH: 21
<212> TYPE: RNA
<213> ORGANISM: Homo sapiens

<400> SEQUENCE: 458
ccacaccgua ucugacacuu u                                     21

<210> SEQ ID NO 459
<211> LENGTH: 23
<212> TYPE: RNA

<213> ORGANISM: Homo sapiens

<400> SEQUENCE: 459
agcuacauug ucugcugggu uuc         23

<210> SEQ ID NO 460
<211> LENGTH: 24
<212> TYPE: RNA
<213> ORGANISM: Homo sapiens

<400> SEQUENCE: 460
agcuacaucu ggcuacuggg ucuc        24

<210> SEQ ID NO 461
<211> LENGTH: 21
<212> TYPE: RNA
<213> ORGANISM: Homo sapiens

<400> SEQUENCE: 461
ugucaguuug ucaaauaccc c           21

<210> SEQ ID NO 462
<211> LENGTH: 23
<212> TYPE: RNA
<213> ORGANISM: Homo sapiens

<400> SEQUENCE: 462
caagucacua gugguuccgu uua         23

<210> SEQ ID NO 463
<211> LENGTH: 21
<212> TYPE: RNA
<213> ORGANISM: Homo sapiens

<400> SEQUENCE: 463
agggcccccc cucaauccug u           21

<210> SEQ ID NO 464
<211> LENGTH: 22
<212> TYPE: RNA
<213> ORGANISM: Homo sapiens

<400> SEQUENCE: 464
ugguuuaccg ucccacauac au          22

<210> SEQ ID NO 465
<211> LENGTH: 23
<212> TYPE: RNA
<213> ORGANISM: Homo sapiens

<400> SEQUENCE: 465
cagugcaaua guauugucaa agc         23

<210> SEQ ID NO 466
<211> LENGTH: 23
<212> TYPE: RNA
<213> ORGANISM: Homo sapiens

<400> SEQUENCE: 466
uaagugcuuc cauguuuugg uga         23

<210> SEQ ID NO 467
<211> LENGTH: 23
<212> TYPE: RNA

<213> ORGANISM: Homo sapiens

<400> SEQUENCE: 467
acuuuaacau ggaagugcuu ucu                    23

<210> SEQ ID NO 468
<211> LENGTH: 23
<212> TYPE: RNA
<213> ORGANISM: Homo sapiens

<400> SEQUENCE: 468
uaagugcuuc cauguuuuag uag                    23

<210> SEQ ID NO 469
<211> LENGTH: 22
<212> TYPE: RNA
<213> ORGANISM: Homo sapiens

<400> SEQUENCE: 469
uuuaacaugg ggguaccugc ug                     22

<210> SEQ ID NO 470
<211> LENGTH: 23
<212> TYPE: RNA
<213> ORGANISM: Homo sapiens

<400> SEQUENCE: 470
uaagugcuuc cauguuucag ugg                    23

<210> SEQ ID NO 471
<211> LENGTH: 23
<212> TYPE: RNA
<213> ORGANISM: Homo sapiens

<400> SEQUENCE: 471
uaagugcuuc cauguuugag ugu                    23

<210> SEQ ID NO 472
<211> LENGTH: 23
<212> TYPE: RNA
<213> ORGANISM: Homo sapiens

<400> SEQUENCE: 472
aaaagcuggg uugagagggc gaa                    23

<210> SEQ ID NO 473
<211> LENGTH: 21
<212> TYPE: RNA
<213> ORGANISM: Homo sapiens

<400> SEQUENCE: 473
uaagccaggg auuguggguu c                      21

<210> SEQ ID NO 474
<211> LENGTH: 22
<212> TYPE: RNA
<213> ORGANISM: Homo sapiens

<400> SEQUENCE: 474
gcacauuaca cggucgaccu cu                     22

<210> SEQ ID NO 475
<211> LENGTH: 23
<212> TYPE: RNA

<213> ORGANISM: Homo sapiens

<400> SEQUENCE: 475 cgcaucccu agggcauugg ugu         23

<210> SEQ ID NO 476
<211> LENGTH: 22
<212> TYPE: RNA
<213> ORGANISM: Homo sapiens

<400> SEQUENCE: 476
ccacugcccc aggugcugcu gg         22

<210> SEQ ID NO 477
<211> LENGTH: 21
<212> TYPE: RNA
<213> ORGANISM: Homo sapiens

<400> SEQUENCE: 477
ccuaguaggu guccaguaag u          21

<210> SEQ ID NO 478
<211> LENGTH: 20
<212> TYPE: RNA
<213> ORGANISM: Homo sapiens

<400> SEQUENCE: 478
ccucugggcc cuuccuccag            20

<210> SEQ ID NO 479
<211> LENGTH: 22
<212> TYPE: RNA
<213> ORGANISM: Homo sapiens

<400> SEQUENCE: 479
cuggcccucu cugcccuucc gu         22

<210> SEQ ID NO 480
<211> LENGTH: 23
<212> TYPE: RNA
<213> ORGANISM: Homo sapiens

<400> SEQUENCE: 480
gcaaagcaca cggccugcag aga        23

<210> SEQ ID NO 481
<211> LENGTH: 21
<212> TYPE: RNA
<213> ORGANISM: Homo sapiens

<400> SEQUENCE: 481
gccccugggc cuauccuaga a          21

<210> SEQ ID NO 482
<211> LENGTH: 23
<212> TYPE: RNA
<213> ORGANISM: Homo sapiens

<400> SEQUENCE: 482
ucaagagcaa uaacgaaaaa ugu        23

<210> SEQ ID NO 483
<211> LENGTH: 23
<212> TYPE: RNA

<213> ORGANISM: Homo sapiens

<400> SEQUENCE: 483
uccagcuccu auaugaugcc uuu        23

<210> SEQ ID NO 484
<211> LENGTH: 23
<212> TYPE: RNA
<213> ORGANISM: Homo sapiens

<400> SEQUENCE: 484
uccagcauca gugauuuugu uga        23

<210> SEQ ID NO 485
<211> LENGTH: 21
<212> TYPE: RNA
<213> ORGANISM: Homo sapiens

<400> SEQUENCE: 485
ucccuguccu ccaggagcuc a        21

<210> SEQ ID NO 486
<211> LENGTH: 23
<212> TYPE: RNA
<213> ORGANISM: Homo sapiens

<400> SEQUENCE: 486
uccgucucag uuacuuuaua gcc        23

<210> SEQ ID NO 487
<211> LENGTH: 24
<212> TYPE: RNA
<213> ORGANISM: Homo sapiens

<400> SEQUENCE: 487
ucucacacag aaaucgcacc cguc        24

<210> SEQ ID NO 488
<211> LENGTH: 21
<212> TYPE: RNA
<213> ORGANISM: Homo sapiens

<400> SEQUENCE: 488
ugcugacucc uaguccaggg c        21

<210> SEQ ID NO 489
<211> LENGTH: 23
<212> TYPE: RNA
<213> ORGANISM: Homo sapiens

<400> SEQUENCE: 489
ugucugcccg caugccugcc ucu        23

<210> SEQ ID NO 490
<211> LENGTH: 22
<212> TYPE: RNA
<213> ORGANISM: Homo sapiens

<400> SEQUENCE: 490
aauugcacuu uagcaauggu ga        22

<210> SEQ ID NO 491
<211> LENGTH: 22
<212> TYPE: RNA

<213> ORGANISM: Homo sapiens

<400> SEQUENCE: 491
acauagagga aauuccacgu uu                                    22

<210> SEQ ID NO 492
<211> LENGTH: 21
<212> TYPE: RNA
<213> ORGANISM: Homo sapiens

<400> SEQUENCE: 492
aauaauacau gguugaucuu u                                     21

<210> SEQ ID NO 493
<211> LENGTH: 21
<212> TYPE: RNA
<213> ORGANISM: Homo sapiens

<400> SEQUENCE: 493
gccugcuggg guggaaccug g                                     21

<210> SEQ ID NO 494
<211> LENGTH: 21
<212> TYPE: RNA
<213> ORGANISM: Homo sapiens

<400> SEQUENCE: 494
gugccgccau cuuuugagug u                                     21

<210> SEQ ID NO 495
<211> LENGTH: 23
<212> TYPE: RNA
<213> ORGANISM: Homo sapiens

<400> SEQUENCE: 495
aaagugcugc gacauuugag cgu                                   23

<210> SEQ ID NO 496
<211> LENGTH: 22
<212> TYPE: RNA
<213> ORGANISM: Homo sapiens

<400> SEQUENCE: 496
acucaaaaug ggggcgcuuu cc                                    22

<210> SEQ ID NO 497
<211> LENGTH: 23
<212> TYPE: RNA
<213> ORGANISM: Homo sapiens

<400> SEQUENCE: 497
gaagugcuuc gauuuugggg ugu                                   23

<210> SEQ ID NO 498
<211> LENGTH: 22
<212> TYPE: RNA
<213> ORGANISM: Homo sapiens

<400> SEQUENCE: 498
uuauaauaca accugauaag ug                                    22

<210> SEQ ID NO 499
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 499
aactttgtct tgggggacac                                                  20

<210> SEQ ID NO 500
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 500
gaggggagga tctgttttcc                                                  20

<210> SEQ ID NO 501
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 501
ccaggagctc aggaagaaga gat                                              23

<210> SEQ ID NO 502
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 502
ccctctgagg catctgattg ggttt                                            25

<210> SEQ ID NO 503
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 503
gcatctagag caccccagag gagtgt                                           26

<210> SEQ ID NO 504
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 504
gcatctagac aagcaccatg cggttc                                           26

<210> SEQ ID NO 505
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 505
tactctagac caggagctca ggaaga                                          26

<210> SEQ ID NO 506
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 506
mcattctaga tgaggcatct gattggg                                         27

<210> SEQ ID NO 507
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507
cuagaaaugu uuagguuacu aaaacagggu g                                    31
```

MICRORNA FINGERPRINTS DURING HUMAN MEGAKARYOCYTOPOIESIS

CROSS-REFERENCE TO RELATED APPLICATIONS

This application is a divisional application of U.S. patent application Ser. No. 13/169,184, having a 371 filing date of Jun. 27, 2011, now allowed, which claims priority to parent U.S. patent application Ser. No. 12/293,472, having a 371 filing date of Oct. 9, 2008, now U.S. Pat. No. 7,895,584 issued Jul. 26, 2011, which is a national stage application filed under 37 CFR§1.371 of international application PCT/US2007/006824 filed Mar. 19, 2007, which claims priority to U.S. Provisional Application Ser. No. 61/743,585 filed Mar. 20, 2006, the entire disclosures of which are expressly incorporated herein by reference.

STATEMENT REGARDING FEDERALLY SPONSORED RESEARCH

The invention was supported, in whole or in part, by National Institutes of Health Program Project Grants PO1CA76259, PO1CA16058, PO1CA81534 and P01CA16672. The Government has certain rights in the invention.

BACKGROUND OF THE INVENTION

MicroRNAs (miRNAs) are a small non-coding family of 19-25 nucleotide RNAs that regulate gene expression by targeting messenger RNAs (mRNA) in a sequence specific manner, inducing translational repression or mRNA degradation depending on the degree of complementarity between miRNAs and their targets (Bartel, D. P. (2004) *Cell* 116, 281-297; Ambros, V. (2004) *Nature* 431, 350-355). Many miRNAs are conserved in sequence between distantly related organisms, suggesting that these molecules participate in essential processes. Indeed, miRNAs are involved in the regulation of gene expression during development (Xu, P., et al. (2003) *Curr. Biol.* 13, 790-795), cell proliferation (Xu, P., et al. (2003) *Curr. Biol.* 13, 790-795), apoptosis (Cheng, A. M., et al. (2005) *Nucl. Acids Res.* 33, 1290-1297), glucose metabolism (Poy, M. N., et al. (2004) *Nature* 432, 226-230), stress resistance (Dresios, J., et al. (2005) *Proc. Natl. Acad. Sci. USA* 102, 1865-1870) and cancer (Calin, G. A, et al. (2002) *Proc. Natl. Acad. Sci. USA* 99, 1554-15529; Calin, G. A., et al. (2004) *Proc. Natl. Acad. Sci. USA* 101, 11755-11760; Ile, L., et al. (2005) *Nature* 435, 828-833; and Lu, J., et al. (2005) *Nature* 435:834-838).

There is also strong evidence that miRNAs play a role in mammalian hematopoiesis. In mice, miR-181, miR-223 and miR-142 are differentially expressed in hematopoietic tissues, and their expression is regulated during hematopoiesis and lineage commitment (Chen, C. Z., et al. (2004) *Science* 303, 83-86). The ectopic expression of miR-181 in murine hematopoietic progenitor cells led to proliferation in the B-cell compartment (Chen, C. Z., et al. (2004) *Science* 303, 83-86). Systematic miRNA gene profiling in cells of the murine hematopoietic system revealed different miRNA expression patterns in the hematopoietic system compared with neuronal tissues, and identified individual miRNA expression changes that occur during cell differentiation (Monticelli, S., et al. (2005) *Genome Biology* 6, R71). A recent study has identified down-modulation of miR-221 and miR-222 in human erythropoietic cultures of CD34+ cord blood progenitor cells (Felli, N., et al. (2005) *Proc. Natl. Acad. Sci. USA*. 102, 18081-18086). These miRNAs were found to target the oncogene c-Kit. Further functional studies indicated that the decline of these two miRNAs in erythropoietic cultures unblocks Kit protein production at the translational level leading to expansion of early erythroid cells (Felli, N., et al. (2005) *Proc. Natl. Acad. Sci. USA*. 102, 18081-18086). In line with the hypothesis of miRNAs regulating cell differentiation, miR-223 was found to be a key member of a regulatory circuit involving C/EBPa and NFI-A, which controls granulocytic differentiation in all-trans retinoic acid-treated acute promyelocytic leukemic cell lines (Fazi, F., et al. (2005) *Cell* 123, 819-831).

miRNAs have also been found deregulated in hematopoietic malignancies. Indeed, the first report linking miRNAs and cancer involved the deletion and down regulation of the miR-15a and miR-16-1 cluster, located at chromosome 13q14.3, a commonly-deleted region in chronic lymphocytic leukemia (Calin, G. A, et al. (2002) *Proc. Natl. Acad. Sci. USA* 99, 1554-15529). High expression of miR-155 and host gene BIC was also reported in B-cell lymphomas (Metzler M., et al. (2004) *Genes Chromosomes and Cancer* 39; 167-169). More recently it was shown that the miR-17-92 cluster, which is located in a genomic region of amplification in lymphomas, is overexpressed in human B-cell lymphomas and the enforced expression of this cluster acted in concert with c-MYC expression to accelerate tumor development in a mouse B cell lymphoma model (He, L., et al. (2005) *Nature* 435, 828-833). These observations indicate that miRNAs are important regulators of hematopoiesis and can be involved in malignant transformation.

Platelets play an essential role in hemostasis and thrombosis. They are produced from in large numbers from their parent cells, bone marrow megakaryocytes, and arise from fragmentation of the cytoplasm. Only recently has the molecular basis of what may turn out to be a large family of related disorders affecting platelet production started to be defined. If the level of circulating platelets drops below a certain number (thrombocytopenia), the patient runs the risk of catastrophic hemorrhage. Patients with cancer who have received chemotherapy or bone marrow transplants usually have thrombocytopenia, and the slow recovery of platelet count in these patients has been a concern. The demand for platelet units for transfusion has been steadily increasing primarily because of the need to maintain a certain platelet level in such patients with cancer or those undergoing major cardiac surgery.

Identification of microRNAs that are differentially-expressed in cancer cells (e.g., leukemia cells) may help pinpoint specific miRNAs that are involved in cancer and other disorders (e.g., platelet disorders). Furthermore, the identification of putative targets of these miRNAs may help to unravel their pathogenic role. In particular, discovering the patterns and sequence of miRNA expression during hematopoietic differentiation may provide insights about the functional roles of these tiny non-coding genes in normal and malignant hematopoiesis.

There is a need for novel methods and compositions for the diagnosis, prognosis and treatment of cancer, myeloproliferative disorders and platelet disorders (e.g., inherited platelet disorders).

SUMMARY OF THE INVENTION

The present invention is based, in part, on the identification of specific miRNAs that are involved in megakaryocytic differentiation and/or have altered expression levels in cancerous cells (e.g., in acute megakaryoblastic leukemia (AMKL cell lines)). In the present study, the miRNA gene expression in human megakaryocyte cultures from bone marrow CD34+ progenitors and acute megakaryoblastic leukemia cell lines was investigated. The results of this analysis indicate that several miRNAs are downregulated during normal megakaryocytic differentiation. The results further demonstrate that these miRNAs target genes involved in megakaryocytopoiesis, while others are over expressed in cancer cells.

Accordingly, the invention encompasses methods of diagnosing or prognosticating cancer and/or a myeloproliferative disorder in a subject (e.g., a human). According to the methods of the invention, the level of at least one miR gene product in a test sample from the subject is compared to the level of a corresponding miR gene product in a control sample. An alteration (e.g., an increase, a decrease) in the level of the miR gene product in the test sample, relative to the level of a corresponding miR gene product in the control sample, is indicative of the subject either having, or being at risk for developing, cancer and/or a myeloproliferative disorder. In one embodiment, the level of the miR gene product in the test sample from the subject is greater than that of the control. In another embodiment, the at least one miR gene product is selected from the group consisting of miR-101, miR-126, miR-99a, miR-99-prec, miR-106, miR-339, miR-99b, miR-149, miR-33, miR-135 and miR-20. In still another embodiment, the at least one miR gene product is selected from the group consisting of miR-101, miR-126, miR-106, miR-20 and miR-135. In yet another embodiment, the at least one miR gene product is selected from the group consisting of miR-106, miR-20 and miR-135. In particular embodiments, the cancer that is diagnosed or prognosticated is a leukemia (e.g., acute myeloid leukemia (e.g., acute megakaryoblastic leukemia)) or multiple myeloma. In other embodiments, the myeloproliferative disorder is selected from the group consisting of essential thrombocytemia (ET), polycythemia vera (PV), myelodisplasia, myelofibrosis (e.g., agnogenic myeloid metaplasia (AMM) (also referred to as idiopathic myelofibrosis)) and chronic myelogenous leukemia (CML).

In another embodiment, the invention is a method of treating a cancer and/or a myeloproliferative disorder in a subject (e.g., a human). In the method, an effective amount of a compound for inhibiting expression of at least one miR gene product selected from the group consisting of miR-101, miR-126, miR-99a, miR-99-prec, miR-106, miR-339, miR-99b, miR-149, miR-33, miR-135 and miR-20 is administered to the subject. In one embodiment, the compound for inhibiting expression of at least one miR gene product inhibits expression of a miR gene product selected from the group consisting of miR-101, miR-126, miR-106, miR-20 and miR-135. In another embodiment, the compound for inhibiting expression of at least one miR gene product inhibits expression of a miR gene product selected from the group consisting of miR-106, miR-20 and miR-135. In particular embodiments, the cancer that is treated is a leukemia (e.g., acute myeloid leukemia (e.g., acute megakaryoblastic leukemia)) or multiple myeloma. In other embodiments, the myeloproliferative disorder is selected from the group consisting of essential thrombocytemia (ET), polycythemia vera (PV), myelodisplasia, myelofibrosis (e.g., agnogenic myeloid metaplasia (AMM)) and chronic myelogenous leukemia (CML).

In another embodiment, the invention is a method of treating a cancer and/or a myeloproliferative disorder associated with overexpression of a MAFB gene product in a subject (e.g., a human). In the method, an effective amount of at least one miR gene product or a variant or biologically-active fragment thereof, which binds to, and decreases expression of, the MAFB gene product, is administered to the subject. In one embodiment, the at least one miR gene product, variant or biologically-active fragment thereof comprises a nucleotide sequence that is complementary to a nucleotide sequence in the MAFB gene product. In another embodiment, the at least one miR gene product is miR-130a or a variant or biologically-active fragment thereof. Cancers and myeloproliferative disorders suitable for treatment using this method include, for example, those described herein.

In another embodiment, the invention is a method of treating a cancer and/or a myeloproliferative disorder associated with overexpression of a HOXA1 gene product in a subject (e.g., a human). In the method, an effective amount of at least one miR gene product or a variant or biologically-active fragment thereof, which binds to, and decreases expression of, the HOXA1 gene product, is administered to the subject. In one embodiment, the at least one miR gene product, variant or biologically-active fragment thereof comprises a nucleotide sequence that is complementary to a nucleotide sequence in the HOXA1 gene product. In another embodiment, the at least one miR gene product is miR-10a or a variant or biologically-active fragment thereof. Cancers and myeloproliferative disorders suitable for treatment using this method include, for example, those described herein.

In one embodiment, the invention is a method of determining and/or predicting megakaryocytic differentiation. In this method, the level of at least one miR gene product in a sample (e.g., a sample from a subject (e.g., a human)) comprising megakaryocyte progeny and/or megakaryocytes is determined. That level is compared to the level of the corresponding miR gene product in a control. An alteration in the level of the at least one miR gene product in the sample, relative to that of the control, is indicative of megakaryocytic differentiation. In one embodiment, the alteration is a decrease in the level of the at least one miR gene product in the sample. In another embodiment, the at least one miR gene product is selected from the group consisting of miR-10a, miR-126, miR-106, miR-010b, miR-130a, miR-130a-prec, miR-124a, miR-032-prec, miR-101, miR-30c, miR-213, miR-132-prec, miR-150, miR-020, miR-339, let-7a, let-7d, miR-181c, miR-181b and miR-017. In still another embodiment, the at least one miR gene product is selected from the group consisting of miR-10a, miR-10b, miR-30c, miR-106, miR-126, miR-130a, miR-132, and miR-143.

The invention further provides pharmaceutical compositions for treating cancer and/or a myeloproliferative disorder. In one embodiment, the pharmaceutical compositions of the invention comprise at least one miR expression-inhibition compound and a pharmaceutically-acceptable carrier. In a particular embodiment, the at least one miR expression-inhibition compound is specific for a miR gene product whose expression is greater in cancer cells (e.g., acute megakaryoblastic leukemia (AMKL) cells) than control cells (i.e., it is upregulated). In one embodiment, the miR expression-inhibition compound is specific for one or more miR gene products selected from the group consisting of miR-101, miR-126, miR-99a, miR-99-prec, miR-106, miR-339, miR-99b, miR-149, miR-33, miR-135 and miR-20. In another embodiment, the miR expression-inhibition compound is specific for one or more miR gene products selected from the group consisting of miR-101, miR-126, miR-106, miR-20, and miR-135. In still another embodiment, the miR expression-inhibition compound is specific for one or more miR gene products selected from the group consisting of miR-106, miR-20 and miR-135. In yet another embodiment, the pharmaceutical composition further comprises at least one anti-cancer agent.

In one embodiment, the invention is a pharmaceutical composition for treating a cancer associated with overexpression of a MAFB gene product and/or a myeloproliferative disorder associated with overexpression of a MAFB gene product. Such pharmaceutical compositions comprise an effective amount of at least one miR gene product and a pharmaceutically-acceptable carrier, wherein the at least one miR gene product binds to, and decreases expression of, the MAFB gene product. In another embodiment, the at least one miR gene product comprises a nucleotide sequence that is complementary to a nucleotide sequence in the MAFB gene product. In still another embodiment, the at least one miR gene product is miR-130a or a variant or biologically-active fragment thereof. In yet another embodiment, the pharmaceutical composition further comprises at least one anti-cancer agent.

In one embodiment, the invention is a pharmaceutical composition for treating a cancer associated with overexpression of a HOXA1 gene product and/or a myeloproliferative disorder associated with overexpression of a HOXA1 gene product. Such pharmaceutical compositions comprise an effective amount of at least one miR gene product and a pharmaceutically-acceptable carrier, wherein the at least one miR gene product binds to, and decreases expression of, the HOXA1 gene product. In another embodiment, the at least one miR gene product comprises a nucleotide sequence that is complementary to a nucleotide sequence in the HOXA1 gene product. In still another embodiment, the at least one miR gene product is miR-10a or a variant or biologically-active fragment thereof. In yet another embodiment, the pharmaceutical composition further comprises at least one anti-cancer agent.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A depicts Northern Blots for miR-130a, miR-10a and miR-223. A loading RNA control was performed with U6.

FIG. 1B is a graph depicting RT-miRNA-PCR for miR-10a, miR-106, miR-126 and miR-130a. miRNA expression is presented as fold difference with respect to CD34$^+$ cells before culture.

FIG. 1C is a graph depicting temporal expression of miR-223 by microarray.

FIG. 1D is a graph depicting temporal expression of miR-15-1 and miR-16-1 by RT-miRNA PCR.

FIGS. 2A-2C demonstrate that MAFB is a target of miR-130a.

FIG. 2A depicts MAFB mRNA and protein expression data in CD34$^+$ progenitors induced to megakaryocytic differentiation. β-Actin was used for RT-PCR and Western blot loading controls.

FIG. 2B is a graph depicting relative repression of luciferase activity in MEG01 cells co-transfected with miR-10a and PGL3 3'UTR MAFB, miR-10a with PGL3 3'UTR, miR-10a seed match mutated and scramble with mutated, and wild type 3'UTR MAFB.

FIG. 2C depicts Western blots of MAFB total protein lysates in K562 cells transfected with miR-130a and scramble.

FIG. 3A is a graph depicting RT-PCR results for HOXA1 gene expression in differentiated megakaryocytes (Relative amount of transcript with respect to CD34$^+$ progenitors at baseline).

FIG. 3B is a Western blot showing hoxa1 protein expression in differentiated megakaryocytes.

FIG. 3C is a graph depicting relative repression of luciferase activity of HOXA1 3' UTR cloned PGL3 reporter plasmid when co-transfected with miR-10a and control scramble.

FIG. 3D is a schematic showing complementarity between miR-10a (SEQ ID NO: 322) and the HOXA1 3'UTR (SEQ ID NO: 507) as predicted by PICTAR.

FIG. 3E depicts RT-PCR results for miR-10a gene expression in scramble and miR-10a precursor transfected K562 cells.

FIG. 3F depicts RT-PCR results for HOXA1 gene expression in scramble and miR-10a precursor transfected K562 cells.

FIG. 3G is a Western blot showing HOXA1 expression in K562 cells transfected with control scramble and precursor miR-10a.

FIG. 4A depicts May-Giemsa stains that were performed on cytospin preparations from CD34$^+$ progenitors in culture at different days of culture (day 6, day 10, day 12 and day 14). At day 4, most of the cells were immature, as evidenced by the high nucleous:cytoplasmic ratio. Larger and multinuclear cells were observed by day 10. At day 14, predominantly larger, polyploid cells with long cytoplasmic processes and numerous membrane blebs with invaginations and vacuoles (original magnification 400×) were observed.

FIG. 4B depicts FACS analysis of CD34 in vitro-differentiated megakaryocytes. The membrane phenotype of CD34$^+$ progenitor cells that are grown in culture is shown. Cells were harvested at days 10 (D+10), 14 (D+14) and 16 (D+16) and were analyzed by single fluorescent labeling using an anti-CD41 antibody, an anti-CD61a antibody, an anti-CD42a antibody, an anti-CD61a antibody and their respective isotype monoclonal antibodies (D+10 isotype; D+14 isotype; D+16 isotype). Double labeling was performed with anti-CD41a and CD61b monoclonal Abs at day 14 only.

DETAILED DESCRIPTION OF THE PREFERRED EMBODIMENT

Figure 1A:
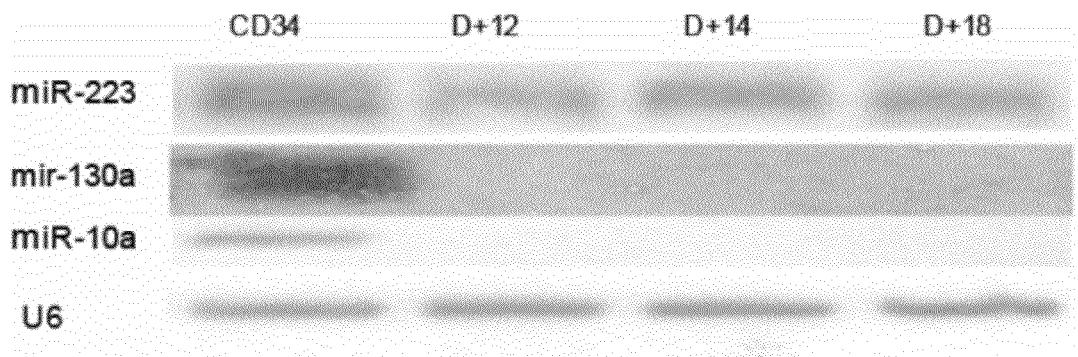
FIGS. 1A-1D depict Northern Blots and Real Time miRNA-PCR results, which validate microRNA chip data in CD34 progenitor differentiation experiments.
Figure 1B:
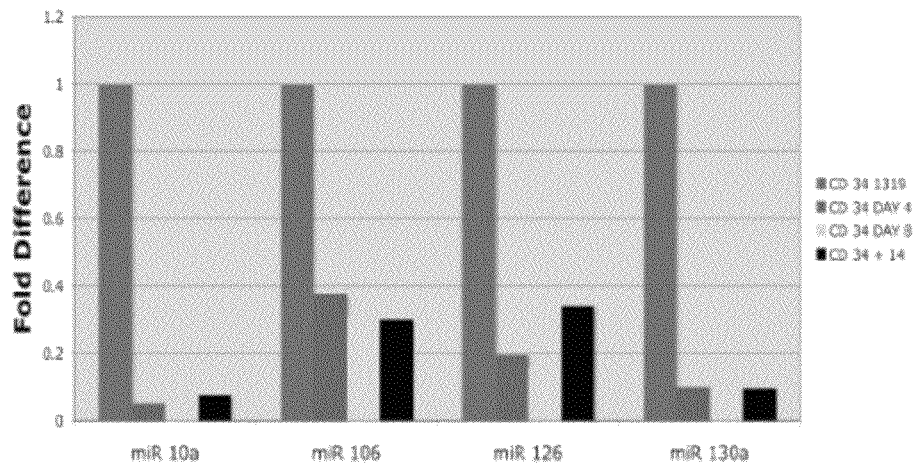

The present invention is based, in part, on the identification of specific microRNAs (miRNAs) that are involved in megakaryocytic differentiation and/or have altered expression levels in cancerous cells (e.g., in acute megakaryoblastic leukemia (AMKL cell lines)). The invention is further based, in part, on association of these miRNAs with particular diagnostic, prognostic and therapeutic features. As described and exemplified herein:

i) particular miRNA are downregulated during megakaryocytic differentiation;

ii) the transcription factor MAFB is a target for miR-130a;

iii) miR-10a expression parallels that of HOXB gene expression;

iv) miR-10a downregulates HOXA1 expression; and v) particular miRNA are upregulated in cancerous cells (e.g., acute megakaryoblastic leukemia (AMKL) cells).

As used herein interchangeably, a "miR gene product," "microRNA," "miR," "miR" or "miRNA" refers to the unprocessed or processed RNA transcript from a miR gene. As the miR gene products are not translated into protein, the term "miR gene products" does not include proteins. The unprocessed miR gene transcript is also called a "miR precursor," and typically comprises an RNA transcript of about 70-100 nucleotides in length. The miR precursor can be processed by digestion with an RNAse (for example, Dicer, Argonaut, RNAse III (e.g., *E. coli* RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having to be processed from the miR precursor. When a microRNA is referred to herein by name, the name corresponds to both the precursor and mature forms, unless otherwise indicated.

Tables 1a and 1b depict the nucleotide sequences of particular precursor and mature human microRNAs.

TABLE 1a

Human microRNA Precursor Sequences.

| Precursor Name | Sequence (5' To 3')* | SEQ ID NO. |
|---|---|---|
| let-7a-1 | CACUGUGGGAUGAGGUAGUAGGUUGUAUAGUUUUAGGG UCACACCCACCACUGGGAGAUAACUAUACAAUCUACUGU CUUUCCUAACGUG | 1 |
| let-7a-2 | AGGUUGAGGUAGUAGGUUGUAUAGUUUAGAAUUACAUC AAGGGAGAUAACUGUACAGCCUCCUAGCUUUCCU | 2 |
| let-7a-3 | GGGUGAGGUAGUAGGUUGUAUAGUUUGGGCUCUGCCC UGCUAUGGGAUAACUAUACAAUCUACUGUCUUUCCU | 3 |
| let-7a-4 | GUGACUGCAUGCUCCCAGGUUGAGGUAGUAGGUUGUAU AGUUUAGAAUUACACAAGGGAGAUAACUGUACAGCCUC CUAGCUUUCCUUGGGUCUUGCACUAAACAAC | 4 |
| let-7b | GGCGGGGUGAGGUAGUAGGUUGUGUGGUUUCAGGGCAG UGAUGUUGCCCCUCGGAAGAUAACUAUACAACCUACUGC CUUCCCUG | 5 |
| let-7c | GCAUCCGGGUUGAGGUAGUAGGUUGUAUGGUUUAGAGU UACACCCUGGGAGUUAACUGUACAACCUUCUAGCUUUCC UUGGAGC | 6 |
| let-7d | CCUAGGAAGAGGUAGUAGGUUGCAUAGUUUUAGGGCAG GGAUUUUGCCCACAAGGAGGUAACUAUACGACCUGCUGC CUUUCUUAGG | 7 |
| let-7d-v1 | CUAGGAAGAGGUAGUAGUUUGCAUAGUUUUAGGGCAAA GAUUUUGCCCCACAAGUAGUUAGCUAUACGACCUGCAGCC UUUUGUAG | 8 |
| let-7d-v2 | CUGGCUGAGGUAGUAGUUUGUGCUGUUGGUCGGGUUGU GACAUUGCCCGCUGUGGAGAUAACUGCGCAAGCUACUGC CUUGCUAG | 9 |

TABLE 1a-continued

Human microRNA Precursor Sequences.

| Precursor Name | Sequence (5' To 3')* | SEQ ID NO. |
|---|---|---|
| let-7e | CCCGGGCUGAGGUAGGAGGUUGUAUAGUUGAGGAGGAC ACCCAAGGAGAUCACUAUACGGCCUCCUAGCUUUCCCCA GG | 10 |
| let-7f-1 | UCAGAGUGAGGUAGUAGAUUGUAUAGUUGUGGGGUAGU GAUUUUACCCUGUUCAGGAGAUAACUAUACAAUCUAUU GCCUUCCCUGA | 11 |
| let-7f-2-1 | CUGUGGGAUGAGGUAGUAGAUUGUAUAGUUGUGGGGUA GUGAUUUUACCCUGUUCAGGAGAUAACUAUACAAUCUA UUGCCUUCCCUGA | 12 |
| let-7f-2-2 | CUGUGGGAUGAGGUAGUAGAUUGUAUAGUUUUAGGGUC AUACCCCAUCUUGGAGAUAACUAUACAGUCUACUGUCUU UCCCACGG | 13 |
| let-7g | UUGCCUGAUUCCAGGCUGAGGUAGUAGUUUGUACAGUU UGAGGGUCUAUGAUACCACCCGGUACAGGAGAUAACUG UACAGGCCACUGCCUUGCCAGGAACAGCGCGC | 14 |
| let-7i | CUGGCUGAGGUAGUAGUUUGUGCUGUUGGUCGGGUUGU GACAUUGCCCGCUGUGGAGAUAACUGCGCAAGCUACUGC CUUGCUAG | 15 |
| miR-1b-1-1 | ACCUACUCAGAGUACAUACUUCUUUAUGUACCCAUAUGA ACAUACAAUGCUAUGGAAUGUAAAGAAGUAUGUAUUUU UGGUAGGC | 16 |
| miR-1b-1-2 | CAGCUAACAACUUAGUAAUACCUACUCAGAGUACAUACU UCUUUAUGUACCCAUAUGAACAUACAAUGCUAUGGAAU GUAAAGAAGUAUGUAUUUUUGGUAGGCAAUA | 17 |
| miR-1b-2 | GCCUGCUUGGGAAACAUACUUCUUUAUAUGCCCAUAUG GACCUGCUAAGCUAUGGAAUGUAAAGAAGUAUGUAUCU CAGGCCGGG | 18 |
| miR-1b | UGGGAAACAUACUUCUUUAUAUGCCCAUAUGGACCUGC UAAGCUAUGGAAUGUAAAGAAGUAUGUAUCUCA | 19 |
| miR-1d | ACCUACUCAGAGUACAUACUUCUUUAUGUACCCAUAUGA ACAUACAAUGCUAUGGAAUGUAAAGAAGUAUGUAUUUU UGGUAGGC | 20 |
| miR-7-1a | UGGAUGUUGGCCUAGUUCUGUGUGGAAGACUAGUGAUU UUGUUGUUUUUAGAUAACUAAAUCGACAACAAAUCACA GUCUGCCAUAUGGCACAGGCCAUGCCUCUACA | 21 |
| miR-7-1b | UUGGAUGUUGGCCUAGUUCUGUGUGGAAGACUAGUGAU UUUGUUGUUUUUAGAUAACUAAAUCGACAACAAAUCAC AGUCUGCCAUAUGGCACAGGCCAUGCCUCUACAG | 22 |
| miR-7-2 | CUGGAUACAGAGUGGACCGGCUGGCCCCAUCUGGAAGAC UAGUGAUUUUGUUGUUGUCUUACUGCGCUCAACAACAA AUCCCAGUCUACCUAAUGGUGCCAGCCAUCGCA | 23 |
| miR-7-3 | AGAUUAGAGUGGCUGUGGUCUAGUGCUGUGUGGAAGAC UAGUGAUUUUGUUGUUCUGAUGUACUACGACAACAAGU CACAGCCGGCCUCAUAGCGCAGACUCCCUUCGAC | 24 |
| miR-9-1 | CGGGGUUGGUUGUUAUCUUUGGUUAUCUAGCUGUAUGA GUGGUGUGGAGUCUUCAUAAAGCUAGAUAACCGAAAGU AAAAAUAACCCCA | 25 |
| miR-9-2 | GGAAGCGAGUUGUUAUCUUUGGUUAUCUAGCUGUAUGA GUGUAUUGGUCUUCAUAAAGCUAGAUAACCGAAAGUAA AAACUCCUUCA | 26 |
| miR-9-3 | GGAGGCCCGUUUCUCUCUUUGGUUAUCUAGCUGUAUGA GUGCCACAGAGCCGUCAUAAAGCUAGAUAACCGAAAGU AGAAAUGAUUCUCA | 27 |
| miR-10a | GAUCUGUCUGUCUUCUGUAUAUACCCUGUAGAUCCGAA UUUGUGUAAGGAAUUUUGUGGUCACAAAUUCGUAUCUA GGGGAAUAUGUAGUUGACAUAAACACUCCGCUCU | 28 |

TABLE 1a-continued

Human microRNA Precursor Sequences.

| Precursor Name | Sequence (5' To 3')* | SEQ ID NO. |
|---|---|---|
| miR-10b | CCAGAGGUUGUAACGUUGUCUAUAUAUACCCUGUAGAA CCGAAUUUGUGUGGUAUCCGUAUAGUCACAGAUUCGAU UCUAGGGGAAUAUAUGGUCGAUGCAAAAACUUCA | 29 |
| miR-15a-2 | GCGCGAAUGUGUGUUUAAAAAAAAUAAAACCUUGGAGU AAAGUAGCAGCACAUAAUGGUUUGUGGAUUUUGAAAAG GUGCAGGCCAUAUUGUGCUGCCUCAAAAAUAC | 30 |
| miR-15a | CCUUGGAGUAAAGUAGCAGCACAUAAUGGUUUGUGGAU UUUGAAAAGGUGCAGGCCAUAUUGUGCUGCCUCAAAAA UACAAGG | 31 |
| miR-15b-1 | CUGUAGCAGCACAUCAUGGUUUACAUGCUACAGUCAAG AUGCGAAUCAUUAUUUGCUGCUCUAG | 32 |
| miR-15b-2 | UUGAGGCCUUAAAGUACUGUAGCAGCACAUCAUGGUUU ACAUGCUACAGUCAAGAUGCGAAUCAUUAUUUGCUGCU CUAGAAAUUUAAGGAAAUUCAU | 33 |
| miR-16-1 | GUCAGCAGUGCCUUAGCAGCACGUAAAUAUUGGCGUUA AGAUUCUAAAAUUAUCUCCAGUAUUAACUGUGCUGCUG AAGUAAGGUUGAC | 34 |
| miR-16-2 | GUUCCACUCUAGCAGCACGUAAAUAUUGGCGUAGUGAA AUAUAUAUUAAACACCAAUAUUACUGUGCUGCUUUAGU GUGAC | 35 |
| miR-16-13 | GCAGUGCCUUAGCAGCACGUAAAUAUUGGCGUUAAGAU UCUAAAAUUAUCUCCAGUAUUAACUGUGCUGCUGAAGU AAGGU | 36 |
| miR-17 | GUCAGAAUAAUGUCAAAGUGCUUACAGUGCAGGUAGUG AUAUGUGCAUCUACUGCAGUGAAGGCACUUGUAGCAUU AUGGUGAC | 37 |
| miR-18 | UGUUCUAAGGUGCAUCUAGUGCAGAUAGUGAAGUAGAU UAGCAUCUACUGCCCUAAGUGCUCCUUCUGGCA | 38 |
| miR-18-13 | UUUUUGUUCUAAGGUGCAUCUAGUGCAGAUAGUGAAGU AGAUUAGCAUCUACUGCCCUAAGUGCUCCUUCUGGCAUA AGAA | 39 |
| miR-19a | GCAGUCCUCUGUUAGUUUUGCAUAGUUGCACUACAAGA AGAAUGUAGUUGUGCAAAUCUAUGCAAAACUGAUGGUG GCCUGC | 40 |
| miR-19a-13 | CAGUCCUCUGUUAGUUUUGCAUAGUUGCACUACAAGAA GAAUGUAGUUGUGCAAAUCUAUGCAAAACUGAUGGUGG CCUG | 41 |
| miR-19b-1 | CACUGUUCUAUGGUUAGUUUUGCAGGUUUGCAUCCAGC UGUGUGAUAUUCUGCUGUGCAAAUCCAUGCAAAACUGA CUGUGGUAGUG | 42 |
| miR-19b-2 | ACAUUGCUACUUACAAUUAGUUUUGCAGGUUUGCAUUU CAGCGUAUAUAUGUAUAUGUGGCUGUGCAAAUCCAUGC AAAACUGAUUGUGAUAAUGU | 43 |
| miR-19b-13 | UUCUAUGGUUAGUUUUGCAGGUUUGCAUCCAGCUGUGU GAUAUUCUGCUGUGCAAAUCCAUGCAAAACUGACUGUG GUAG | 44 |
| miR-19b-X | UUACAAUUAGUUUUGCAGGUUUGCAUUUCAGCGUAUAU AUGUAUAUGUGGCUGUGCAAAUCCAUGCAAAACUGAUU GUGAU | 45 |
| miR-20 (miR-20a) | GUAGCACUAAAGUGCUUAUAGUGCAGGUAGUGUUUAGU UAUCUACUGCAUUAUGAGCACUUAAAGUACUGC | 46 |
| miR-21 | UGUCGGGUAGCUUAUCAGACUGAUGUUGACUGUUGAAU CUCAUGGCAACACCAGUCGAUGGGCUGUCUGACA | 47 |

TABLE 1a-continued

Human microRNA Precursor Sequences.

| Precursor Name | Sequence (5' To 3')* | SEQ ID NO. |
|---|---|---|
| miR-21-17 | ACCUUGUCGGGUAGCUUAUCAGACUGAUGUUGACUGUU GAAUCUCAUGGCAACACCAGUCGAUGGGCUGUCUGACAU UUUG | 48 |
| miR-22 | GGCUGAGCCGCAGUAGUUCUUCAGUGGCAAGCUUUAUG UCCUGACCCAGCUAAAGCUGCCAGUUGAAGAACUGUUGC CCUCUGCC | 49 |
| miR-23a | GGCCGGCUGGGGUUCCUGGGGAUGGGAUUUGCUUCCUG UCACAAAUCACAUUGCCAGGGAUUUCCAACCGACC | 50 |
| miR-23b | CUCAGGUGCUCUGGCUGCUUGGGUUCCUGGCAUGCUGAU UUGUGACUUAAGAUUAAAAUCACAUUGCCAGGGAUUAC CACGCAACCACGACCUUGGC | 51 |
| miR-23-19 | CCACGGCCGGCUGGGGUUCCUGGGGAUGGGAUUUGCUUC CUGUCACAAAUCACAUUGCCAGGGAUUUCCAACCGACCC UGA | 52 |
| miR-24-1 | CUCCGGUGCCUACUGAGCUGAUAUCAGUUCUCAUUUUAC ACAUGGCUCAGUUCAGCAGGAACAGGAG | 53 |
| miR-24-2 | CUCUGCCUCCCGUGCCUACUGAGCUGAAACACAGUUGGU UUGUGUACACUGGCUCAGUUCAGCAGGAACAGGG | 54 |
| miR-24-19 | CCCUGGGCUCUGCCUCCCGUGCCUACUGAGCUGAAACAC AGUUGGUUUGUGUACACUGGCUCAGUUCAGCAGGAACA GGGG | 55 |
| miR-24-9 | CCCUCCGGUGCCUACUGAGCUGAUAUCAGUUCUCAUUUU ACACACUGGCUCAGUUCAGCAGGAACAGCAUC | 56 |
| miR-25 | GGCCAGUGUUGAGAGGCGGAGACUUGGGCAAUUGCUGG ACGCUGCCCUGGGCAUUGCACUUGUCUCGGUCUGACAGU GCCGGCC | 57 |
| miR-26a | AGGCCGUGGCCUCGUUCAAGUAAUCCAGGAUAGGCUGU GCAGGUCCCAAUGGGCCUAUCUUGGUUACUUGCACGGGGA CGCGGGCCU | 58 |
| miR-26a-1 | GUGGCCUCGUUCAAGUAAUCCAGGAUAGGCUGUGCAGG UCCCAAUGGGCCUAUUCUUGGUUACUUGCACGGGGACGC | 59 |
| miR-26a-2 | GGCUGUGGCUGGAUUCAAGUAAUCCAGGAUAGGCUGUU UCCAUCUGUGAGGCCUAUUCUUGAUUACUUGUUUCUGG AGGCAGCU | 60 |
| miR-26b | CCGGGACCCAGUUCAAGUAAUUCAGGAUAGGUUGUGUG CUGUCCAGCCUGUUCUCCAUUACUUGGCUCGGGGACCGG | 61 |
| miR-27a | CUGAGGAGCAGGGCUUAGCUGCUUGUGAGCAGGGUCCA CACCAAGUCGUGUUCACAGUGGCUAAGUUCCGCCCCCCA G | 62 |
| miR-27b-1 | AGGUGCAGAGCUUAGCUGAUUGGUGAACAGUGAUUGGU UUCCGCUUUGUUCACAGUGGCUAAGUUCUGCACCU | 63 |
| miR-27b-2 | ACCUCUCUAACAAGGUGCAGAGCUUAGCUGAUUGGUGA ACAGUGAUUGGUUUCCGCUUUGUUCACAGUGGCUAAGU UCUGCACCUGAAGAGAAGGUG | 64 |
| miR-27-19 | CCUGAGGAGCAGGGCUUAGCUGCUUGUGAGCAGGGUCC ACACCAAGUCGUGUUCACAGUGGCUAAGUUCCGCCCCCC AGG | 65 |
| miR-28 | GGUCCUUGCCCUCAAGGAGCUCACAGUCUAUUGAGUUAC CUUUCUGACUUUCCCACUAGAUUGUGAGCUCCUGGAGGG CAGGCACU | 66 |
| miR-29a-2 | CCUUCUGUGACCCCUUAGAGGAUGACUGAUUUCUUUUG GUGUUCAGAGUCAAUAUAAUUUCUAGCACCAUCUGAA AUCGGUUAUAAUGAUUGGGGAAGAGCACCAUG | 67 |

TABLE 1a-continued

Human microRNA Precursor Sequences.

| Precursor Name | Sequence (5' To 3')* | SEQ ID NO. |
|---|---|---|
| miR-29a | AUGACUGAUUUCUUUUGGUGUUCAGAGUCAAUAUAAUU UUCUAGCACCAUCUGAAAUCGGUUAU | 68 |
| miR-29b-1 | CUUCAGGAAGCUGGUUUCAUAUGGUGGUUUAGAUUUAA AUAGUGAUUGUCUAGCACCAUUUGAAAUCAGUGUUCUU GGGGG | 69 |
| miR-29b-2 | CUUCUGGAAGCUGGUUUCACAUGGUGGCUUAGAUUUUU CCAUCUUUGUAUCUAGCACCAUUUGAAAUCAGUGUUUU AGGAG | 70 |
| miR-29c | ACCACUGGCCCAUCUCUUACACAGGCUGACCGAUUUCUC CUGGUGUUCAGAGUCUGUUUUUGUCUAGCACCAUUUGA AAUCGGUUAUGAUGUAGGGGGAAAAGCAGCAGC | 71 |
| miR-30a | GCGACUGUAAACAUCCUCGACUGGAAGCUGUGAAGCCAC AGAUGGGCUUUCAGUCGGAUGUUUGCAGCUGC | 72 |
| miR-30b-1 | AUGUAAACAUCCUACACUCAGCUGUAAUACAUGGAUUG GCUGGGAGGUGGAUGUUUACGU | 73 |
| miR-30b-2 | ACCAAGUUUCAGUUCAUGUAAACAUCCUACACUCAGCUG UAAUACAUGGAUUGGCUGGGAGGUGGAUGUUUACUUCA GCUGACUUGGA | 74 |
| miR-30c | AGAUACUGUAAACAUCCUACACUCUCAGCUGUGGAAAG UAAGAAAGCUGGGAGAAGGCUGUUUACUCUUUCU | 75 |
| miR-30d | GUUGUUGUAAACAUCCCCGACUGGAAGCUGUAAGACAC AGCUAAGCUUUCAGUCAGAUGUUUGCUGCUAC | 76 |
| miR-30e | CUGUAAACAUCCUUGACUGGAAGCUGUAAGGUGUUCAG AGGAGCUUUCAGUCGGAUGUUUACAG | 77 |
| miR-31 | GGAGAGGAGGCAAGAUGCUGGCAUAGCUGUUGAACUGG GAACCUGCUAUGCCAACAUAUUGCCAUCUUUCC | 78 |
| miR-32 | GGAGAUAUUGCACAUUACUAAGUUGCAUGUUGUCACGG CCUCAAUGCAAUUUAGUGUGUGUGAUAUUUUC | 79 |
| miR-33b | GGGGGCCGAGAGAGGCGGGCGGCCCCGCGGUGCAUUGCU GUUGCAUUGCACGUGUGUGAGGCGGGUGCAGUGCCUCG GCAGUGCAGCCCGGAGCCGGCCCCUGGCACCAC | 80 |
| miR-33b-2 | ACCAAGUUUCAGUUCAUGUAAACAUCCUACACUCAGCUG UAAUACAUGGAUUGGCUGGGAGGUGGAUGUUUACUUCA GCUGACUUGGA | 81 |
| miR-33 | CUGUGGUGCAUUGUAGUUGCAUUGCAUGUUCUGGUGGU ACCCAUGCAAUGUUUCCACAGUGCAUCACAG | 82 |
| miR-34-a | GGCCAGCUGUGAGUGUUUCUUUGGCAGUGUCUUAGCUG GUUGUUGUGAGCAAUAGUAAGGAAGCAAUCAGCAAGUA UACUGCCCUAGAAGUGCUGCACGUUGUGGGGCCC | 83 |
| miR-34-b | GUGCUCGGUUUGUAGGCAGUGUCAUUAGCUGAUUGUAC UGUGGUGGUUACAAUCACUAACUCCACUGCCAUCAAAAC AAGGCAC | 84 |
| miR-34-c | AGUCUAGUUACUAGGCAGUGUAGUUAGCUGAUUGCUAA UAGUACCAAUCACUAACCACACGGCCAGGUAAAAGAUU | 85 |
| miR-91-13 | UCAGAAUAAUGUCAAAGUGCUUACAGUGCAGGUAGUGA UAUGUGCAUCUACUGCAGUGAAGGCACUUGUAGCAUUA UGGUGA | 86 |
| miR-92-1 | CUUUCUACACAGGUUGGGAUCGGUUGCAAUGCUGUGUU UCUGUAUGGUAUUGCACUUGUCCCGGCCUGUUGAGUUU GG | 87 |
| miR-92-2 | UCAUCCCUGGGUGGGGAUUUGUUGCAUUACUUGUGUUC UAUAUAAGUAUUGCACUUGUCCCGGCCUGUGGAAGA | 88 |

TABLE 1a-continued

Human microRNA Precursor Sequences.

| Precursor Name | Sequence (5' To 3')* | SEQ ID NO. |
|---|---|---|
| miR-93-1 (miR-93-2) | CUGGGGGCUCCAAAGUGCUGUUCGUGCAGGUAGUGUGA UUACCCAACCUACUGCUGAGCUAGCACUUCCCGAGCCCC CGG | 89 |
| miR-95-4 | AACACAGUGGGCACUCAAUAAAUGUCUGUUGAAUUGAA AUGCGUUACAUUCAACGGGUAUUUAUUGAGCACCCACUC UGUG | 90 |
| miR-96-7 | UGGCCGAUUUUGGCACUAGCACAUUUUUGCUUGUGUCU CUCCGCUCUGAGCAAUCAUGUGCAGUGCCAAUAUGGGAA A | 91 |
| miR-97-6 (miR-30*) | GUGAGCGACUGUAAACAUCCUCGACUGGAAGCUGUGAA GCCACAGAUGGGCUUUCAGUCGGAUGUUUGCAGCUGCCU ACU | 92 |
| miR-98 | GUGAGGUAGUAAGUUGUAUUGUUGUGGGGUAGGGAUAU UAGGCCCCAAUUAGAAGAUAACUAUACAACUUACUACU UUCC | 93 |
| miR-99b | GGCACCCACCCGUAGAACCGACCUUGCGGGGCCUUCGCC GCACACAAGCUCGUGUCUGUGGGUCCGUGUC | 94 |
| miR-99a | CCCAUUGGCAUAAACCCGUAGAUCCGAUCUUGUGGUGAA GUGGACCGCACAAGCUCGCUUCUAUGGGUCUGUGUCAGU GUG | 95 |
| miR-100-1/2 | AAGAGAGAAGAUAUUGAGGCCUGUUGCCACAAACCCGU AGAUCCGAACUUGUGGUAUUAGUCCGCACAAGCUUGUA UCUAUAGGUAUGUGUCUGUUAGGCAAUCUCAC | 96 |
| miR-100-11 | CCUGUUGCCACAAACCCGUAGAUCCGAACUUGUGGUAUU AGUCCGCACAAGCUUGUAUCUAUAGGUAUGUGUCUGUU AGG | 97 |
| miR-101-1/2 | AGGCUGCCCUGGCUCAGUUAUCACAGUGCUGAUGCUGUC UAUUCUAAAGGUACAGUACUGUGAUAACUGAAGGAUGG CAGCCAUCUUACCUUCCAUCAGAGGAGCCUCAC | 98 |
| miR-101 | UCAGUUAUCACAGUGCUGAUGCUGUCCAUUCUAAAGGU ACAGUACUGUGAUAACUGA | 99 |
| miR-101-1 | UGCCCUGGCUCAGUUAUCACAGUGCUGAUGCUGUCUAUU CUAAAGGUACAGUACUGUGAUAACUGAAGGAUGGCA | 100 |
| miR-101-2 | ACUGUCCUUUUUCGGUUAUCAUGGUACCGAUGCUGUAU AUCUGAAAGGUACAGUACUGUGAUAACUGAAGAAUGGU GGU | 101 |
| miR-101-9 | UGUCCUUUUUCGGUUAUCAUGGUACCGAUGCUGUAUAU CUGAAAGGUACAGUACUGUGAUAACUGAAGAAUGGUG | 102 |
| miR-102-1 | CUUCUGGAAGCUGGUUUCACAUGGUGGCUUAGAUUUUU CCAUCUUUGUAUCUAGCACCAUUUGAAAUCAGUGUUUU AGGAG | 103 |
| miR-102-7.1 (miR-102-7.2) | CUUCAGGAAGCUGGUUUCAUAUGGUGGUUUAGAUUUAA AUAGUGAUUGUCUAGCACCAUUUGAAAUCAGUGUUCUU GGGGG | 104 |
| miR-103-2 | UUGUGCUUUCAGCUUCUUUACAGUGCUGCCUUGUAGCA UUCAGGUCAAGCAACAUUGUACAGGGCUAUGAAAGAAC CA | 105 |
| miR-103-1 | UACUGCCCUCGGCUUCUUUACAGUGCUGCCUUGUUGCAU AUGGAUCAAGCAGCAUUGUACAGGGCUAUGAAGGCAUU G | 106 |
| miR-104-17 | AAAUGUCAGACAGCCCAUCGACUGGUGUUGCCAUGAGA UUCAACAGUCAACAUCAGUCUGAUAAGCUACCCGACAAG G | 107 |

TABLE 1a-continued

Human microRNA Precursor Sequences.

| Precursor Name | Sequence (5' To 3')* | SEQ ID NO. |
| --- | --- | --- |
| miR-105-1 | UGUGCAUCGUGGUCAAAUGCUCAGACUCCUGUGGUGGC UGCUCAUGCACCACGGAUGUUUGAGCAUGUGCUACGGU GUCUA | 108 |
| miR-105-2 | UGUGCAUCGUGGUCAAAUGCUCAGACUCCUGUGGUGGC UGCUUAUGCACCACGGAUGUUUGAGCAUGUGCUAUGGU GUCUA | 109 |
| miR-106-a | CCUUGGCCAUGUAAAAGUGCUUACAGUGCAGGUAGCUU UUUGAGAUCUACUGCAAUGUAAGCACUUCUUACAUUAC CAUGG | 110 |
| miR-106-b | CCUGCCGGGGCUAAAGUGCUGACAGUGCAGAUAGUGGU CCUCUCCGUGCUACCGCACUGUGGGUACUUGCUGCUCCA GCAGG | 111 |
| miR-107 | CUCUCUGCUUUCAGCUUCUUUACAGUGUUGCCUUGUGGC AUGGAGUUCAAGCAGCAUUGUACAGGGCUAUCAAAGCA CAGA | 112 |
| MIR-108-1-SMALL | ACACUGCAAGAACAAUAAGGAUUUUUAGGGGCAUUAUG ACUGAGUCAGAAAACACAGCUGCCCCUGAAAGUCCCUCA UUUUUCUUGCUGU | 113 |
| MIR-108-2-SMALL | ACUGCAAGAGCAAUAAGGAUUUUUAGGGGCAUUAUGAU AGUGGAAUGGAAACACAUCUGCCCCCAAAAGUCCCUCAU UUU | 114 |
| miR-122a-1 | CCUUAGCAGAGCUGUGGAGUGUGACAAUGGUGUUUGUG UCUAAACUAUCAAACGCCAUUAUCACACUAAAUAGCUAC UGCUAGGC | 115 |
| miR-122a-2 | AGCUGUGGAGUGUGACAAUGGUGUUUGUGUCCAAACUA UCAAACGCCAUUAUCACACUAAAUAGCU | 116 |
| miR-123 | ACAUUAUUACUUUUGGUACGCGCUGUGACACUUCAAAC UCGUACCGUGAGUAAUAAUGCGC | 117 |
| miR-124a-1 | AGGCCUCUCUCUCCGUGUUCACAGCGGACCUUGAUUUAA AUGUCCAUACAAUUAAGGCACGCGGUGAAUGCCAAGAA UGGGGCUG | 118 |
| miR-124a-2 | AUCAAGAUUAGAGGCUCUGCUCUCCGUGUUCACAGCGGA CCUUGAUUUAAAUGUCAUACAAUUAAGGCACGCGGUGAA UGCCAAGAGCGGAGCCUACGGCUGCACUUGAAG | 119 |
| miR-124a-3 | UGAGGGCCCCUCUGCGUGUUCACAGCGGACCUUGAUUUA AUGUCUAUACAAUUAAGGCACGCGGUGAAUGCCAAGAG AGGCGCCUCC | 120 |
| miR-124a | CUCUGCGUGUUCACAGCGGACCUUGAUUUAAUGUCUAU ACAAUUAAGGCACGCGGUGAAUGCCAAGAG | 121 |
| miR-124b | CUCUCCGUGUUCACAGCGGACCUUGAUUUAAUGUCAUAC AAUUAAGGCACGCGGUGAAUGCCAAGAG | 122 |
| miR-125a-1 | UGCCAGUCUCUAGGUCCCUGAGACCCUUUAACCUGUGAG GACAUCCAGGGUCACAGGUGAGGUUCUUGGGAGCCUGG CGUCUGGCC | 123 |
| miR-125a-2 | GGUCCCUGAGACCCUUUAACCUGUGAGGACAUCCAGGGU CACAGGUGAGGUUCUUGGGAGCCUGG | 124 |
| miR-125b-1 | UGCGCUCCUCUCAGUCCCUGAGACCCUAACUUGUGAUGU UUACCGUUUAAAUCCACGGGUUAGGCUCUUGGGAGCUG CGAGUCGUGCU | 125 |
| miR-125b-2 | ACCAGACUUUUCCUAGUCCCUGAGACCCUAACUUGUGAG GUAUUUUAGUAACAUCACAAGUCAGGCUCUUGGGACCU AGGCGGAGGGGA | 126 |
| miR-126-1 | CGCUGGCGACGGGACAUUAUUACUUUUGGUACGCGCUG UGACACUUCAAACUCGUACCGUGAGUAAUAAUGCGCCGU CCACGGCA | 127 |

TABLE 1a-continued

Human microRNA Precursor Sequences.

| Precursor Name | Sequence (5' To 3')* | SEQ ID NO. |
|---|---|---|
| miR-126-2 | ACAUUAUUACUUUUGGUACGCGCUGUGACACUUCAAAC UCGUACCGUGAGUAAUAAUGCGC | 128 |
| miR-127-1 | UGUGAUCACUGUCUCCAGCCUGCUGAAGCUCAGAGGGCU CUGAUUCAGAAAGAUCAUCGGAUCCGUCUGAGCUUGGC UGGUCGGAAGUCUCAUCAUC | 129 |
| miR-127-2 | CCAGCCUGCUGAAGCUCAGAGGGCUCUGAUUCAGAAAGA UCAUCGGAUCCGUCUGAGCUUGGCUGGUCGG | 130 |
| miR-128a | UGAGCUGUUGGAUUCGGGGCCGUAGCACUGUCUGAGAG GUUUACAUUUCUCACAGUGAACCGGUCUCUUUUUCAGCU GCUUC | 131 |
| miR-128b | GCCCGGCAGCCACUGUGCAGUGGGAAGGGGGCCGAUAC ACUGUACGAGAGUGAGUAGCAGGUCUCACAGUGAACCG GUCUCUUUCCUACUGUGUCACACUCCUAAUGG | 132 |
| miR-128 | GUUGGAUUCGGGGCCGUAGCACUGUCUGAGAGGUUUAC AUUUCUCACAGUGAACCGGUCUCUUUUUCAGC | 133 |
| miR-129-1 | UGGAUCUUUUUGCGGUCUGGGCUUGCUGUUCCUCUCAAC AGUAGUCAGGAAGCCCUUACCCCAAAAAGUAUCUA | 134 |
| MIR-129-2 | UGCCCUUCGCGAAUCUUUUUGCGGUCUGGGCUUGCUGUA CAUAACUCAAUAGCCGGAAGCCCUUACCCCAAAAAGCAU UUGCGGAGGGCG | 135 |
| miR-130a | UGCUGCUGGCCAGAGCUCUUUUCACAUUGUGCUACUGUC UGCACCUGUCACUAGCAGUGCAAUGUUAAAAGGGCAUU GGCCGUGUAGUG | 136 |
| miR-131-1 | GCCAGGAGGCGGGGUUGGUUGUUAUCUUUGGUUAUCUA GCUGUAUGAGUGGUGUGGAGUCUUCAUAAAGCUAGAUA ACCGAAAGUAAAAAUAACCCCAUACACUGCGCAG | 137 |
| miR-131-3 | CACGGCGCGGCAGCGGCACUGGCUAAGGGAGGCCCGUUU CUCUCUUUGGUUAUCUAGCUGUAUGAGUGCCACAGAGCC GUCAUAAAGCUAGAUAACCGAAAGUAGAAAUG | 138 |
| miR-131 | GUUGUUAUCUUUGGUUAUCUAGCUGUAUGAGUGUAUUG GUCUUCAUAAAGCUAGAUAACCGAAAGUAAAAAC | 139 |
| miR-132-1 | CCGCCCCCGCGUCUCCAGGGCAACCGUGGCUUUCGAUUG UUACUGUGGGAACUGGAGGUAACAGUCUACAGCCAUGG UCGCCCCGCAGCACGCCCACGCGC | 140 |
| miR-132-2 | GGGCAACCGUGGCUUUCGAUUGUUACUGUGGGAACUGG AGGUAACAGUCUACAGCCAUGGUCGCCC | 141 |
| miR-133a-1 | ACAAUGCUUUGCUAGAGCUGGUAAAAUGGAACCAAAUC GCCUCUUCAAUGGAUUUGGUCCCCUUCAACCAGCUGUAG CUAUGCAUUGA | 142 |
| miR-133a-2 | GGGAGCCAAAUGCUUUGCUAGAGCUGGUAAAAUGGAAC CAAAUCGACUGUCCAAUGGAUUUGGUCCCCUUCAACCAG CUGUAGCUGUGCAUUGAUGGCGCCG | 143 |
| miR-133 | GCUAGAGCUGGUAAAAUGGAACCAAAUCGCCUCUUCAA UGGAUUUGGUCCCCUUCAACCAGCUGUAGC | 144 |
| miR-133b | CCUCAGAAGAAAGAUGCCCCCUGCUCUGGCUGGUCAAAC GGAACCAAGUCCGUCUUCCUGAGAGGUUUGGUCCCCUUC AACCAGCUACAGCAGGGCUGGCAAUGCCCAGUCCUUGGA GA | 145 |
| MIR-133B-SMALL | GCCCCCUGCUCUGGCUGGUCAAACGGAACCAAGUCCGUC UUCCUGAGAGGUUUGGUCCCCUUCAACCAGCUACAGCAG GG | 146 |
| miR-134-1 | CAGGGUGUGUGACUGGUUGACCAGAGGGGCAUGCACUG UGUUCACCCUGUGGGCCACCUAGUCACCAACCCUC | 147 |

TABLE 1a-continued

Human microRNA Precursor Sequences.

| Precursor Name | Sequence (5' To 3')* | SEQ ID NO. |
|---|---|---|
| miR-134-2 | AGGGUGUGUGACUGGUUGACCAGAGGGGCAUGCACUGU GUUCACCCUGUGGGCCACCUAGUCACCAACCCU | 148 |
| miR-135a-1 | AGGCCUCGCUGUUCUCUAUGGCUUUUUAUUCCUAUGUG AUUCUACUGCUCACUCAUAUAGGGAUUGGAGCCGUGGC GCACGGCGGGGACA | 149 |
| miR-135a-2 (miR-135-2) | AGAUAAAUUCACUCUAGUGCUUUAUGGCUUUUUAUUCC UAUGUGAUAGUAAUAAAGUCUCAUGUAGGGAUGGAAGC CAUGAAAUACAUUGUGAAAAAUCA | 150 |
| miR-135 | CUAUGGCUUUUUAUUCCUAUGUGAUUCUACUGCUCACUC AUAUAGGGAUUGGAGCCGUGG | 151 |
| miR-135b | CACUCUGCUGUGGCCUAUGGCUUUUCAUUCCUAUGUGAU UGCUGUCCCAAACUCAUGUAGGGCUAAAAGCCAUGGGCU ACAGUGAGGGGCGAGCUCC | 152 |
| miR-136-1 | UGAGCCCUCGGAGGACUCCAUUUGUUUUGAUGAUGGAU UCUUAUGCUCCAUCAUCGUCUCAAAUGAGUCUUCAGAGG GUUCU | 153 |
| miR-136-2 | GAGGACUCCAUUUGUUUUGAUGAUGGAUUCUUAUGCUC CAUCAUCGUCUCAAAUGAGUCUUC | 154 |
| miR-137 | CUUCGGUGACGGGUAUUCUUGGGUGGAUAAUACGGAUU ACGUUGUUAUUGCUUAAGAAUACGCGUAGUCGAGG | 155 |
| miR-138-1 | CCCUGGCAUGGUGUGGUGGGGCAGCUGGUGUUGUGAAU CAGGCCGUUGCCAAUCAGAGAACGGCUACUUCACAACAC CAGGGCCACACCACACUACAGG | 156 |
| miR-138-2 | CGUUGCUGCAGCUGGUGUUGUGAAUCAGGCCGACGAGC AGCGCAUCCUCUUACCCGGCUAUUUCACGACACCAGGGU UGCAUCA | 157 |
| miR-138 | CAGCUGGUGUUGUGAAUCAGGCCGACGAGCAGCGCAUCC UCUUACCCGGCUAUUUCACGACACCAGGGUUG | 158 |
| miR-139 | GUGUAUUCUACAGUGCACGUGUCUCCAGUGUGGCUCGG AGGCUGGAGACGCGGCCCUGUUGGAGUAAC | 159 |
| miR-140 | UGUGUCUCUCUCUGUGUCCUGCCAGUGGUUUUACCCUAU GGUAGGUUACGUCAUGCUGUUCUACCACAGGGUAGAAC CACGGACAGGAUACCGGGCACC | 160 |
| miR-140as | UCCUGCCAGUGGUUUUACCCUAUGGUAGGUUACGUCAU GCUGUUCUACCACAGGGUAGAACCACGGACAGGA | 161 |
| miR-140s | CCUGCCAGUGGUUUUACCCUAUGGUAGGUUACGUCAUGC UGUUCUACCACAGGGUAGAACCACGGACAGG | 162 |
| miR-141-1 | CGGCCGGCCCUGGGUCCAUCUUCCAGUACAGUGUUGGAU GGUCUAAUUGUGAAGCUCCUAACACUGUCUGGUAAAGA UGGCUCCCGGGUGGGUUC | 163 |
| miR-141-2 | GGGUCCAUCUUCCAGUACAGUGUUGGAUGGUCUAAUUG UGAAGCUCCUAACACUGUCUGGUAAAGAUGGCCC | 164 |
| miR-142 | ACCCAUAAAGUAGAAAGCACUACUAACAGCACUGGAGG GUGUAGUGUUUCCUACUUUAUGGAUG | 165 |
| miR-143-1 | GCGCAGCGCCCUGUCUCCCAGCCUGAGGUGCAGUGCUGC AUCUCUGGUCAGUUGGGAGUCUGAGAUGAAGCACUGUA GCUCAGGAAGAGAAGUUGUUCUGCAGC | 166 |
| miR-143-2 | CCUGAGGUGCAGUGCUGCAUCUCUGGUCAGUUGGGAGU CUGAGAUGAAGCACUGUAGCUCAGG | 167 |
| miR-144-1 | UGGGGCCCUGGCUGGGAUAUCAUCAUAUACUGUAAGUU UGCGAUGAGACACUACAGUAUAGAUGAUGUACUAGUCC GGGCACCCCC | 168 |

TABLE 1a-continued

Human microRNA Precursor Sequences.

| Precursor Name | Sequence (5' To 3')* | SEQ ID NO. |
|---|---|---|
| miR-144-2 | GGCUGGGAUAUCAUCAUAUACUGUAAGUUUGCGAUGAG ACACUACAGUAUAGAUGAUGUACUAGUC | 169 |
| miR-145-1 | CACCUUGUCCUCACGGUCCAGUUUUCCCAGGAAUCCCUU AGAUGCUAAGAUGGGGAUUCCUGGAAAUACUGUUCUUG AGGUCAUGGUU | 170 |
| miR-145-2 | CUCACGGUCCAGUUUUCCCAGGAAUCCCUUAGAUGCUAA GAUGGGGAUUCCUGGAAAUACUGUUCUUGAG | 171 |
| miR-146-1 | CCGAUGUGUAUCCUCAGCUUUGAGAACUGAAUUCCAUG GGUUGUGUCAGUGUCAGACCUCUGAAAUUCAGUUCUUC AGCUGGGAUAUCUCUGUCAUCGU | 172 |
| miR-146-2 | AGCUUUGAGAACUGAAUUCCAUGGGUUGUGUCAGUGUC AGACCUGUAAAUUCAGUUCUUCAGCU | 173 |
| miR-147 | AAUCUAAAGACAACAUUUCUGCACACACACCAGACUAUG GAAGCCAGUGUGUGGAAAUGCUUCUGCUAGAUU | 174 |
| miR-148a (miR-148) | GAGGCAAAGUUCUGAGACACUCCGACUCUGAGUAUGAU AGAAGUCAGUGCACUACAGAACUUUGUCUC | 175 |
| miR-148b | CAAGCACGAUUAGCAUUUGAGGUGAAGUUCUGUUAUAC ACUCAGGCUGUGGCUCUCUGAAAGUCAGUGCAUCACAGA ACUUUGUCUCGAAAGCUUUCUA | 176 |
| MIR-148B-SMALL | AAGCACGAUUAGCAUUUGAGGUGAAGUUCUGUUAUACA CUCAGGCUGUGGCUCUCUGAAAGUCAGUGCAU | 177 |
| miR-149-1 | GCCGGCGCCCGAGCUCUGGCUCCGUGUCUUCACUCCCGU GCUUGUCCGAGGAGGGAGGGAGGGACGGGGGCUGUGCU GGGGCAGCUGGA | 178 |
| miR-149-2 | GCUCUGGCUCCGUGUCUUCACUCCCGUGCUUGUCCGAGG AGGGAGGGAGGGAC | 179 |
| miR-150-1 | CUCCCCAUGGCCCUGUCUCCCAACCCUUGUACCAGUGCU GGGCUCAGACCCUGGUACAGGCCUGGGGGACAGGGACCU GGGGAC | 180 |
| miR-150-2 | CCCUGUCUCCCAACCCUUGUACCAGUGCUGGGCUCAGAC CCUGGUACAGGCCUGGGGGACAGGG | 181 |
| miR-151 | UUUCCUGCCCUCGAGGAGCUCACAGUCUAGUAUGUCUCA UCCCCUACUAGACUGAAGCUCCUUGAGGACAGG | 182 |
| MIR-151-2 | CCUGUCCUCAAGGAGCUUCAGUCUAGUAGGGGAUGAGA CAUACUAGACUGUGAGCUCCUCGAGGGCAGG | 183 |
| miR-152-1 | UGUCCCCCCGGCCCAGGUUCUGUGAUACACUCCGACUC GGGCUCUGGAGCAGUCAGUGCAUGACAGAACUUGGGCCC GGAAGGACC | 184 |
| miR-152-2 | GGCCCAGGUUCUGUGAUACACUCCGACUCGGGCUCUGGA GCAGUCAGUGCAUGACAGAACUUGGGCCCCGG | 185 |
| miR-153-1-1 | CUCACAGCUGCCAGUGUCAUUUUUGUGAUCUGCAGCUAG UAUUCUCACUCCAGUUGCAUAGUCACAAAAGUGAUCAU UGGCAGGUGUGGC | 186 |
| miR-153-1-2 | UCUCUCUCUCCCUCACAGCUGCCAGUGUCAUUGUCACAA AAGUGAUCAUUGGCAGGUGUGGCUGCUGCAUG | 187 |
| miR-153-2-1 | AGCGGUGGCCAGUGUCAUUUUUGUGAUGUUGCAGCUAG UAAUAUGAGCCCAGUUGCAUAGUCACAAAAGUGAUCAU UGGAAACUGUG | 188 |
| miR-153-2-2 | CAGUGUCAUUUUUGUGAUGUUGCAGCUAGUAAUAUGAG CCCAGUUGCAUAGUCACAAAAGUGAUCAUUG | 189 |
| miR-154-1 | GUGGUACUUGAAGAUAGGUUAUCCGUGUUGCCUUCGCU UUAUUUGUGACGAAUCAUACACGGUUGACCUAUUUUUC AGUACCAA | 190 |

TABLE 1a-continued

Human microRNA Precursor Sequences.

| Precursor Name | Sequence (5' To 3')* | SEQ ID NO. |
|---|---|---|
| miR-154-2 | GAAGAUAGGUUAUCCGUGUUGCCUUCGCUUUAUUUGUG ACGAAUCAUACACGGUUGACCUAUUUUU | 191 |
| miR-155 | CUGUUAAUGCUAAUCGUGAUAGGGGUUUUUGCCUCCAA CUGACUCCUACAUAUUAGCAUUAACAG | 192 |
| MIR-156 = MIR-157 = OVER-LAP MIR-141 | CCUAACACUGUCUGGUAAAGAUGGCUCCCGGGUGGGUUC UCUCGGCAGUAACCUUCAGGGAGCCCUGAAGACCAUGGA GGAC | 193 |
| MIR-158-SMALL = MIR-192 | GCCGAGACCGAGUGCACAGGGCUCUGACCUAUGAAUUGA CAGCCAGUGCUCUCGUCUCCCCUCUGGCUGCCAAUUCCA UAGGUCACAGGUAUGUUCGCCUCAAUGCCAGC | 194 |
| MIR-159-1-SMALL | UCCCGCCCCCUGUAACAGCAACUCCAUGUGGAAGUGCCC ACUGGUUCCAGUGGGGCUGCUGUUAUCUGGGGCGAGGG CCA | 195 |
| MIR-161-SMALL | AAAGCUGGGUUGAGAGGGCGAAAAAGGAUGAGGUGACU GGUCUGGGCUACGCUAUGCUGCGGCGCUCGGG | 196 |
| MIR-163-1B-SMALL | CAUUGGCCUCCUAAGCCAGGGAUUGUGGGUUCGAGUCCC ACCCGGGGUAAAGAAAGGCCGAAUU | 197 |
| MIR-163-3-SMALL | CCUAAGCCAGGGAUUGUGGGUUCGAGUCCCACCUGGGGU AGAGGUGAAAGUUCCUUUUACGGAAUUUUUU | 198 |
| miR-162 | CAAUGUCAGCAGUGCCUUAGCAGCACGUAAAUAUUGGC GUUAAGAUUCUAAAAUUAUCUCCAGUAUUAACUGUGCU GCUGAAGUAAGGUUGACCAUACUCUACAGUUG | 199 |
| MIR-175-SMALL = MIR-224 | GGGCUUUCAAGUCACUAGUGGUUCCGUUUAGUAGAUGA UUGUGCAUUGUUUCAAAAUGGUGCCCUAGUGACUACAA AGCCC | 200 |
| MIR-177-SMALL | ACGCAAGUGUCCUAAGGUGAGCUCAGGGAGCACAGAAA CCUCCAGUGGAACAGAAGGGCAAAAGCUCAUU | 201 |
| MIR-180-SMALL | CAUGUGUCACUUUCAGGUGGAGUUUCAAGAGUCCCUUCC UGGUUCACCGUCUCCUUUGCUCUUCCACAAC | 202 |
| miR-181a | AGAAGGGCUAUCAGGCCAGCCUUCAGAGGACUCCAAGGA ACAUUCAACGCUGUCGGUGAGUUUGGGAUUUGAAAAAA CCACUGACCGUUGACUGUACCUUGGGGUCCUUA | 203 |
| miR-181b-1 | CCUGUGCAGAGAUUAUUUUUUAAAAGGUCACAAUCAAC AUUCAUUGCUGUCGGUGGGUUGAACUGUGUGGACAAGC UCACUGAACAAUGAAUGCAACUGUGGCCCCGCUU | 204 |
| miR-181b-2 | CUGAUGGCUGCACUCAACAUUCAUUGCUGUCGGUGGGU UUGAGUCUGAAUCAACUCACUGAUCAAUGAAUGCAAAC UGCGGACCAAACA | 205 |
| miR-181c | CGGAAAAUUUGCCAAGGGUUUGGGGGAACAUUCAACCU GUCGGUGAGUUUGGGCAGCUCAGGCAAACCAUCGACCGU UGAGUGGACCCUGAGGCCUGGAAUUGCCAUCCU | 206 |
| miR-182-as | GAGCUGCUUGCCUCCCCCCGUUUUUGGCAAUGGUAGAAC UCACACUGGUGAGGUAACAGGAUCCGGUGGUUCUAGAC UUGCCAACUAUGGGGCGAGGACUCAGCCGGCAC | 207 |
| miR-182 | UUUUUGGCAAUGGUAGAACUCACACUGGUGAGGUAACA GGAUCCGGUGGUUCUAGACUUGCCAACUAUGG | 208 |
| miR-183 | CCGCAGAGUGUGACUCCUGUUCUGUGUAUGGCACUGGU AGAAUUCACUGUGAACAGUCUCAGUCAGUGAAUUACCG AAGGGCCAUAAACAGAGCAGAGACAGAUCCACGA | 209 |
| miR-184-1 | CCAGUCACGUCCCCUUAUCACUUUUCCAGCCCAGCUUUG UGACUGUAAGUGUUGGACGGAGAACUGAUAAGGGUAGG UGAUUGA | 210 |

TABLE 1a-continued

Human microRNA Precursor Sequences.

| Precursor Name | Sequence (5' To 3')* | SEQ ID NO. |
|---|---|---|
| miR-184-2 | CCUUAUCACUUUUCCAGCCCAGCUUUGUGACUGUAAGUG UUGGACGGAGAACUGAUAAGGGUAGG | 211 |
| miR-185-1 | AGGGGGCGAGGGAUUGGAGAGAAAGGCAGUUCCUGAUG GUCCCCUCCCCAGGGGCUGGCUUUCCUCUGGUCCUUCCC UCCCA | 212 |
| miR-185-2 | AGGGAUUGGAGAGAAAGGCAGUUCCUGAUGGUCCCCUC CCCAGGGGCUGGCUUUCCUCUGGUCCUU | 213 |
| miR-186-1 | UGCUUGUAACUUUCCAAAGAAUUCUCCUUUUGGGCUUU CUGGUUUUAUUUUAAGCCCAAAGGUGAAUUUUUUGGGA AGUUUGAGCU | 214 |
| miR-186-2 | ACUUUCCAAAGAAUUCUCCUUUUGGGCUUUCUGGUUUU AUUUUAAGCCCAAAGGUGAAUUUUUUGGGAAGU | 215 |
| miR-187 | GGUCGGGCUCACCAUGACACAGUGUGAGACUCGGGCUAC AACACAGGACCCGGGGCGCUGCUCUGACCCCUCGUGUCU UGUGUUGCAGCCGGAGGGACGCAGGUCCGCA | 216 |
| miR-188-1 | UGCUCCCUCUCUCACAUCCCUUGCAUGGUGGAGGGUGAG CUUUCUGAAAACCCCUCCCACAUGCAGGGUUUGCAGGAU GGCGAGCC | 217 |
| miR-188-2 | UCUCACAUCCCUUGCAUGGUGGAGGGUGAGCUUUCUGA AAACCCCUCCCACAUGCAGGGUUUGCAGGA | 218 |
| miR-189-1 | CUGUCGAUUGGACCCGCCCUCCGGUGCCUACUGAGCUGA UAUCAGUUCUCAUUUUACACACUGGCUCAGUUCAGCAGG AACAGGAGUCGAGCCCUUGAGCAA | 219 |
| miR-189-2 | CUCCGGUGCCUACUGAGCUGAUAUCAGUUCUCAUUUUAC ACACUGGCUCAGUUCAGCAGGAACAGGAG | 220 |
| miR-190-1 | UGCAGGCCUCUGUGUGAUAUGUUUGAUAUAUUAGGUUG UUAUUUAAUCCAACUAUAUAUCAAACAUAUUCCUACAG UGUCUUGCC | 221 |
| miR-190-2 | CUGUGUGAUAUGUUUGAUAUAUUAGGUUGUUAUUUAAU CCAACUAUAUAUCAAACAUAUUCCUACAG | 222 |
| miR-191-1 | CGGCUGGACAGCGGGCAACGGAAUCCCAAAAGCAGCUGU UGUCUCCAGAGCAUUCCAGCUGCGCUUGGAUUUCGUCCC CUGCUCUCCUGCCU | 223 |
| miR-191-2 | AGCGGGCAACGGAAUCCCAAAAGCAGCUGUUGUCUCCAG AGCAUUCCAGCUGCGCUUGGAUUUCGUCCCCUGCU | 224 |
| miR-192-2/3 | CCGAGACCGAGUGCACAGGGCUCUGACCUAUGAAUUGAC AGCCAGUGCUCUCGUCUCCCCUCUGGCUGCCAAUUCCAU AGGUCACAGGUAUGUUCGCCUCAAUGCCAG | 225 |
| miR-192 | GCCGAGACCGAGUGCACAGGGCUCUGACCUAUGAAUUGA CAGCCAGUGCUCUCGUCUCCCCUCUGGCUGCCAAUUCCA UAGGUCACAGGUAUGUUCGCCUCAAUGCCAGC | 226 |
| miR-193-1 | CGAGGAUGGGAGCUGAGGGCUGGGUCUUUGCGGGCGAG AUGAGGGUGUCGGAUCAACUGGCCUACAAAGUCCCAGU UCUCGGCCCCCG | 227 |
| miR-193-2 | GCUGGGUCUUUGCGGGCGAGAUGAGGGUGUCGGAUCAA CUGGCCUACAAAGUCCCAGU | 228 |
| miR-194-1 | AUGGUGUUAUCAAGUGUAACAGCAACUCCAUGUGGACU GUGUACCAAUUUCCAGUGGAGAUGCUGUUACUUUUGAU GGUUACCAA | 229 |
| miR-194-2 | GUGUAACAGCAACUCCAUGUGGACUGUGUACCAAUUUCC AGUGGAGAUGCUGUUACUUUUGAU | 230 |
| miR-195-1 | AGCUUCCCUGGCUCUAGCAGCACAGAAAUAUUGGCACAG GGAAGCGAGUCUGCCAAUAUUGGCUGUGCUGCUCCAGGC AGGGUGGUG | 231 |

TABLE 1a-continued

Human microRNA Precursor Sequences.

| Precursor Name | Sequence (5' To 3')* | SEQ ID NO. |
|---|---|---|
| miR-195-2 | UAGCAGCACAGAAAUAUUGGCACAGGGAAGCGAGUCUG CCAAUAUUGGCUGUGCUGCU | 232 |
| miR-196-1 | CUAGAGCUUGAAUUGGAACUGCUGAGUGAAUUAGGUAG UUUCAUGUUGUUGGGCCUGGGUUUCUGAACACAACAAC AUUAAACCACCCGAUUCACGGCAGUUACUGCUCC | 233 |
| miR-196a-1 | GUGAAUUAGGUAGUUUCAUGUUGUUGGGCCUGGGUUUC UGAACACAACAACAUUAAACCACCCGAUUCAC | 234 |
| miR-196a-2 (miR-196-2) | UGCUCGCUCAGCUGAUCUGUGGCUUAGGUAGUUUCAUG UUGUUGGGAUUGAGUUUUGAACUCGGCAACAAGAAACU GCCUGAGUUACAUCAGUCGGUUUUCGUCGAGGGC | 235 |
| miR-196 | GUGAAUUAGGUAGUUUCAUGUUGUUGGGCCUGGGUUUC UGAACACAACAACAUUAAACCACCCGAUUCAC | 236 |
| miR-196b | ACUGGUCGGUGAUUUAGGUAGUUUCCUGUUGUUGGGAU CCACCUUUCUCUCGACAGCACGACACUGCCUUCAUUACU UCAGUUG | 237 |
| miR-197 | GGCUGUGCCGGGUAGAGAGGGCAGUGGGAGGUAAGAGC UCUUCACCCUUCACCACCUUCUCCACCCAGCAUGGCC | 238 |
| MIR-197-2 | GUGCAUGUGUAUGUAUGUGUGCAUGUGCAUGUGUAUGU GUAUGAGUGCAUGCGUGUGUGC | 239 |
| miR-198 | UCAUUGGUCCAGAGGGGAGAUAGGUUCCUGUGAUUUUU CCUUCUUCUCUAUAGAAUAAAUGA | 240 |
| miR-199a-1 | GCCAACCCAGUGUUCAGACUACCUGUUCAGGAGGCUCUC AAUGUGUACAGUAGUCUGCACAUUGGUUAGGC | 241 |
| miR-199a-2 | AGGAAGCUUCUGGAGAUCCUGCUCCGUCGCCCCAGUGUU CAGACUACCUGUUCAGGACAAUGCCGUUGUACAGUAGUC UGCACAUUGGUUAGACUGGGCAAGGGAGAGCA | 242 |
| miR-199b | CCAGAGGACACCUCCACUCCGUCUACCCAGUGUUUAGAC UAUCUGUUCAGGACUCCCAAAUUGUACAGUAGUCUGCAC AUUGGUUAGGCUGGGCUGGGUUAGACCCUCGG | 243 |
| miR-199s | GCCAACCCAGUGUUCAGACUACCUGUUCAGGAGGCUCUC AAUGUGUACAGUAGUCUGCACAUUGGUUAGGC | 244 |
| miR-200a | GCCGUGGCCAUCUUACUGGGCAGCAUUGGAUGGAGUCA GGUCUCUAAUACUGCCUGGUAAUGAUGACGGC | 245 |
| miR-200b | CCAGCUCGGGCAGCCGUGGCCAUCUUACUGGGCAGCAUU GGAUGGAGUCAGGUCUCUAAUACUGCCUGGUAAUGAUG ACGGCGGAGCCCUGCACG | 246 |
| miR-200c | CCCUCGUCUUACCCAGCAGUGUUUGGGUGCGGUUGGGAG UCUCUAAUACUGCCGGGUAAUGAUGGAGG | 247 |
| miR-202 | GUUCCUUUUUCCUAUGCAUAUACUUCUUUGAGGAUCUG GCCUAAAGAGGUAUAGGGCAUGGGAAGAUGGAGC | 248 |
| miR-203 | GUGUUGGGACUCGCGCGCUGGGUCCAGUGGUUCUUAA CAGUUCAACAGUUCUGUAGCGCAAUUGUGAAAUGUUUA GGACCACUAGACCCGGCGGGCGCGGCGACAGCGA | 249 |
| miR-204 | GGCUACAGUCUUUCUUCAUGUGACUCGUGGACUUCCCUU UGUCAUCCUAUGCCUGAGAAUAUAUGAAGGAGGCUGGG AAGGCAAAGGGACGUUCAAUUGUCAUCACUGGC | 250 |
| miR-205 | AAAGAUCCUCAGACAAUCCAUGUGCUUCUCUUGUCCUUC AUUCCACCGGAGUCUGUCUCAUACCCAACCAGAUUUCAG UGGAGUGAAGUUCAGGAGGCAUGGAGCUGACA | 251 |
| miR-206-1 | UGCUUCCCGAGGCCACAUGCUUCUUUAUAUCCCCAUAUG GAUUACUUUGCUAUGGAAUGUAAGGAAGUGUGUGGUUU CGGCAAGUG | 252 |

TABLE 1a-continued

Human microRNA Precursor Sequences.

| Precursor Name | Sequence (5' To 3')* | SEQ ID NO. |
| --- | --- | --- |
| miR-206-2 | AGGCCACAUGCUUCUUUAUAUCCCCAUAUGGAUUACUUU GCUAUGGAAUGUAAGGAAGUGUGUGGUUUU | 253 |
| miR-208 | UGACGGGCGAGCUUUUGGCCCGGGUUAUACCUGAUGCUC ACGUAUAAGACGAGCAAAAAGCUUGUUGGUCA | 254 |
| miR-210 | ACCCGGCAGUGCCUCCAGGCGCAGGGCAGCCCCUGCCCA CCGCACACUGCGCUGCCCCAGACCCACUGUGCGUGUGAC AGCGGCUGAUCUGUGCCUGGGCAGCGCGACCC | 255 |
| miR-211 | UCACCUGGCCAUGUGACUUGUGGGCUUCCCUUUGUCAUC CUUCGCCUAGGGCUCUGAGCAGGGCAGGGACAGCAAAGG GGUGCUCAGUUGUCACUUCCCACAGCACGGAG | 256 |
| miR-212 | CGGGGCACCCCGCCCGGACAGCGCGCCGGCACCUUGGCU CUAGACUGCUUACUGCCCGGGCCGCCCUCAGUAACAGUC UCCAGUCACGGCCACCGACGCCUGGCCCCGCC | 257 |
| miR-213-2 | CCUGUGCAGAGAUUAUUUUUUAAAAGGUCACAAUCAAC AUUCAUUGCUGUCGGUGGGUUGAACUGUGUGGACAAGC UCACUGAACAAUGAAUGCAACUGUGGCCCCGCUU | 258 |
| miR-213 | GAGUUUUGAGGUUGCUUCAGUGAACAUUCAACGCUGUC GGUGAGUUUGGAAUUAAAAUCAAAACCAUCGACCGUUG AUUGUACCCUAUGGCUAACCAUCAUCUACUCC | 259 |
| miR-214 | GGCCUGGCUGGACAGAGUUGUCAUGUGUCUGCCUGUCU ACACUUGCUGUGCAGAACAUCCGCUCACCUGUACAGCAG GCACAGACAGGCAGUCACAUGACAACCCAGCCU | 260 |
| miR-215 | AUCAUUCAGAAAUGGUAUACAGGAAAAUGACCUAUGAA UUGACAGACAAUAUAGCUGAGUUUGUCUGUCAUUUCUU UAGGCCAAUAUUCUGUAUGACUGUGCUACUUCAA | 261 |
| miR-216 | GAUGGCUGUGAGUUGGCUUAAUCUCAGCUGGCAACUGU GAGAUGUUCAUACAAUCCCUCACAGUGGUCUCUGGGAU UAUGCUAAACAGAGCAAUUUCCUAGCCCUCACGA | 262 |
| miR-217 | AGUAUAAUUAUUACAUAGUUUUUGAUGUCGCAGAUACU GCAUCAGGAACUGAUUGGAUAAGAAUCAGUCACCAUCA GUUCCUAAUGCAUUGCCUUCAGCAUCUAAACAAG | 263 |
| miR-218-1 | GUGAUAAUGUAGCGAGAUUUUCUGUUGUGCUUGAUCUA ACCAUGUGGUUGCGAGGUAUGAGUAAAACAUGGUUCCG UCAAGCACCAUGGAACGUCACGCAGCUUUCUACA | 264 |
| miR-218-2 | GACCAGUCGCUGCGGGGCUUUCCUUUGUGCUUGAUCUAA CCAUGUGGUGGAACGAUGGAAACGGAACAUGGUUCUGU CAAGCACCGCGGAAAGCACCGUGCUCUCCUGCA | 265 |
| miR-219 | CCGCCCCGGGCCGCGGCUCCUGAUUGUCCAAACGCAAUU CUCGAGUCUAUGGCUCCGGCCGAGAGUUGAGUCUGGACG UCCCGAGCCGCCGCCCCCAAACCUCGAGCGGG | 266 |
| miR-219-1 | CCGCCCCGGGCCGCGGCUCCUGAUUGUCCAAACGCAAUU CUCGAGUCUAUGGCUCCGGCCGAGAGUUGAGUCUGGACG UCCCGAGCCGCCGCCCCCAAACCUCGAGCGGG | 267 |
| miR-219-2 | ACUCAGGGGCUUCGCCACUGAUUGUCCAAACGCAAUUCU UGUACGAGUCUGCGGCCAACCGAGAAUUGUGGCUGGAC AUCUGUGGCUGAGCUCCGGG | 268 |
| miR-220 | GACAGUGUGGCAUUGUAGGGCUCCACACCGUAUCUGACA CUUUGGGCGAGGGCACCAUGCUGAAGGUGUUCAUGAUG CGGUCUGGGAACUCCUCACGGAUCUUACUGAUG | 269 |
| miR-221 | UGAACAUCCAGGUCGGGGCAUGAACCUGGCAUACAAU GUAGAUUUCUGUGUUCGUUAGGCAACAGCUACAUUGUC UGCUGGGUUUCAGGCUACCUGGAAACAUGUUCUC | 270 |
| miR-222 | GCUGCUGGAAGGUGUAGGUACCCUCAAUGGCUCAGUAG CCAGUGUAGAUCCUGUCUUUCGUAAUCAGCAGCUACAUC UGGCUACUGGGUCUCUGAUGGCAUCUUCUAGCU | 271 |

TABLE 1a-continued

Human microRNA Precursor Sequences.

| Precursor Name | Sequence (5' To 3')* | SEQ ID NO. |
|---|---|---|
| miR-223 | CCUGGCCUCCUGCAGUGCCACGCUCCGUGUAUUUGACAA GCUGAGUUGGACACUCCAUGUGGUAGAGUGUCAGUUUG UCAAAUACCCCAAGUGCGGCACAUGCUUACCAG | 272 |
| miR-224 | GGGCUUUCAAGUCACUAGUGGUUCCGUUUAGUAGAUGA UUGUGCAUUGUUUCAAAAUGGUGCCCUAGUGACUACAA AGCCC | 273 |
| MIR-294-1 (CHR16) | CAAUCUUCCUUUAUCAUGGUAUUGAUUUUUCAGUGCUU CCCUUUUGUGUGAGAGAAGAUA | 274 |
| miR-296 | AGGACCCUUCCAGAGGGCCCCCCCUCAAUCCUGUUGUGC CUAAUUCAGAGGGUUGGGUGGAGGCUCUCCUGAAGGGC UCU | 275 |
| miR-299 | AAGAAAUGGUUUACCGUCCCACAUACAUUUUGAAUAUG UAUGUGGGAUGGUAAACCGCUUCUU | 276 |
| miR-301 | ACUGCUAACGAAUGCUCUGACUUUAUUGCACUACUGUAC UUUACAGCUAGCAGUGCAAUAGUAUUGUCAAAGCAUCU GAAAGCAGG | 277 |
| miR-302a | CCACCACUUAAACGUGGAUGUACUUGCUUUGAAACUAA AGAAGUAAGUGCUUCCAUGUUUUGGUGAUGG | 278 |
| miR-302b | GCUCCCUUCAACUUUAACAUGGAAGUGCUUUCUGUGACU UUAAAAGUAAGUGCUUCCAUGUUUUAGUAGGAGU | 279 |
| miR-302c | CCUUUGCUUUAACAUGGGGGUACCUGCUGUGUGAAACA AAAGUAAGUGCUUCCAUGUUUCAGUGGAGG | 280 |
| miR-302d | CCUCUACUUUAACAUGGAGGCACUUGCUGUGACAUGACA AAAAUAAGUGCUUCCAUGUUUGAGUGUGG | 281 |
| miR-320 | GCUUCGCUCCCCUCCGCCUUCUCUUCCCGGUUCUUCCCG GAGUCGGGAAAAGCUGGGUUGAGAGGGCGAAAAAGGAU GAGGU | 282 |
| miR-321 | UUGGCCUCCUAAGCCAGGGAUUGUGGGUUCGAGUCCCAC CCGGGGUAAAGAAAGGCCGA | 283 |
| miR-323 | UUGGUACUUGGAGAGAGGUGGUCCGUGGCGCGUUCGCU UUAUUUAUGGCGCACAUUACACGGUCGACCUCUUUGCAG UAUCUAAUC | 284 |
| miR-324 | CUGACUAUGCCUCCCCGCAUCCCCUAGGGCAUUGGUGUA AAGCUGGAGACCCACUGCCCCAGGUGCUGCUGGGGGUUG UAGUC | 285 |
| miR-325 | AUACAGUGCUUGGUUCCUAGUAGGUGUCCAGUAAGUGU UUGUGACAUAAUUUGUUUAUUGAGGACCUCCUAUCAAU CAAGCACUGUGCUAGGCUCUGG | 286 |
| miR-326 | CUCAUCUGUCUGUUGGGCUGGAGGCAGGGCCUUUGUGA AGGCGGGUGGUGCUCAGAUCGCCUCUGGGCCCUUCCUCC AGCCCCGAGGCGGAUUCA | 287 |
| miR-328 | UGGAGUGGGGGGCAGGAGGGGCUCAGGGAGAAAGUGC AUACAGCCCCUGGCCCUCUCUGCCCUUCCGUCCCCUG | 288 |
| miR-330 | CUUUGGCGAUCACUGCCUCUCUGGGCCUGUGUCUUAGGC UCUGCAAGAUCAACCGAGCAAAGCACACGGCCUGCAGAG AGGCAGCGCUCUGCCC | 289 |
| miR-331 | GAGUUUGGUUUUGUUUGGGUUUGUUCUAGGUAUGGUCC CAGGGAUCCCAGAUCAAACCAGGCCCCUGGGCCUAUCCU AGAACCAACCUAAGCUC | 290 |
| miR-335 | UGUUUUGAGCGGGGUCAAGAGCAAUAACGAAAAAUGU UUGUCAUAAACCGUUUUUCAUUAUUGCUCCUGACCUCCU CUCAUUUGCUAUAUUCA | 291 |

TABLE 1a-continued

Human microRNA Precursor Sequences.

| Precursor Name | Sequence (5' To 3')* | SEQ ID NO. |
|---|---|---|
| miR-337 | GUAGUCAGUAGUUGGGGGUGGGAACGGCUUCAUACAG GAGUUGAUGCACAGUUAUCCAGCUCCUAUAUGAUGCCU UUCUUCAUCCCCUUCAA | 292 |
| miR-338 | UCUCCAACAAUAUCCUGGUGCUGAGUGAUGACUCAGGCG ACUCCAGCAUCAGUGAUUUUGUUGAAGA | 293 |
| miR-339 | CGGGGCGGCCGCUCUCCCUGUCCUCCAGGAGCUCACGUG UGCCUGCCUGUGAGCGCCUCGACGACAGAGCCGGCGCCU GCCCCAGUGUCUGCGC | 294 |
| miR-340 | UUGUACCUGGUGUGAUUAUAAAGCAAUGAGACUGAUUG UCAUAUGUCGUUUGUGGGAUCCGUCUCAGUUACUUUAU AGCCAUACCUGGUAUCUUA | 295 |
| miR-342 | GAAACUGGGCUCAAGGUGAGGGGUGCUAUCUGUGAUUG AGGGACAUGGUUAAUGGAAUUGUCUCACACAGAAAUCG CACCCGUCACCUUGGCCUACUUA | 296 |
| miR-345 | ACCCAAACCCUAGGUCUGCUGACUCCUAGUCCAGGGCUC GUGAUGGCUGGUGGGCCCUGAACGAGGGGUCUGGAGGC CUGGGUUUGAAUAUCGACAGC | 297 |
| miR-346 | GUCUGUCUGCCCGCAUGCCUGCCUCUCUGUUGCUCUGAA GGAGGCAGGGGCUGGGCCUGCAGCUGCCUGGGCAGAGCG GCUCCUGC | 298 |
| miR-367 | CCAUUACUGUUGCUAAUAUGCAACUCUGUUGAAUAUAA AUUGGAAUUGCACUUUAGCAAUGGUGAUGG | 299 |
| miR-368 | AAAAGGUGGAUAUUCCUUCUAUGUUUAUGUUAUUUAUG GUUAAACAUAGAGGAAAUUCCACGUUUU | 300 |
| miR-369 | UUGAAGGGAGAUCGACCGUGUUAUAUUCGCUUUAUUGA CUUCGAAUAAUACAUGGUUGAUCUUUUCUCAG | 301 |
| miR-370 | AGACAGAGAAGCCAGGUCACGUCUCUGCAGUUACACAGC UCACGAGUGCCUGCUGGGGUGGAACCUGGUCUGUCU | 302 |
| miR-371 | GUGGCACUCAAACUGUGGGGGCACUUUCUGCUCUCUGGU GAAAGUGCCGCCAUCUUUUGAGUGUUAC | 303 |
| miR-372 | GUGGGCCUCAAAUGUGGAGCACUAUUCUGAUGUCCAAG UGGAAAGUGCUGCGACAUUUGAGCGUCAC | 304 |
| miR-373 | GGGAUACUCAAAAUGGGGGCGCUUUCCUUUUUGUCUGU ACUGGGAAGUGCUUCGAUUUUGGGGUGUCCC | 305 |
| miR-374 | UACAUCGGCCAUUAUAAUACAACCUGAUAAGUGUUAUA GCACUUAUCAGAUUGUAUUGUAAUUGUCUGUGUA | 306 |
| mir-hes1 | AUGGAGCUGCUCACCCUGUGGGCCUCAAAUGUGGAGGA ACUAUUCUGAUGUCCAAGUGGAAAGUGCUGCGACAUUU GAGCGUCACCGGUGACGCCCAUAUCA | 307 |
| mir-hes2 | GCAUCCCCUCAGCCUGUGGCACUCAAACUGUGGGGGCAC UUUCUGCUCUCUGGUGAAAGUGCCGCCAUCUUUUGAGU GUUACCGCUUGAGAAGACUCAACC | 308 |
| mir-hes3 | CGAGGAGCUCAUACUGGGAUACUCAAAAUGGGGCGCU UUCCUUUUUGUCUGUUACUGGGAAGUGCUUCGAUUUUG GGGUGUCCCUGUUUGAGUAGGGCAUC | 309 |

*An underlined sequence within a precursor sequence corresponds to a mature processed miR transcript (see Table 1b). Some precursor sequences have two underlined sequences denoting two different mature miRs that are derived from the same precursor. All sequences are human.

TABLE 1b

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| let-7a | UGAGGUAGUAGGUUGUAUAGUU | 310 | let-7a-1; let-7a-2; let-7a-3; let-7a-4 |
| let-7b | UGAGGUAGUAGGUUGUGUGGUU | 311 | let-7b |
| let-7c | UGAGGUAGUAGGUUGUAUGGUU | 312 | let-7c |
| let-7d | AGAGGUAGUAGGUUGCAUAGU | 313 | let-7d; let-7d-v1 |
| let-7e | UGAGGUAGGAGGUUGUAUAGU | 314 | let-7e |
| let-7f | UGAGGUAGUAGAUUGUAUAGUU | 315 | let-7f-1; let-7f-2-1; let-7f-2-2 |
| let-7g | UGAGGUAGUAGUUUGUACAGU | 316 | let-7g |
| let-7i | UGAGGUAGUAGUUUGUGCU | 317 | let-7i |
| miR-1 | UGGAAUGUAAAGAAGUAUGUA | 318 | miR-1b; miR-1b-1; miR-1b-2 |
| miR-7 | UGGAAGACUAGUGAUUUUGUU | 319 | miR-7-1; miR-7-1a; miR-7-2; miR-7-3 |
| miR-9 | UCUUUGGUUAUCUAGCUGUAUGA | 320 | miR-9-1; miR-9-2; miR-9-3 |
| miR-9* | UAAAGCUAGAUAACCGAAAGU | 321 | miR-9-1; miR-9-2; miR-9-3 |
| miR-10a | UACCCUGUAGAUCCGAAUUUGUG | 322 | miR-10a |
| miR-10b | UACCCUGUAGAACCGAAUUUGU | 323 | miR-10b |
| miR-15a | UAGCAGCACAUAAUGGUUUGUG | 324 | miR-15a; miR-15a-2 |
| miR-15b | UAGCAGCACAUCAUGGUUUACA | 325 | miR-15b |
| miR-16 | UAGCAGCACGUAAAUAUUGGCG | 326 | miR-16-1; miR-16-2; miR-16-13 |
| miR-17-5p | CAAAGUGCUUACAGUGCAGGUAGU | 327 | miR-17 |
| miR-17-3p | ACUGCAGUGAAGGCACUUGU | 328 | miR-17 |
| miR-18 | UAAGGUGCAUCUAGUGCAGAUA | 329 | miR-18; miR-18-13 |
| miR-19a | UGUGCAAAUCUAUGCAAAACUGA | 330 | miR-19a; miR-19a-13 |
| miR-19b | UGUGCAAAUCCAUGCAAAACUGA | 331 | miR-19b-1; miR-19b-2 |
| miR-20 | UAAAGUGCUUAUAGUGCAGGUA | 332 | miR-20 (miR-20a) |
| miR-21 | UAGCUUAUCAGACUGAUGUUGA | 333 | miR-21; miR-21-17 |
| miR-22 | AAGCUGCCAGUUGAAGAACUGU | 334 | miR-22 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-23a | AUCACAUUGCCAGGGAUUUCC | 335 | miR-23a |
| miR-23b | AUCACAUUGCCAGGGAUUACCAC | 336 | miR-23b |
| miR-24 | UGGCUCAGUUCAGCAGGAACAG | 337 | miR-24-1; miR-24-2; miR-24-19; miR-24-9 |
| miR-25 | CAUUGCACUUGUCUCGGUCUGA | 338 | miR-25 |
| miR-26a | UUCAAGUAAUCCAGGAUAGGCU | 339 | miR-26a; miR-26a-1; miR-26a-2 |
| miR-26b | UUCAAGUAAUUCAGGAUAGGU | 340 | miR-26b |
| miR-27a | UUCACAGUGGCUAAGUUCCGCC | 341 | miR-27a |
| miR-27b | UUCACAGUGGCUAAGUUCUG | 342 | miR-27b-1; miR-27b-2 |
| miR-28 | AAGGAGCUCACAGUCUAUUGAG | 343 | miR-28 |
| miR-29a | CUAGCACCAUCUGAAAUCGGUU | 344 | miR-29a-2; miR-29a |
| miR-29b | UAGCACCAUUUGAAAUCAGU | 345 | miR-29b-1; miR-29b-2 |
| miR-29c | UAGCACCAUUUGAAAUCGGUUA | 346 | miR-29c |
| miR-30a-5p | UGUAAACAUCCUCGACUGGAAGC | 347 | miR-30a |
| miR-30a-3p | CUUUCAGUCGGAUGUUUGCAGC | 348 | miR-30a |
| miR-30b | UGUAAACAUCCUACACUCAGC | 349 | miR-30b-1; miR-30b-2 |
| miR-30c | UGUAAACAUCCUACACUCUCAGC | 350 | miR-30c |
| miR-30d | UGUAAACAUCCCCGACUGGAAG | 351 | miR-30d |
| miR-30e | UGUAAACAUCCUUGACUGGA | 352 | miR-30e |
| miR-31 | GGCAAGAUGCUGGCAUAGCUG | 353 | miR-31 |
| miR-32 | UAUUGCACAUUACUAAGUUGC | 354 | miR-32 |
| miR-33 | GUGCAUUGUAGUUGCAUUG | 355 | miR-33; miR-33b |
| miR-34a | UGGCAGUGUCUUAGCUGGUUGU | 356 | miR-34a |
| miR-34b | AGGCAGUGUCAUUAGCUGAUUG | 357 | miR-34b |
| miR-34c | AGGCAGUGUAGUUAGCUGAUUG | 358 | miR-34c |
| miR-92 | UAUUGCACUUGUCCCGGCCUGU | 359 | miR-92-2; miR-92-1 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-93 | AAAGUGCUGUUCGUGCAGGUAG | 360 | miR-93-1; miR-93-2 |
| miR-95 | UUCAACGGGUAUUUAUUGAGCA | 361 | miR-95 |
| miR-96 | UUUGGCACUAGCACAUUUUUGC | 362 | miR-96 |
| miR-98 | UGAGGUAGUAAGUUGUAUUGUU | 363 | miR-98 |
| miR-99a | AACCCGUAGAUCCGAUCUUGUG | 364 | miR-99a |
| miR-99b | CACCCGUAGAACCGACCUUGCG | 365 | miR-99b |
| miR-100 | UACAGUACUGUGAUAACUGAAG | 366 | miR-100 |
| miR-101 | UACAGUACUGUGAUAACUGAAG | 367 | miR-101-1; miR-101-2 |
| miR-103 | AGCAGCAUUGUACAGGGCUAUGA | 368 | miR-103-1 |
| miR-105 | UCAAAUGCUCAGACUCCUGU | 369 | miR-105 |
| miR-106-a | AAAAGUGCUUACAGUGCAGGUAGC | 370 | miR-106-a |
| miR-106-b | UAAAGUGCUGACAGUGCAGAU | 371 | miR-106-b |
| miR-107 | AGCAGCAUUGUACAGGGCUAUCA | 372 | miR-107 |
| miR-122a | UGGAGUGUGACAAUGGUGUUUGU | 373 | miR-122a-1; miR-122a-2 |
| miR-124a | UUAAGGCACGCGGUGAAUGCCA | 374 | miR-124a-1; miR-124a-2; miR-124a-3 |
| miR-125a | UCCCUGAGACCCUUUAACCUGUG | 375 | miR-125a-1; miR-125a-2 |
| miR-125b | UCCCUGAGACCCUAACUUGUGA | 376 | miR-125b-1; miR-125b-2 |
| miR-126* | CAUUAUUACUUUUGGUACGCG | 377 | miR-126-1; miR-126-2 |
| miR-126 | UCGUACCGUGAGUAAUAAUGC | 378 | miR-126-1; miR-126-2 |
| miR-127 | UCGGAUCCGUCUGAGCUUGGCU | 379 | miR-127-1; miR-127-2 |
| miR-128a | UCACAGUGAACCGGUCUCUUUU | 380 | miR-128; miR-128a |
| miR-128b | UCACAGUGAACCGGUCUCUUUC | 381 | miR-128b |
| miR-129 | CUUUUUGCGGUCUGGGCUUGC | 382 | miR-129-1; miR-129-2 |
| miR-130a | CAGUGCAAUGUUAAAAGGGC | 383 | miR-130a |
| miR-130b | CAGUGCAAUGAUGAAAGGGCAU | 384 | miR-130b |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-132 | UAACAGUCUACAGCCAUGGUCG | 385 | miR-132-1 |
| miR-133a | UUGGUCCCCUUCAACCAGCUGU | 386 | miR-133a-1; miR-133a-2 |
| miR-133b | UUGGUCCCCUUCAACCAGCUA | 387 | miR-133b |
| miR-134 | UGUGACUGGUUGACCAGAGGG | 388 | miR-134-1; miR-134-2 |
| miR-135a | UAUGGCUUUUUAUUCCUAUGUGA | 389 | miR-135a; miR-135a-2 (miR-135-2) |
| miR-135b | UAUGGCUUUUCAUUCCUAUGUG | 390 | miR-135b |
| miR-136 | ACUCCAUUUGUUUUGAUGAUGGA | 391 | miR-136-1; miR-136-2 |
| miR-137 | UAUUGCUUAAGAAUACGCGUAG | 392 | miR-137 |
| miR-138 | AGCUGGUGUUGUGAAUC | 393 | miR-138-1; miR-138-2 |
| miR-139 | UCUACAGUGCACGUGUCU | 394 | miR-139 |
| miR-140 | AGUGGUUUUACCCUAUGGUAG | 395 | miR-140; miR-140as; miR-140s |
| miR-141 | AACACUGUCUGGUAAAGAUGG | 396 | miR-141-1; miR-141-2 |
| miR-142-3p | UGUAGUGUUUCCUACUUUAUGGA | 397 | miR-142 |
| miR-142-5p | CAUAAAGUAGAAAGCACUAC | 398 | miR-142 |
| miR-143 | UGAGAUGAAGCACUGUAGCUCA | 399 | miR-143-1 |
| miR-144 | UACAGUAUAGAUGAUGUACUAG | 400 | miR-144-1; miR-144-2 |
| miR-145 | GUCCAGUUUUCCCAGGAAUCCCUU | 401 | miR-145-1; miR-145-2 |
| miR-146 | UGAGAACUGAAUUCCAUGGGUU | 402 | miR-146-1; miR-146-2 |
| miR-147 | GUGUGUGGAAAUGCUUCUGC | 403 | miR-147 |
| miR-148a | UCAGUGCACUACAGAACUUUGU | 404 | miR-148a (miR-148) |
| miR-148b | UCAGUGCAUCACAGAACUUUGU | 405 | miR-148b |
| miR-149 | UCUGGCUCCGUGUCUUCACUCC | 406 | miR-149 |
| miR-150 | UCUCCCAACCCUUGUACCAGUG | 407 | miR-150-1; miR-150-2 |
| miR-151 | ACUAGACUGAAGCUCCUUGAGG | 408 | miR-151 |
| miR-152 | UCAGUGCAUGACAGAACUUGG | 409 | miR-152-1; miR-152-2 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-153 | UUGCAUAGUCACAAAAGUGA | 410 | miR-153-1-1; miR-153-1-2; miR-153-2-1; miR-153-2-2 |
| miR-154 | UAGGUUAUCCGUGUUGCCUUCG | 411 | miR-154-1; miR-154-2 |
| miR-154* | AAUCAUACACGGUUGACCUAUU | 412 | miR-154-1; miR-154-2 |
| miR-155 | UUAAUGCUAAUCGUGAUAGGGG | 413 | miR-155 |
| miR-181a | AACAUUCAACGCUGUCGGUGAGU | 414 | miR-181a |
| miR-181b | AACAUUCAUUGCUGUCGGUGGGUU | 415 | miR-181b-1; miR-181b-2 |
| miR-181c | AACAUUCAACCUGUCGGUGAGU | 416 | miR-181c |
| miR-182 | UUUGGCAAUGGUAGAACUCACA | 417 | miR-182; miR-182as |
| miR-182* | UGGUUCUAGACUUGCCAACUA | 418 | miR-182; miR-182as |
| miR-183 | UAUGGCACUGGUAGAAUUCACUG | 419 | miR-183 |
| miR-184 | UGGACGGAGAACUGAUAAGGGU | 420 | miR-184-1; miR-184-2 |
| miR-185 | UGGAGAGAAAGGCAGUUC | 421 | miR-185-1; miR-185-2 |
| miR-186 | CAAAGAAUUCUCCUUUUGGGCUU | 422 | miR-186-1; miR-186-2 |
| miR-187 | UCGUGUCUUGUGUUGCAGCCG | 423 | miR-187 |
| miR-188 | CAUCCCUUGCAUGGUGGAGGGU | 424 | miR-188 |
| miR-189 | GUGCCUACUGAGCUGAUAUCAGU | 425 | miR-189-1; miR-189-2 |
| miR-190 | UGAUAUGUUUGAUAUAUUAGGU | 426 | miR-190-1; miR-190-2 |
| miR-191 | CAACGGAAUCCCAAAAGCAGCU | 427 | miR-191-1; miR-191-2 |
| miR-192 | CUGACCUAUGAAUUGACAGCC | 428 | miR-192 |
| miR-193 | AACUGGCCUACAAAGUCCCAG | 429 | miR-193-1; miR-193-2 |
| miR-194 | UGUAACAGCAACUCCAUGUGGA | 430 | miR-194-1; miR-194-2 |
| miR-195 | UAGCAGCACAGAAAUAUUGGC | 431 | miR-195-1; miR-195-2 |
| miR-196a | UAGGUAGUUUCAUGUUGUUGG | 432 | miR-196a; miR-196a-2 (miR196- |
| miR-196b | UAGGUAGUUUCCUGUUGUUGG | 433 | miR-196b |
| miR-197 | UUCACCACCUUCUCCACCCAGC | 434 | miR-197 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-198 | GGUCCAGAGGGGAGAUAGG | 435 | miR-198 |
| miR-199a | CCCAGUGUUCAGACUACCUGUUC | 436 | miR-199a-1; miR-199a-2 |
| miR-199a* | UACAGUAGUCUGCACAUUGGUU | 437 | miR-199a-1; miR-199a-2; miR-199s; miR-199b |
| miR-199b | CCCAGUGUUUAGACUAUCUGUUC | 438 | miR-199b |
| miR-200a | UAACACUGUCUGGUAACGAUGU | 439 | miR-200a |
| miR-200b | CUCUAAUACUGCCUGGUAAUGAUG | 440 | miR-200b |
| miR-200c | AAUACUGCCGGGUAAUGAUGGA | 441 | miR-200c |
| miR-202 | AGAGGUAUAGGGCAUGGGAAGA | 442 | miR-202 |
| miR-203 | GUGAAAUGUUUAGGACCACUAG | 443 | miR-203 |
| miR-204 | UUCCCUUUGUCAUCCUAUGCCU | 444 | miR-204 |
| miR-205 | UCCUUCAUUCCACCGGAGUCUG | 445 | miR-205 |
| miR-206 | UGGAAUGUAAGGAAGUGUGUGG | 446 | miR-206-1; miR-206-2 |
| miR-208 | AUAAGACGAGCAAAAAGCUUGU | 447 | miR-208 |
| miR-210 | CUGUGCGUGUGACAGCGGCUG | 448 | miR-210 |
| miR-211 | UUCCCUUUGUCAUCCUUCGCCU | 449 | miR-211 |
| miR-212 | UAACAGUCUCCAGUCACGGCC | 450 | miR-212 |
| miR-213 | ACCAUCGACCGUUGAUUGUACC | 451 | miR-213 |
| miR-214 | ACAGCAGGCACAGACAGGCAG | 452 | miR-214 |
| miR-215 | AUGACCUAUGAAUUGACAGAC | 453 | miR-215 |
| miR-216 | UAAUCUCAGCUGGCAACUGUG | 454 | miR-216 |
| miR-217 | UACUGCAUCAGGAACUGAUUGGAU | 455 | miR-217 |
| miR-218 | UUGUGCUUGAUCUAACCAUGU | 456 | miR-218-1; miR-218-2 |
| miR-219 | UGAUUGUCCAAACGCAAUUCU | 457 | miR-219; miR-219-1; miR-219-2 |
| miR-220 | CCACACCGUAUCUGACACUUU | 458 | miR-220 |
| miR-221 | AGCUACAUUGUCUGCUGGGUUUC | 459 | miR-221 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-222 | AGCUACAUCUGGCUACUGGGUCUC | 460 | miR-222 |
| miR-223 | UGUCAGUUUGUCAAAUACCCC | 461 | miR-223 |
| miR-224 | CAAGUCACUAGUGGUUCCGUUUA | 462 | miR-224 |
| miR-296 | AGGGCCCCCCCUCAAUCCUGU | 463 | miR-296 |
| miR-299 | UGGUUUACCGUCCCACAUACAU | 464 | miR-299 |
| miR-301 | CAGUGCAAUAGUAUUGUCAAAGC | 465 | miR-301 |
| miR-302a | UAAGUGCUUCCAUGUUUUGGUGA | 466 | miR-302a |
| miR-302b* | ACUUUAACAUGGAAGUGCUUUCU | 467 | miR-302b |
| miR-302b | UAAGUGCUUCCAUGUUUUAGUAG | 468 | miR-302b |
| miR-302c* | UUUAACAUGGGGGUACCUGCUG | 469 | miR-302c |
| miR-302c | UAAGUGCUUCCAUGUUUCAGUGG | 470 | miR-302c |
| miR-302d | UAAGUGCUUCCAUGUUUGAGUGU | 471 | miR-302d |
| miR-320 | AAAAGCUGGGUUGAGAGGGCGAA | 472 | miR-320 |
| miR-321 | UAAGCCAGGGAUUGUGGGUUC | 473 | miR-321 |
| miR-323 | GCACAUUACACGGUCGACCUCU | 474 | miR-323 |
| miR-324-5p | CGCAUCCCCUAGGGCAUUGGUGU | 475 | miR-324 |
| miR-324-3p | CCACUGCCCCAGGUGCUGCUGG | 476 | miR-324 |
| miR-325 | CCUAGUAGGUGUCCAGUAAGU | 477 | miR-325 |
| miR-326 | CCUCUGGGCCCUUCCUCCAG | 478 | miR-326 |
| miR-328 | CUGGCCCUCUCUGCCCUUCCGU | 479 | miR-328 |
| miR-330 | GCAAAGCACACGGCCUGCAGAGA | 480 | miR-330 |
| miR-331 | GCCCCUGGGCCUAUCCUAGAA | 481 | miR-331 |
| miR-335 | UCAAGAGCAAUAACGAAAAAUGU | 482 | miR-335 |
| miR-337 | UCCAGCUCCUAUAUGAUGCCUUU | 483 | miR-337 |
| miR-338 | UCCAGCAUCAGUGAUUUUGUUGA | 484 | miR-338 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-339 | UCCCUGUCCUCCAGGAGCUCA | 485 | miR-339 |
| miR-340 | UCCGUCUCAGUUACUUUAUAGCC | 486 | miR-340 |
| miR-342 | UCUCACACAGAAAUCGCACCCGUC | 487 | miR-342 |
| miR-345 | UGCUGACUCCUAGUCCAGGGC | 488 | miR-345 |
| miR-346 | UGUCUGCCCGCAUGCCUGCCUCU | 489 | miR-346 |
| miR-367 | AAUUGCACUUUAGCAAUGGUGA | 490 | miR-367 |
| miR-368 | ACAUAGAGGAAAUUCCACGUUU | 491 | miR-368 |
| miR-369 | AAUAAUACAUGGUUGAUCUUU | 492 | miR-369 |
| miR-370 | GCCUGCUGGGGUGGAACCUGG | 493 | miR-370 |
| miR-371 | GUGCCGCCAUCUUUUGAGUGU | 494 | miR-371 |
| miR-372 | AAAGUGCUGCGACAUUUGAGCGU | 495 | miR-372 |
| miR-373* | ACUCAAAAUGGGGCGCUUUCC | 496 | miR-373 |
| miR-373 | GAAGUGCUUCGAUUUUGGGGUGU | 497 | miR-373 |
| miR-374 | UUAUAAUACAACCUGAUAAGUG | 498 | miR-374 |

The present invention encompasses methods of diagnosing or prognosticating whether a subject has, or is at risk for developing, a cancer and/or myeloproliferative disorder. The methods comprise determining the level of at least one miR gene product in a sample from the subject and comparing the level of the miR gene product in the sample to a control. As used herein, a "subject" can be any mammal that has, or is suspected of having, a cancer and/or myeloproliferative disorder. In a preferred embodiment, the subject is a human who has, or is suspected of having, a cancer, myeloproliferative disorder and/or a platelet disorder.

The level of at least one miR gene product can be measured in cells of a biological sample obtained from the subject. For example, a tissue sample can be removed from a subject suspected of having cancer and/or a myeloproliferative disorder by conventional biopsy techniques. In another embodiment, a blood sample can be removed from the subject, and white blood cells can be isolated for DNA extraction by standard techniques. In one embodiment, the blood or tissue sample is obtained from the subject prior to initiation of radiotherapy, chemotherapy or other therapeutic treatment. A corresponding control tissue or blood sample, or a control reference sample (e.g., obtained from a population of control samples), can be obtained from unaffected tissues of the subject, from a normal human individual or population of normal individuals, or from cultured cells corresponding to the majority of cells in the subject's sample. The control tissue or blood sample can then processed along with the sample from the subject, so that the levels of miR gene product produced from a given miR gene in cells from the subject's sample can be compared to the corresponding miR gene product levels from cells of the control sample. Alternatively, a reference sample can be obtained and processed separately (e.g., at a different time) from the test sample and the level of a miR gene product produced from a given miR gene in cells from the test sample can be compared to the corresponding miR gene product level from the reference sample.

In one embodiment, the level of the at least one miR gene product in the test sample is greater than the level of the corresponding miR gene product in the control sample (i.e., expression of the miR gene product is "upregulated"). As used herein, expression of a miR gene product is "upregulated" when the amount of miR gene product in a cell or tissue sample from a subject is greater than the amount of the same gene product in a control (e.g., a reference standard, a control cell sample, a control tissue sample). In another embodiment, the level of the at least one miR gene product in the test sample is less than the level of the corresponding miR gene product in the control sample (i.e., expression of the miR gene product is "downregulated"). As used herein, expression of a miR gene is "downregulated" when the amount of miR gene product produced from that gene in a cell or tissue sample from a subject is less than the amount produced from the same gene in a control cell or tissue sample. The relative miR gene expression in the control and normal samples can be determined with respect to one or more RNA expression standards. The standards can comprise, for example, a zero miR gene expression level, the miR gene expression level in a standard cell line, the miR gene expression level in unaffected tissues of the subject, or the average level of miR gene expression previously obtained for a population of normal human controls (e.g., a control reference standard).

An alteration (i.e., an increase or decrease) in the level of a miR gene product in the sample obtained from the subject, relative to the level of a corresponding miR gene product in a control sample, is indicative of the presence of cancer and/or a myeloproliferative disorder in the subject. In one embodiment, the level of the at least one miR gene product in the test sample is greater than the level of the corresponding miR gene product in the control sample. miR gene products having higher expression levels in cancer cell lines (e.g., AMKL cell lines) than control cells (e.g., in vitro $CD34^+$-differentiated megakaryocytes) are described and exemplified herein (see, e.g., Example 5). In one embodiment, the at least one miR gene product is selected from the group consisting of miR-101, miR-126, miR-99a, miR-99-prec, miR-106, miR-339, miR-99b, miR-149, miR-33, miR-135, miR-20 and combinations thereof. In another embodiment, the at least one miR gene product is selected from the group consisting of miR-101, miR-126, miR-106, miR-20 and miR-135 and combinations thereof. In yet another embodiment, the at least one miR gene product is selected from the group consisting of miR-106, miR-20 and miR-135 and combinations thereof. As described and exemplified herein, the increased expression of such miR gene products discriminates cancerous cells from corresponding non-cancerous cells.

As described herein, the diagnostic and prognostic methods of the invention can be used to diagnose or prognosticate cancers and/or myeloproliferative disorders. In particular embodiments, the diagnostic and prognostic methods are used to diagnose or prognosticate a cancer in a subject, tissue sample, cell sample or fluid sample. The diagnostic and prognostic methods can be used to diagnose or prognosticate any type of cancer. In particular embodiments, the diagnostic and prognostic methods can be used to diagnose or prognosticate a leukemia. In one embodiment, the leukemia that is diagnosed or prognosticated is acute myeloid leukemia (e.g., acute megakaryoblastic leukemia). In other embodiments, the diagnostic and prognostic methods can be used to diagnose or prognosticate multiple myeloma.

The diagnostic and prognostic methods of the invention can also be used to diagnose or prognosticate hematologic malignancies (e.g., myeloproliferative disorders). In one embodiment, the myeloproliferative disorder that is diagnosed or prognosticated is selected from the group consisting of essential thrombocytemia (ET), polycythemia vera (PV), myelodisplasia, myelofibrosis (e.g., agnogenic myeloid metaplasia (AMM) (also referred to as idiopathic myelofibrosis)) and chronic myelogenous leukemia (CML).

In particular embodiments, the diagnostic, prognostic and therapeutic methods of the invention can also be used to diagnose, prognosticate and/or treat platelet disorders (e.g., inherited platelet disorders). For example, the diagnostic, prognostic and therapeutic methods can be used to diagnose, prognosticate and/or treat defects in platelet-vessel wall interactions (i.e., disorders of adhesion). Such adhesion disorders include, e.g., von Willebrand disease (deficiency or defect in plasma vWF) and Bernard-Soulier syndrome (deficiency or defect in GPIb). In other embodiments, the diagnostic, prognostic and therapeutic methods can be used to diagnose, prognosticate and/or treat defects in platelet-platelet interaction (i.e., disorders of aggregation). Such aggregation disorders include, e.g., congenital afibrinogenemia (deficiency of plasma fibrinogen) and glanzmann thrombasthenia (deficiency or defect in GPIIb-IIIa). In other embodiments, the diagnostic, prognostic and therapeutic methods can be used to diagnose, prognosticate and/or treat disorders of platelet secretion and abnormalities of granules. Such disorders of platelet secretion and abnormalities of granules include, e.g., storage pool deficiency and Quebec platelet disorder. In yet other embodiments, the diagnostic, prognostic and therapeutic methods can be used to diagnose, prognosticate and/or treat disorders of platelet secretion and signal transduction (primary secretion defects). Such primary secretion defects include, e.g., defects in platelet-agonist interaction (receptor defects) (e.g., thromboxane $A_2$, collagen, ADP, epinephrine), defects in G-protein activation (e.g., G$\alpha$q deficiency, G$\alpha$s abnormalities, G$\alpha$i deficiency), defects in phosphatidylinositol metabolism (e.g., phospholipase C-2 deficiency), defects in calcium mobilization, defects in protein phosphorylation (pleckstrin) PKC-y deficiency, and abnormalities in arachidonic acid pathways and thromboxane synthesis (e.g., cyclooxygenase deficiency, thromboxane synthase deficiency). In other embodiments, the diagnostic, prognostic and therapeutic methods can be used to diagnose, prognosticate and/or treat defects in cytoskeletal regulation (e.g., Wiskott-Aldrich syndrome). In still other embodiments, the diagnostic, prognostic and therapeutic methods can be used to diagnose, prognosticate and/or treat disorders of platelet coagulant-protein interaction (membrane phospholipid defects) (e.g., Scott syndrome). Other platelet disorders (e.g., inherited platelet disorders) can also be diagnosed, prognosticated and/or treated using the methods of the invention.

The invention also provides methods of determining the prognosis of a subject with cancer and/or a myeloproliferative disorder. In this method, the level of at least one miR gene product, which is associated with a particular prognosis in cancer and/or a myeloproliferative disorder (e.g., a good or positive prognosis, a poor or adverse prognosis), is measured in a test sample from the subject. An alteration (e.g., an increase, a decrease) in the level of the miR gene product in the test sample, relative to the level of a corresponding miR gene product in a control sample, is indicative of the subject having a cancer and/or myeloproliferative disorder with a particular prognosis. In one embodiment, the miR gene product is associated with an adverse (i.e., poor) prognosis. Examples of an adverse prognosis include, but are not limited to, low survival rate and rapid disease progression. In one embodiment, the level of the at least one miR gene product in the test sample is greater than the level of the corresponding miR gene product in a control sample (i.e., it is upregulated). In a particular embodiment, the at least one miR gene product that is upregulated is selected from the group consisting of miR-101, miR-126, miR-99a, miR-99-prec, miR-106, miR-339, miR-99b, miR-149, miR-33, miR-135, miR-20 and combinations thereof. In another embodiment, the at least one miR gene product that is upregulated is selected from the group consisting of miR-101, miR-126, miR-106, miR-20 and miR-135 and combinations thereof. In yet another embodiment, the at least one miR gene product that is upregulated is selected from the group consisting of miR-106, miR-20 and miR-135 and combinations thereof. The increased expression of such miR gene products can correlate with an adverse prognosis and the severity of a subject's cancer and/or myeloproliferative disorder.

In certain embodiments of the diagnostic and prognostic methods described herein, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

Identification of targets of particular miR gene products (e.g., those miR gene products exhibiting upregulated or downregulated expression relative to a control sample) can aid in elucidating mechanisms of action of microRNAs. As described and exemplified herein, particular targets and putative targets of select microRNAs were identified (see, e.g., Tables 2, 3 and 5 and Exemplification). For example, the transcription factor MAFB was identified as a target of mi-130a (Example 2). Similarly, HOXA1 was identified as a target of miR-10a (Example 5). For both miRs, direct interaction of the miR with the 3' UTR of its respective target was demonstrated (Examples 2 and 5). Moreover, an inverse relation in the expression of the miR and its respective target were demonstrated. Thus, expression of pre-miR-130a resulted in decreased expression of MAFB (see, e.g., FIG. 2C) while expression of pre-miR-10a resulted in decreased expression of HOXA1 (see, e.g., FIGS. 3C, 3F and 3G). Thus, in one embodiment, expression of target genes of particular microRNAs (e.g., those listed in Tables 2, 3 and 5) can be used to diagnose cancer and/or a myeloproliferative disorder. Such target genes display inverse expression to the respective miR that targets it. One of skill in the art can measure the expression levels of any of these target genes using known methods and/or methods described herein for measuring the expression levels of microRNAs (e.g., quantitative or semi-quantitative RT-PCR, Northern blot analysis, solution hybridization detection, microarray analysis), without undue experimentation. In particular embodiments, the target gene that is measured is MAFB or HOXA1.

The level of the at least one miR gene product can be measured using a variety of techniques that are well known to those of skill in the art (e.g., quantitative or semi-quantitative RT-PCR, Northern blot analysis, solution hybridization detection). In a particular embodiment, the level of at least one miR gene product is measured by reverse transcribing RNA from a test sample obtained from the subject to provide a set of target oligodeoxynucleotides, hybridizing the target oligodeoxynucleotides to one or more miRNA-specific probe oligonucleotides (e.g., a microarray that comprises miRNA-specific probe oligonucleotides) to provide a hybridization profile for the test sample, and comparing the test sample hybridization profile to a hybridization profile generated from a control sample. An alteration in the signal of at least one miRNA in the test sample relative to the control sample is indicative of the subject either having, or being at risk for developing cancer and/or a myeloproliferative disorder. In one embodiment, the signal of at least one miRNA is upregulated, relative to the signal generated from the control sample. In another embodiment, the signal of at least one miRNA is downregulated, relative to the signal generated from the control sample. In a particular embodiment, the microarray comprises miRNA-specific probe oligonucleotides for a substantial portion of all known human miRNAs (e.g., the miRNAs listed in Tables 1a and 1b plus other known or discovered miRNAs). In a further embodiment, the microarray comprises miRNA-specific probe oligonucleotides for one or more miRNAs selected from the group consisting of miR-101, miR-126, miR-99a, miR-99-prec, miR-106, miR-339, miR-99b, miR-149, miR-33, miR-135, miR-20 and a combination thereof. In one embodiment, the microarray comprises miRNA-specific probe oligonucleotides for one or more miRNAs selected from the group consisting of miR-101, miR-126, miR-106, miR-20, miR-135 and a combination thereof.

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs and other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75× TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample. According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 µg of total RNA. The relatively limited number of miRNAs (a few hundred per species) allows the construction of a common microarray for several species, with distinct oligonucleotide probes for each. Such a tool would allow for analysis of trans-species expression for each known miR under various conditions.

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having a cancer and/or a myeloproliferative disorder is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal (e.g., noncancerous, non-myeloproliferative disorder) control sample or reference sample. An alteration in the signal is indicative of the presence of, or propensity to develop, cancer in the subject.

Other techniques for measuring miR gene expression are also within the skill in the art, and include various techniques for measuring rates of RNA transcription and degradation.

The invention also provides methods of diagnosing whether a subject has, or is at risk for developing, a cancer and/or myeloproliferative disorder with an adverse prognosis. In this method, the level of at least one miR gene product, which is associated with an adverse prognosis in a cancer and/or myeloproliferative disorder, is measured by reverse transcribing RNA from a test sample obtained from the subject to provide a set of target oligodeoxynucleotides. The target oligodeoxynucleotides are then hybridized to one or more miRNA-specific probe oligonucleotides (e.g., a microarray that comprises miRNA-specific probe oligonucleotides) to provide a hybridization profile for the test sample, and the test sample hybridization profile is compared to a hybridization profile generated from a control sample. An alteration in the signal of at least one miRNA in the test sample relative to the control sample is indicative of the subject either having, or being at risk for developing, a cancer and/or myeloproliferative disorder with an adverse prognosis. miRs suitable for use in this method include, e.g., those that are upregulated in cancerous cells (e.g., AMKL cells).

In particular embodiments of the diagnostic, prognostic and therapeutic methods of the invention, as well as the pharmaceutical compositions of the invention, the miR gene product is not one or more of let7a-2, let-7c, let-7g, let-7i, miR-7-2, miR-7-3, miR-9, miR-9-1, miR-10a, miR-15a, miR-15b, miR-16-1, miR-16-2, miR-17-5p, miR-20a, miR-21, miR-24-1, miR-24-2, miR-25, miR-29b-2, miR-30, miR-30a-5p, miR-30c, miR-30d, miR-31, miR-32, miR-34, miR-34a, miR-34a prec, miR-34a-1, miR-34a-2, miR-92-2, miR-96, miR-99a, miR-99b prec, miR-100, miR-103, miR-106a, miR-107, miR-123, miR-124a-1, miR-125b-1, miR-125b-2, miR-126*, miR-127, miR-128b, miR-129, miR-129-1/2 prec, miR-132, miR-135-1, miR-136, miR-137, miR-141, miR-142-as, miR-143, miR-146, miR-148, miR-149, miR-153, miR-155, miR 159-1, miR-181, miR-181b-1, miR-182, miR-186, miR-191, miR-192, miR-195, miR-196-1, miR-196-1 prec, miR-196-2, miR-199a-1, miR-199a-2, miR-199b, miR-200b, miR-202, miR-203, miR-204, miR-205, miR-210, miR-211, miR-212, miR-214, miR-215, miR-217, miR-221 and/or miR-223.

As described herein, the level of a miR gene product in a sample can be measured using any technique that is suitable for detecting RNA expression levels in a biological sample. Suitable techniques (e.g., Northern blot analysis, RT-PCR, in situ hybridization) for determining RNA expression levels in a biological sample (e.g., cells, tissues) are well known to those of skill in the art. In a particular embodiment, the level of at least one miR gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes (e.g., DNA probes, RNA probes) for Northern blot hybridization of a given miR gene product can be produced from the nucleic acid sequences provided in Table 1a and Table 1b and include, but are not limited to, probes having at least about 70%, 75%, 80%, 85%, 90%, 95%, 98% or 99% complementarity to a miR gene product of interest, as well as probes that have complete complementarity to a miR gene product of interest. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference.

For example, the nucleic acid probe can be labeled with, e.g., a radionuclide, such as $^3H$, $^{32}P$, $^{33}P$, $^{14}C$, or $^{35}S$; a heavy metal; a ligand capable of functioning as a specific binding pair member for a labeled ligand (e.g., biotin, avidin or an antibody); a fluorescent molecule; a chemiluminescent molecule; an enzyme or the like.

Probes can be labeled to high specific activity by either the nick translation method of Rigby et al. (1977), *J. Mol. Biol.* 113:237-251 or by the random priming method of Fienberg et al. (1983), *Anal. Biochem.* 132:6-13, the entire disclosures of which are incorporated herein by reference. The latter is the method of choice for synthesizing $^{32}P$-labeled probes of high specific activity from single-stranded DNA or from RNA templates. For example, by replacing preexisting nucleotides with highly radioactive nucleotides according to the nick translation method, it is possible to prepare $^{32}P$-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such as the *Molecular Dynamics* 400-*B 2D Phosphorimager* available from Amersham Biosciences, Piscataway, N.J.

Where radionuclide labeling of DNA or RNA probes is not practical, the random-primer method can be used to incorporate an analogue, for example, the dTTP analogue 5-(N-(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miR gene product can be produced from the nucleic acid sequences provided in Table 1 a and Table 1b, and include, but are not limited to, probes having at least about 70%, 75%, 80%, 85%, 90%, 95%, 98% or 99% complementarity to a miR gene product of interest, as well as probes that have complete complementarity to a miR gene product of interest, as described above.

The relative number of miR gene transcripts in cells can also be determined by reverse transcription of miR gene transcripts, followed by amplification of the reverse-transcribed transcripts by polymerase chain reaction (RT-PCR), for example, as exemplified herein. The levels of miR gene transcripts can be quantified in comparison with an internal standard, for example, the level of mRNA from a "housekeeping" gene present in the same sample. A suitable "housekeeping" gene for use as an internal standard includes, e.g., U6 small nuclear RNA, myosin or glyceraldehyde-3-phosphate dehydrogenase (G3PDH). Methods for performing quantitative and semi-quantitative RT-PCR, and variations thereof, are well known to those of skill in the art.

In some instances, it may be desirable to simultaneously determine the expression level of a plurality of different miR gene products in a sample. In other instances, it may be desirable to determine the expression level of the transcripts of all known miR genes correlated with a cancer and/or myeloproliferative disorder. Assessing cancer-specific expression levels for hundreds of miR genes or gene products is time consuming and requires a large amount of total RNA (e.g., at least 20 µg for each Northern blot) and autoradiographic techniques that require radioactive isotopes.

To overcome these limitations, an oligolibrary, in microchip format (i.e., a microarray), may be constructed containing a set of oligonucleotide (e.g., oligodeoxynucleotide) probes that are specific for a set of miR genes. Using such a microarray, the expression level of multiple microRNAs in a biological sample can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microRNAs have an altered expression level in cancer cells and/or cells exhibiting a myeloproliferative disorder. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for a miR" is meant a probe oligonucleotide that has a sequence selected to hybridize to a specific miR gene product, or to a reverse transcript of the specific miR gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue, cell or fluid samples may be distinguished from corresponding cancerous and/or myeloproliferative disorder-exhibiting tissue, cell or fluid samples. Within cancerous and/or myeloproliferative disorder-exhibiting tissue, cell or fluid samples, different prognosis states (for example, good or poor long term survival prospects) may be determined. By comparing expression profiles of cancerous and/or myeloproliferative disorder-exhibiting tissue, cell or fluid samples in different states, information regarding which genes are important (including both upregulation and downregulation of genes) in each of these states is obtained. The identification of sequences that are differentially expressed in cancerous and/or myeloproliferative disorder-exhibiting tissue, cell or fluid samples, as well as differential expression resulting in different prognostic outcomes, allows the use of this information in a number of ways. For example, a particular treatment regime may be evaluated (e.g., to determine whether a chemotherapeutic drug acts to improve the long-term prognosis in a particular subject). Similarly, diagnosis may be done or confirmed by comparing samples from a subject with known expression profiles. Furthermore, these gene expression profiles (or individual genes) allow screening of drug candidates that suppress the cancer and/or myeloproliferative disorder expression profile or convert a poor prognosis profile to a better prognosis profile.

Without wishing to be bound by any one theory, it is believed that alterations in the level of one or more miR gene products in cells can result in the deregulation of one or more intended targets for these miRs, which can lead to aberrant megakaryocytic differentiation and/or the formation of cancer, a myeloproliferative disorder and/or a platelet disorder. Therefore, altering the level of the miR gene product (e.g., by decreasing the level of a miR that is upregulated in cancerous and/or myeloproliferative disorder-exhibiting cells, by increasing the level of a miR that is downregulated in cancerous and/or myeloproliferative disorder-exhibiting cells) may successfully treat the cancer, myeloproliferative disorder and/or platelet disorder.

Accordingly, the present invention encompasses methods of treating a cancer and/or myeloproliferative disorder in a subject, wherein at least one miR gene product is deregulated (e.g., downregulated, upregulated) in the cells (e.g., cancerous cells and/or myeloproliferative disorder-exhibiting cells) of the subject. In one embodiment, the level of at least one miR gene product in a test sample (e.g., a sample comprising cancerous and/or myeloproliferative disorder-exhibiting tissues, cells or fluid) is greater than the level of the corresponding miR gene product in a control or reference sample. In another embodiment, the level of at least one miR gene product in a test sample (e.g., a sample comprising cancerous and/or myeloproliferative disorder-exhibiting tissues, cells or fluid) is less than the level of the corresponding miR gene product in a control sample. When the at least one isolated miR gene product is downregulated in the test sample (e.g., a sample comprising cancerous and/or myeloproliferative disorder-exhibiting tissues, cells or fluid), the method comprises administering an effective amount of the at least one isolated miR gene product, or an isolated variant or biologically-active fragment thereof, such that proliferation of the cancerous and/or myeloproliferative disorder-exhibiting cells in the subject is inhibited. For example, when a miR gene product is downregulated in a cancer cell in a subject, administering an effective amount of an isolated miR gene product to the subject can inhibit proliferation of the cancer cell. The isolated miR gene product that is administered to the subject can be identical to an endogenous wild-type miR gene product (e.g., a miR gene product shown in Table 1a or Table 1b) that is downregulated in the cancer cell or it can be a variant or biologically-active fragment thereof. As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e.g., inhibiting translation of a target RNA molecule, modulating the stability of a target RNA molecule, inhibiting processing of a target RNA molecule) and inhibition of a cellular process associated with cancer and/or a myeloproliferative disorder (e.g., cell differentiation, cell growth, cell death). These variants include species variants and variants that are the consequence of one or more mutations (e.g., a substitution, a deletion, an insertion) in a miR gene. In certain embodiments, the variant is at least about 70%, 75%, 80%, 85%, 90%, 95%, 98%, or 99% identical to a corresponding wild-type miR gene product.

As defined herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with cancer and/or a myeloproliferative disorder. In certain embodiments, the biologically-active fragment is at least about 5, 7, 10, 12, 15, or 17 nucleotides in length. In a particular embodiment, an isolated miR gene product can be administered to a subject in combination with one or more additional anti-cancer treatments. Suitable anti-cancer treatments include, but are not limited to, chemotherapy, radiation therapy and combinations thereof (e.g., chemoradiation).

When the at least one isolated miR gene product is upregulated in the cancer cells, the method comprises administering to the subject an effective amount of a compound that inhibits expression of the at least one miR gene product, such that proliferation of the cancer and/or myeloproliferative disorder-exhibiting cells is inhibited. Such compounds are referred to herein as miR gene expression-inhibition compounds. Examples of suitable miR gene expression-inhibition compounds include, but are not limited to, those described herein (e.g., double-stranded RNA, antisense nucleic acids and enzymatic RNA molecules). In a particular embodiment, a miR gene expression-inhibiting compound can be administered to a subject in combination with one or more additional anti-cancer treatments. Suitable anti-cancer treatments include, but are not limited to, chemotherapy, radiation therapy and combinations thereof (e.g., chemoradiation).

As described, when the at least one isolated miR gene product is upregulated in cancer cells (e.g., AMKL cells), the method comprises administering to the subject an effective amount of at least one compound for inhibiting expression of the at least one miR gene product, such that proliferation of cancer cells is inhibited. In one embodiment, the compound for inhibiting expression of the at least one miR gene product inhibits a miR gene product selected from the group consisting of miR-101, miR-126, miR-99a, miR-99-prec, miR-106, miR-339, miR-99b, miR-149, miR-33, miR-135, miR-20 and a combination thereof. In another embodiment, the compound for inhibiting expression of the at least one miR gene product inhibits a miR gene product selected from the group consisting of miR-101, miR-126, miR-106, miR-20, miR-135 and a combination thereof. In yet another embodiment, the compound for inhibiting expression of the at least one miR gene product inhibits a miR gene product selected from the group consisting of miR-106, miR-20, miR-135 and a combination thereof.

As described and exemplified herein, the transcription factor MAFB, which is upregulated in megakaryocytic differentiation, is a target of miR-130a. Moreover, an inverse relation in the expression of miR-130a and its respective target were demonstrated. Thus, expression of pre-miR-130a resulted in decreased expression of MAFB (see, e.g., FIG. 2C). MAFB is known to be deregulated in cancer (e.g., multiple myeloma and acute myeloid leukemia). For example, ectopic expression of MAFB has been observed in human myeloma cells carrying (14;20)(q32;q11) chromosomal translocations (Hanamura, I., et al. (2001) *Jpn. J. Cancer Res.* 92(6):638-644 (2001)). Accordingly, in one embodiment, the invention is a method of treating a cancer and/or myeloproliferative disorder in a subject comprising administering an effective amount of at least one miR gene product or an isolated variant or biologically-active fragment thereof to the subject, wherein:

the cancer and/or myeloproliferative disorder is associated with overexpression of a MAFB gene product; and the at least one miR gene product binds to, and decreases expression of, the MAFB gene product.

In one embodiment, the at least one miR gene product or isolated variant or biologically-active fragment thereof comprises a nucleotide sequence that is complementary to a nucleotide sequence in the MAFB gene product (e.g., complementary to the 3' UTR of MAFB). In a particular embodiment, the at least one miR gene product is miR-130a or an isolated variant or biologically-active fragment thereof.

Also as described and exemplified herein, mRNA of HOXA1, one of the members of the HOX family of proteins, is upregulated 7-fold in megakaryocytic differentiation (see, e.g., Example 4). Moreover, HOXA1 is a target of miR-10a and its expression is inversely related to the expression of miR-10a. Thus, expression of pre-miR-10a resulted in decreased expression of HOXA1 (see, e.g., FIGS. 3C, 3F and 3G). HOXA1. Expression of HOXA1 has been demonstrated to be sufficient to result in the oncogenic transformation of immortalized human mammary epithelial cells with aggressive in vivo tumor formation (Zhang, X., et al., (2002) *J. Biol. Chem.* 278(9):7580-7590). Further, forced expression of HOXA1 in mammary carcinoma cells, in a Bcl-2-dependent manner, resulted in a dramatic enhancement of anchorage-independent proliferation and colony formation in soft agar. Id. Accordingly, in one embodiment, the invention is a method of treating a cancer and/or myeloproliferative disorder in a subject comprising administering an effective amount of at least one miR gene product or an isolated variant or biologically-active fragment thereof to the subject, wherein:

the cancer and/or myeloproliferative disorder is associated with overexpression of a HOXA1 gene product; and the at least one miR gene product binds to, and decreases expression of, the HOXA1 gene product.

In one embodiment, the at least one miR gene product or isolated variant or biologically-active fragment thereof comprises a nucleotide sequence that is complementary to a nucleotide sequence in the HOXA1 gene product (e.g., complementary to the 3' UTR of HOXA1). In a particular embodiment, the at least one miR gene product is miR-10a or an isolated variant or biologically-active fragment thereof.

In a related embodiment, the methods of treating cancer and/or a myeloproliferative disorder in a subject additionally comprise the step of first determining the amount of at least one miR gene product in a sample from the subject, and comparing that level of the miR gene product to the level of a corresponding miR gene product in a control. If expression of the miR gene product is deregulated (e.g., downregulated, upregulated) in the sample from the subject, the methods further comprise altering the amount of the at least one miR gene product expressed in the sample from the subject. In one embodiment, the amount of the miR gene product expressed in the sample from the subject is less than the amount of the miR gene product expressed in the control, and an effective amount of the miR gene product, or an isolated variant or biologically-active fragment thereof, is administered to the subject. In another embodiment, the amount of the miR gene product expressed in the sample from the subject is greater than the amount of the miR gene product expressed in the control, and an effective amount of at least one compound for inhibiting expression of the at least one miR gene is administered to the subject. Suitable miRs and compounds that inhibit expression of miR genes include, for example, those described herein.

The terms "treat", "treating" and "treatment", as used herein, refer to ameliorating symptoms associated with a disease or condition, for example, cancer and/or a myeloproliferative disorder, including preventing or delaying the onset of the disease symptoms, and/or lessening the severity or frequency of symptoms of the disease or condition. The terms "subject", "patient" and "individual" are defined herein to include animals, such as mammals, including, but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

As used herein, an "effective amount" of an isolated miR gene product is an amount sufficient to inhibit proliferation of cells (e.g., cancerous cells, cells exhibiting a myeloproliferative disorder) in a subject suffering from cancer and/or a myeloproliferative disorder. One skilled in the art can readily determine an effective amount of a miR gene product to be administered to a given subject, by taking into account factors, such as the size and weight of the subject; the extent of disease penetration; the age, health and sex of the subject; the route of administration; and whether the administration is regional or systemic.

For example, an effective amount of an isolated miR gene product can be based on the approximate weight of a tumor mass to be treated. The approximate weight of a tumor mass can be determined by calculating the approximate volume of the mass, wherein one cubic centimeter of volume is roughly equivalent to one gram. An effective amount of the isolated miR gene product based on the weight of a tumor mass can be in the range of about 10-500 micrograms/gram of tumor mass. In certain embodiments, the tumor mass can be at least about 10 micrograms/gram of tumor mass, at least about 60 micrograms/gram of tumor mass or at least about 100 micrograms/gram of tumor mass.

An effective amount of an isolated miR gene product can also be based on the approximate or estimated body weight of a subject to be treated. Preferably, such effective amounts are administered parenterally or enterally, as described herein. For example, an effective amount of the isolated miR gene product that is administered to a subject can range from about 5-3000 micrograms/kg of body weight, from about 700-1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

As used herein, an "isolated" miR gene product is one that is synthesized, or altered or removed from the natural state through human intervention. For example, a synthetic miR gene product, or a miR gene product partially or completely separated from the coexisting materials of its natural state, is considered to be "isolated." An isolated miR gene product can exist in a substantially-purified form, or can exist in a cell into which the miR gene product has been delivered. Thus, a miR gene product that is deliberately delivered to, or expressed in, a cell is considered an "isolated" miR gene product. A miR gene product produced inside a cell from a miR precursor molecule is also considered to be an "isolated" molecule. According to the invention, the isolated miR gene products described herein can be used for the manufacture of a medicament for treating cancer and/or a myeloproliferative disorder in a subject (e.g., a human).

Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR gene products in cells (e.g., cancerous cells, cells exhibiting a myeloproliferative disorder).

The miR gene products that are expressed from recombinant plasmids can be isolated from cultured cell expression systems by standard techniques. The miR gene products that are expressed from recombinant plasmids can also be delivered to, and expressed directly in, cells (e.g., cancerous cells, cells exhibiting a myeloproliferative disorder). The use of recombinant plasmids to deliver the miR gene products to cells (e.g., cancerous cells, cells exhibiting a myeloproliferative disorder) is discussed in more detail below.

The miR gene products can be expressed from a separate recombinant plasmid, or they can be expressed from the same recombinant plasmid. In one embodiment, the miR gene products are expressed as RNA precursor molecules from a single plasmid, and the precursor molecules are processed into the functional miR gene product by a suitable processing system, including, but not limited to, processing systems extant within a cancer cell. Other suitable processing systems include, e.g., the in vitro *Drosophila* cell lysate system (e.g., as described in U.S. Published Patent Application No. 2002/0086356 to Tuschl et al., the entire disclosure of which is incorporated herein by reference) and the *E. coli* RNAse III system (e.g., as described in U.S. Published Patent Application No. 2004/0014113 to Yang et al., the entire disclosure of which is incorporated herein by reference).

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), *Molecular Cell* 9:1327-1333; Tuschl (2002), *Nat. Biotechnol.* 20:446-448; Brummelkamp et al. (2002), *Science* 296:550-553; Miyagishi et al. (2002), *Nat. Biotechnol.* 20:497-500; Paddison et al. (2002), *Genes Dev.* 16:948-958; Lee et al. (2002), *Nat. Biotechnol.* 20:500-505; and Paul et al. (2002), *Nat. Biotechnol.* 20:505-508, the entire disclosures of which are incorporated herein by reference.

In one embodiment, a plasmid expressing the miR gene products comprises a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cells (e.g., cancerous cells, cells exhibiting a myeloproliferative disorder). The use of recombinant viral vectors to deliver the miR gene products to cells (e.g., cancerous cells, cells exhibiting a myeloproliferative disorder) is discussed in more detail below.

The recombinant viral vectors of the invention comprise sequences encoding the miR gene products and any suitable promoter for expressing the RNA sequences. Suitable promoters include, but are not limited to, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miR gene products in a cancer cell.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, J. E., et al. (2002), *J. Virol.* 76:791-801, the entire disclosure of which is incorporated herein by reference.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995), *Gene Therapy* 2:301-310; Eglitis (1988), *Biotechniques* 6:608-614; Miller (1990), *Hum. Gene Therapy* 1:5-14; and Anderson (1998), *Nature* 392:25-30, the entire disclosures of which are incorporated herein by reference.

Particularly suitable viral vectors are those derived from AV and AAV. A suitable AV vector for expressing the miR gene products, a method for constructing the recombinant AV vector, and a method for delivering the vector into target cells, are described in Xia et al. (2002), *Nat. Biotech.* 20:1006-1010, the entire disclosure of which is incorporated herein by reference. Suitable AAV vectors for expressing the miR gene products, methods for constructing the recombinant AAV vector, and methods for delivering the vectors into target cells are described in Samulski et al. (1987), *J. Virol.* 61:3096-3101; Fisher et al. (1996), *J. Virol.*, 70:520-532; Samulski et al. (1989), *J. Virol.* 63:3822-3826; U.S. Pat. No. 5,252,479; U.S. Pat. No. 5,139,941; International Patent Application No. WO 94/13788; and International Patent Application No. WO 93/24641, the entire disclosures of which are incorporated herein by reference. In one embodiment, the miR gene products are expressed from a single recombinant AAV vector comprising the CMV intermediate early promoter.

In a certain embodiment, a recombinant AAV viral vector of the invention comprises a nucleic acid sequence encoding a miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

In other embodiments of the treatment methods of the invention, an effective amount of at least one compound that inhibits miR expression can be administered to the subject. As used herein, "inhibiting miR expression" means that the production of the precursor and/or active, mature form of miR gene product after treatment is less than the amount produced prior to treatment. One skilled in the art can readily determine whether miR expression has been inhibited in cells (e.g., cancerous cells, cells exhibiting a myeloproliferative disorder), using, for example, the techniques for determining miR transcript level discussed herein. Inhibition can occur at the level of gene expression (i.e., by inhibiting transcription of a miR gene encoding the miR gene product) or at the level of processing (e.g., by inhibiting processing of a miR precursor into a mature, active miR).

As used herein, an "effective amount" of a compound that inhibits miR expression is an amount sufficient to inhibit proliferation of cells (e.g., cancerous cells, cells exhibiting a myeloproliferative disorder) in a subject suffering from cancer and/or a myeloproliferative disorder. One skilled in the art can readily determine an effective amount of a miR expression-inhibiting compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibiting compound can be based on the approximate weight of a tumor mass to be treated, as described herein. An effective amount of a compound that inhibits miR expression can also be based on the approximate or estimated body weight of a subject to be treated, as described herein.

One skilled in the art can also readily determine an appropriate dosage regimen for administering a compound that inhibits miR expression to a given subject, as described herein. Suitable compounds for inhibiting miR gene expression include double-stranded RNA (such as short- or small-interfering RNA or "siRNA"), antisense nucleic acids, and enzymatic RNA molecules, such as ribozymes. Each of these compounds can be targeted to a given miR gene product and interfere with the expression (e.g., by inhibiting translation, by inducing cleavage and/or degradation) of the target miR gene product.

For example, expression of a given miR gene can be inhibited by inducing RNA interference of the miR gene with an isolated double-stranded RNA ("dsRNA") molecule which has at least 90%, for example, at least 95%, at least 98%, at least 99%, or 100%, sequence homology with at least a portion of the miR gene product. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence that is substantially identical to a nucleic acid sequence contained within the target miR gene product.

As used herein, a nucleic acid sequence in an siRNA that is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miR gene products. Exemplary methods for producing and testing dsRNA or siRNA molecules are described in U.S. Published Patent Application No. 2002/0173478 to Gewirtz and in U.S. Published Patent Application No. 2004/0018176 to Reich et al., the entire disclosures of both of which are incorporated herein by reference.

Expression of a given miR gene can also be inhibited by an antisense nucleic acid. As used herein, an "antisense nucleic acid" refers to a nucleic acid molecule that binds to target RNA by means of RNA-RNA, RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, peptide nucleic acids (PNA)) that generally comprise a nucleic acid sequence complementary to a contiguous nucleic acid sequence in a miR gene product. The antisense nucleic acid can comprise a nucleic acid sequence that is 50-100% complementary, 75-100% complementary, or 95-100% complementary to a contiguous nucleic acid sequence in a miR gene product. Nucleic acid sequences of particular human miR gene products are provided in Table 1a and Table 1b. Without wishing to be bound by any theory, it is believed that the antisense nucleic acids activate RNase H or another cellular nuclease that digests the miR gene product/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups.

Antisense nucleic acids can be produced chemically or biologically, or can be expressed from a recombinant plasmid or viral vector, as described above for the isolated miR gene products. Exemplary methods for producing and testing are within the skill in the art; see, e.g., Stein and Cheng (1993), *Science* 261:1004 and U.S. Pat. No. 5,849,902 to Woolf et al., the entire disclosures of which are incorporated herein by reference.

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of a miR gene product, and which is able to specifically cleave the miR gene product. The enzymatic nucleic acid substrate binding region can be, for example, 50-100% complementary, 75-100% complementary, or 95-100% complementary to a contiguous nucleic acid sequence in a miR gene product. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated miR gene products. Exemplary methods for producing and testing dsRNA or siRNA molecules are described in Werner and Uhlenbeck (1995), *Nucleic Acids Res.* 23:2092-96; Hammann et al. (1999), *Antisense and Nucleic Acid Drug Dev.* 9:25-31; and U.S. Pat. No. 4,987,071 to Cech et al, the entire disclosures of which are incorporated herein by reference.

Administration of at least one miR gene product, or at least one compound for inhibiting miR expression, will inhibit the proliferation of cells (e.g., cancerous cells, cells exhibiting a myeloproliferative disorder) in a subject who has a cancer and/or a myeloproliferative disorder. As used herein, to "inhibit the proliferation of cancerous cells or cells exhibiting a myeloproliferative disorder" means to kill the cells, or permanently or temporarily arrest or slow the growth of the cells. Inhibition of cell proliferation can be inferred if the number of such cells in the subject remains constant or decreases after administration of the miR gene products or miR gene expression-inhibiting compounds. An inhibition of proliferation of cancerous cells or cells exhibiting a myeloproliferative disorder can also be inferred if the absolute number of such cells increases, but the rate of tumor growth decreases.

The number of cancer cells in the body of a subject can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The size of a tumor mass can be ascertained by direct visual observation, or by diagnostic imaging methods, such as X-ray, magnetic resonance imaging, ultrasound, and scintigraphy. Diagnostic imaging methods used to ascertain size of the tumor mass can be employed with or without contrast agents, as is known in the art. The size of a tumor mass can also be ascertained by physical means, such as palpation of the tissue mass or measurement of the tissue mass with a measuring instrument, such as a caliper.

The miR gene products or miR gene expression-inhibiting compounds can be administered to a subject by any means suitable for delivering these compounds to cells (e.g., cancer cells, cells exhibiting a myeloproliferative disorder) of the subject. For example, the miR gene products or miR expression-inhibiting compounds can be administered by methods suitable to transfect cells of the subject with these compounds, or with nucleic acids comprising sequences encoding these compounds. In one embodiment, the cells are transfected with a plasmid or viral vector comprising sequences encoding at least one miR gene product or miR gene expression-inhibiting compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy) propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

A miR gene product or miR gene expression-inhibiting compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the tumor.

In the present methods, a miR gene product or miR gene product expression-inhibiting compound can be administered to the subject either as naked RNA, in combination with a delivery reagent, or as a nucleic acid (e.g., a recombinant plasmid or viral vector) comprising sequences that express the miR gene product or miR gene expression-inhibiting compound. Suitable delivery reagents include, e.g., the Mirus Transit TKO lipophilic reagent; LIPOFECTIN; lipofectamine; cellfectin; polycations (e.g., polylysine) and liposomes.

Recombinant plasmids and viral vectors comprising sequences that express the miR gene products or miR gene expression-inhibiting compounds, and techniques for delivering such plasmids and vectors to cancer cells, are discussed herein and/or are well known in the art.

In a particular embodiment, liposomes are used to deliver a miR gene product or miR gene expression-inhibiting compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to cancer cells. Ligands that bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both an opsonization-inhibition moiety and a ligand.

Opsonization-inhibiting moieties for use in preparing the liposomes of the invention are typically large hydrophilic polymers that are bound to the liposome membrane. As used herein, an opsonization-inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization-inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) or derivatives thereof; e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization-inhibiting polymer can be a block copolymer of PEG and either a polyamino acid, polysaccharide, polyamidoamine, polyethyleneamine, or polynucleotide. The opsonization-inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or a derivative thereof. Liposomes modified with PEG or PEG-derivatives are sometimes called "PEGylated liposomes."

The opsonization-inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)BH$_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example, solid tumors, will efficiently accumulate these liposomes; see Gabizon, et al. (1988), Proc. Natl. Acad. Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products or miR gene expression-inhibition compounds (or nucleic acids comprising sequences encoding them) to tumor cells.

The miR gene products or miR gene expression-inhibition compounds can be formulated as pharmaceutical compositions, sometimes called "medicaments," prior to administering them to a subject, according to techniques known in the art. Accordingly, the invention encompasses pharmaceutical compositions for treating cancer and/or a myeloproliferative disorder.

In one embodiment, the pharmaceutical composition of the invention comprises at least one miR expression-inhibition compound and a pharmaceutically-acceptable carrier. In a particular embodiment, the at least one miR expression-inhibition compound is specific for a miR gene product whose expression is greater in cancer cells than control cells (i.e., it is upregulated). In another embodiment, the miR expression-inhibition compound is specific for one or more miR gene products selected from the group consisting of miR-101, miR-126, miR-99a, miR-99-prec, miR-106, miR-339, miR-99b, miR-149, miR-33, miR-135 and miR-20. In another embodiment, the miR expression-inhibition compound is specific for one or more miR gene products selected from the group consisting of miR-101, miR-126, miR-106, miR-20, and miR-135. In yet another embodiment, the miR expression-inhibition compound is specific for one or more miR gene products selected from the group consisting of miR-106, miR-20 and miR-135.

In other embodiments, the pharmaceutical compositions comprise an effective amount of at least one miR gene product, or an isolated variant or biologically-active fragment thereof, and a pharmaceutically-acceptable carrier. In one embodiment, the invention is a pharmaceutical composition for treating a cancer and/or a myeloproliferative disorder, wherein the cancer and/or myeloproliferative disorder is associated with overexpression of a MAFB gene product. In this embodiment, the pharmaceutical composition comprises at least one miR gene product that binds to, and decreases expression of, the MAFB gene product. In a particular embodiment, the at least one miR gene product comprises a nucleotide sequence that is complementary to a nucleotide sequence in the MAFB gene product. In another embodiment, the at least one miR gene product is miR-130a or an isolated variant or biologically-active fragment thereof.

In one embodiment, the invention is a pharmaceutical composition for treating a cancer and/or a myeloproliferative disorder, wherein the cancer and/or myeloproliferative disorder is associated with overexpression of a HOXA1 gene product. In this embodiment, the pharmaceutical composition comprises at least one miR gene product that binds to, and decreases expression of, the HOXA1 gene product. In a particular embodiment, the at least one miR gene product comprises a nucleotide sequence that is complementary to a nucleotide sequence in the HOXA1 gene product. In another embodiment, the at least one miR gene product is miR-10a or an isolated variant or biologically-active fragment thereof.

Pharmaceutical compositions of the present invention are characterized as being at least sterile and pyrogen-free. As used herein, "pharmaceutical compositions" include formulations for human and veterinary use. Methods for preparing pharmaceutical compositions of the invention are within the skill in the art, for example, as described in Remington's Pharmaceutical Science, 17th ed., Mack Publishing Company, Easton, Pa. (1985), the entire disclosure of which is incorporated herein by reference.

The present pharmaceutical compositions comprise at least one miR gene product or miR gene expression-inhibition compound (or at least one nucleic acid comprising a sequence encoding the miR gene product or miR gene expression-inhibition compound) (e.g., 0.1 to 90% by weight), or a physiologically-acceptable salt thereof, mixed with a pharmaceutically-acceptable carrier. In certain embodiments, the pharmaceutical composition of the invention additionally comprises one or more anti-cancer agents (e.g., chemotherapeutic agents). The pharmaceutical formulations of the invention can also comprise at least one miR gene product or miR gene expression-inhibition compound (or at least one nucleic acid comprising a sequence encoding the miR gene product or miR gene expression-inhibition compound), which are encapsulated by liposomes and a pharmaceutically-acceptable carrier. In one embodiment, the pharmaceutical composition comprises a miR gene or gene product that is not miR-15, miR-16, miR-143 and/or miR-145.

Especially suitable pharmaceutically-acceptable carriers are water, buffered water, normal saline, 0.4% saline, 0.3% glycine, hyaluronic acid and the like.

In a particular embodiment, the pharmaceutical compositions of the invention comprise at least one miR gene product or miR gene expression-inhibition compound (or at least one nucleic acid comprising a sequence encoding the miR gene product or miR gene expression-inhibition compound) that is resistant to degradation by nucleases. One skilled in the art can readily synthesize nucleic acids that are nuclease resistant, for example by incorporating one or more ribonucleotides that is modified at the 2'-position into the miR gene product. Suitable 2'-modified ribonucleotides include those modified at the 2'-position with fluoro, amino, alkyl, alkoxy and O-allyl.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR gene product or miR gene expression-inhibition compound (or at least one nucleic acid comprising sequences encoding them). A pharmaceutical composition for aerosol (inhalational) administration can comprise 0.01-20% by weight, preferably 1%-10% by weight, of the at least one miR gene product or miR gene expression-inhibition compound (or at least one nucleic acid comprising a sequence encoding the miR gene product or miR gene expression-inhibition compound) encapsulated in a liposome as described above, and a propellant. A carrier can also be included as desired; e.g., lecithin for intranasal delivery.

The pharmaceutical compositions of the invention can further comprise one or more anti-cancer agents. In a particular embodiment, the compositions comprise at least one miR gene product or miR gene expression-inhibition compound (or at least one nucleic acid comprising a sequence encoding the miR gene product or miR gene expression-inhibition compound) and at least one chemotherapeutic agent. Chemotherapeutic agents that are suitable for the methods of the invention include, but are not limited to, DNA-alkylating agents, anti-tumor antibiotic agents, anti-metabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial and exotoxic agents. Examples of suitable agents for the compositions of the present invention include, but are not limited to, cytidine arabinoside, methotrexate, vincristine, etoposide (VP-16), doxorubicin (adriamycin), cisplatin (CDDP), dexamethasone, arglabin, cyclophosphamide, sarcolysin, methylnitrosourea, fluorouracil, 5-fluorouracil (5FU), vinblastine, camptothecin, actinomycin-D, mitomycin C, hydrogen peroxide, oxaliplatin, irinotecan, topotecan, leucovorin, carmustine, streptozocin, CPT-11, taxol, tamoxifen, dacarbazine, rituximab, daunorubicin, 1-β-D-arabinofuranosylcytosine, imatinib, fludarabine, docetaxel and FOLFOX4.

The invention also encompasses methods of identifying an anti-cancer agent, comprising providing a test agent to a cell and measuring the level of at least one miR gene product in the cell. In one embodiment, the method comprises providing a test agent to a cell and measuring the level of at least one miR gene product associated with increased expression levels in cancer cells (e.g., in AMKL cells). A decrease in the level of the miR gene product that is associated with increased expression levels in cancer, relative to a suitable control (e.g., the level of the miR gene product in control cells), is indicative of the test agent being an anti-cancer agent. In a particular embodiment, the at least one miR gene product associated with increased expression levels in cancer cells is selected from the group consisting of miR-101, miR-126, miR-99a, miR-99-prec, miR-106, miR-339, miR-99b, miR-149, miR-33, miR-135 and miR-20. In another embodiment, the at least one miR gene product associated with increased expression levels in cancer cells is selected from the group consisting of miR-101, miR-126, miR-106, miR-20 and miR-135. In yet another embodiment, the at least one miR gene product associated with increased expression levels in cancer cells is selected from the group consisting of miR-106, miR-20 and miR-135. In one embodiment, the miR gene product is not one or more of let7a-2, let-7c, let-7g, let-7i, miR-7-2, miR-7-3, miR-9, miR-9-1, miR-10a, miR-15a, miR-15b, miR-16-1, miR-16-2, miR-17-5p, miR-20a, miR-21, miR-24-1, miR-24-2, miR-25, miR-29b-2, miR-30, miR-30a-5p, miR-30c, miR-30d, miR-31, miR-32, miR-34, miR-34a, miR-34a prec, miR-34a-1, miR-34a-2, miR-92-2, miR-96, miR-99a, miR-99b prec, miR-100, miR-103, miR-106a, miR-107, miR-123, miR-124a-1, miR-125b-1, miR-125b-2, miR-126*, miR-127, miR-128b, miR-129, miR-129-1/2 prec, miR-132, miR-135-1, miR-136, miR-137, miR-141, miR-142-as, miR-143, miR-146, miR-148, miR-149, miR-153, miR-155, miR 159-1, miR-181, miR-181b-1, miR-182, miR-186, miR-191, miR-192, miR-195, miR-196-1, miR-196-1 prec, miR-196-2, miR-199a-1, miR-199a-2, miR-199b, miR-200b, miR-202, miR-203, miR-204, miR-205, miR-210, miR-211, miR-212, miR-214, miR-215, miR-217, miR-221 and/or miR-223.

In one embodiment, the method comprises providing a test agent to a cell and measuring the level of at least one miR gene product associated with decreased expression levels in cancerous cells. An increase in the level of the miR gene product in the cell, relative to a suitable control (e.g., the level of the miR gene product in a control cell), is indicative of the test agent being an anti-cancer agent.

Suitable agents include, but are not limited to drugs (e.g., small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one miR gene product (e.g., Northern blotting, in situ hybridization, RT-PCR, expression profiling) are also well known in the art. Several of these methods are also described herein.

The invention will now be illustrated by the following non-limiting examples.

Exemplification

Unless otherwise noted, the following materials and methods were used in the Examples.

Material and methods

Cell Lines and Human CD34+ Cells.

The human chronic myeloid leukemia (CML) blast crisis cell lines K-562 and MEG-01 were obtained from American Type Tissue Culture (ATCC, Manassas, Va.) and maintained in RPMI 1640 (GIBCO, Carlsbad, Calif.) containing 10% FBS with penicillin-gentamycin at 37° C. with 5% CO2. The human megakaryoblastic leukemia cells UT-7, and CMK, and the chronic myeloid leukemia (CML) in blast crisis LAMA were obtained from DSMZ (Braunsweig, Germany). All cells were maintained in RPMI medium 1640 with 20% FBS and antibiotics, except UT-7 which is factor-dependent and was cultured in MEM- with 20% FBS and 5 ng/ml GM-CSF. Fresh and frozen human bone marrow CD34+ cells were obtained from Stemcell Technologies (Vancouver, B.C., Canada). FACS analysis for CD34 antigen revealed a purity>98%.

Human Progenitor CD34+ Cell Cultures.

Human bone marrow CD34+ cells were grown in STEM-media (Stemcell Technologies), which includes Isocove modified Dulbecco's medium supplemented with human transferrin, insulin, bovine serine albumin, human low density lipoprotein and glutamine, in the presence of 100 ng/ml human recombinant thrombopoietin (TPO) for the first 4 days, followed by a combination of 100 ng/ml TPO, IL3, and SCF (cytokine mixture CC-200, Stemcell Technologies). The initial cell density was 100,000 cells/ml; three times a week, the cell density was adjusted to 100,000 to 200,000 cells/ml. To increase the purity of the cells for microarray analysis, cell sorting was performed at day 10 of culture. Cells were incubated on ice for 45 minutes with anti-human CD34+, anti-human CD41+, anti-human CD61+, and their respective isotypes. After washing twice with PBS 3% FBS, cells were sorted using a FACS Aria sorting machine in bulk in two separate populations; CD34−CD61+ and CD34+ CD61+ cells for culture and RNA extraction. The purity of the sorted populations was greater than 95%.

Megakaryocytes Characterization.

Cytospin preparations of CD34+ progenitors in culture were performed and stained with May-Grunwald Giemsa at different time points during the megakaryocytic differentiation induction. For FACS analysis, the primary antibodies that were used were as follows: CD41A, CD61A, CD42B, and CD34 with their respective isotypes (BD Pharmingen, San Diego, Calif.). Cytometric studies were performed as previously described (Tajima, S., et al. (1996) *J. Exp. Med.* 184, 1357-1364) using a FACScalibur (BD Biosciences) and the CELLQUEST software (BD Biosciences).

RNA Extraction, Northern Blotting and miRNA Microarray Experiments.

Procedures were performed as described in detail elsewhere (Liu, C. G., et al. (2002) *Proc. Natl. Acad. Sci. USA* 101, 9740-9744). Raw data were normalized and analyzed in GENESPRING 7.2 software (zcomSilicon Genetics, Redwood City, Calif.). Expression data were median-centered by using both GENESPRING normalization option and global median normalization of the BIOCONDUCTOR package (www.bioconductor.org) with similar results. Statistical comparisons were done by using the GENESPRING ANOVA tool, predictive analysis of microarray (PAM) and the significance analysis of microarray (SAM) software (www-stat.stanford.edu/~tibs/SAM/index.html).

Reverse Transcriptase PCR (RT-PCR) and Real Time PCR.

Total RNA isolated with Trizol reagent (Invitrogen, Carlsbad, Calif.) was processed after DNAase treatment (Ambion, Austin, Tex.) directly to cDNA by reverse transcription using Superscript II (Invitrogen). Comparative real-time PCR was performed in triplicate. Primers and probes were obtained from Applied Biosystems (Foster City, Calif.) for the following genes: HOXA1, HOXA3, HOXB4, HOXB5, and HOXD10. Gene expression levels were quantified by using the ABI Prism 7900 Sequence detection system (Applied Biosystems). Normalization was performed by using the 18S RNA primer kit. Relative expression was calculated by using the computed tomography (CT) method. RT-PCR also was performed by using the following oligonucleotide primers:

```
                              (SEQ ID NO: 499)
MAFB FW;   5'-AACTTTGTCTTGGGGGACAC-3';

(SEQ ID NO: 500)
MAFB RW;   5'-GAGGGGAGGATCTGTTTTCC-3';

(SEQ ID NO: 501)
HOXA1 FW;  5'-CCAGGAGCTCAGGAAGAAGA GAT-3';
and (SEQ ID NO: 502)
HOXA1 RW;  5'-CCCTCTGAGGCATCTGATTGGGTTT-3'.
```

Real-Time Quantification of miRNAs by Stem-Loop RT-PCR.

Real time-PCR for pri-miRNAs 10a, miR15a, miR16-1, miR-130a, miR-20, miR-106, miR-17-5, miR-181b, miR-99a, and miR-126 were performed as described (Chen, C., et al. (2005) *Nucl. Acids Res.* 33, e179. 18S was used for normalization. All reagents and primers were obtained from Applied Biosystems.

Bioinformatics.

miRNA target prediction of the differentially expressed miRNAs was performed by using TARGETSCAN (www.genes.mit.edu/targetscan), MIRANDA (www.mskc.miranda.org), and PICTAR (www.pictar.bio.nyu.edu) software.

Cell Transfection with miRNA Precursors.

miRNA precursors miR-10a and miR-130a were purchased from Ambion. Five million K562 cells were nucleoporated by using Amaxa (Gaithesburg, Md.) with 5 µg of precursor oligonucleotides in a total volume of 10 ml. The expression of the oligonucleotides was assessed by Northern blots and RT-PCR as described.

Luciferase Reporter Experiments.

The 3' UTR segments containing the target sites for miR-10a and miR-130a from HOXA1 and MAFB genes, respectively, were amplified by PCR from genomic DNA and inserted into the pGL3 control vector (Promega, Madison, Wis.), by using the XbaI site immediately downstream from the stop codon of luciferase. The following oligonucleotide primer sets were used to generate specific fragments:

```
MAFB FW     5'-GCATCTAGAGCACCCCAGAGGAGTGT-3';      (SEQ ID NO: 503)

MAFB RW     5'-GCATCTAGACAAGCACCATGCGGTTC-3';      (SEQ ID NO: 504)

HOXA1 FW    5'-TACTCTAGACCAGGAGCTCAGGAAGA-3';      (SEQ ID NO: 505)
and

HOXA1 RW    5'-MCATTCTAGATGAGGCATCTGATTGGG-3'.     (SEQ ID NO: 506)
```

We also generated two inserts with deletions of 5 by and 9 bp, respectively, from the site of perfect complementarity by using the QuikChange XL-site directed Mutagenesis Kit (Stratagene, La Jolla, Calif.). Wild type (WT) and mutant insert were confirmed by sequencing.

Human chronic myeloid leukemia (CML) in megakaryoblastic crisis cell line (MEG-01) was cotransfected in six-well plates by using Lipofectamine 2000 (Invitrogen) according to the manufacturer's protocol with 0.4 µg of the firefly luciferase report vector and 0.08 µg of the control vector containing Renilla luciferase, pRL-TK (Promega). For each well, 10 nM of the premiR-130a and premiR-10a precursors (Ambion) were used. Firefly and Renilla luciferase activities were measured consecutively by using the dual luciferase assays (Promega) 24 hours after transfection.

Western Blots.

Total and nuclear protein extracts from K562 cells transfected with miR-10a and miR-130a, as well as CD34+ cells at different stages of megakaryocytic differentiation were extracted by using RIPA buffer or Nuclear extraction Kit (Pierce, Rockford, Ill.). Protein expression was analyzed by Western blotting with the following primary antibodies: MAFB (Santa Cruz Biotechnology, Santa Cruz, Calif.), HOXA1 (R&D Systems, Minneapolis, Minn.), 13-Actin and Nucleolin (Santa Cruz Biotechnology). Appropriate secondary antibodies were used (Santa Cruz Biotechnology).

EXAMPLE 1 miRNA Expression During in Vitro Megakaryocytic Differentiation of CD34+ Progenitors Using a combination of a specific megakaryocytic growth factor (thrombopoietin) and nonspecific cytokines (SCF and IL-3), we were able to generate in vitro pure, abundant megakaryocyte progeny from CD34+ bone marrow progenitors suitable for microarray studies (FIG. 4). Total RNA was obtained for miRNA chip analysis from three different CD34 progenitors at baseline and at days 10, 12, 14 and 16 of culture with cytokines. We initially compared the expression of miRNA between the CD34+ progenitors and the pooled CD34+ differentiated megakaryocytes at all points during the differentiation process. 17 miRNAs (Table 1) that are sharply down regulated during megakaryocytic differentiation were identified. There were no statistically significant miRNAs upregulated during megakaryocytic differentiation. Using predictive analysis of microarray (PAM), we identified 8 microRNAs that predicted megakaryocytic differentiation with no misclassification error: miR-10a, miR-10b, miR-30c, miR-106, miR-126, miR-130a, miR-132, and miR-143. All of these miRNAs, except miR-143, are included in the 17 miRNAs identified by significance analysis of microarray (SAM). Northern blots and real-time PCR for several miRNAs confirmed the results obtained by miRNA chip analysis (FIG. 1).

Because we found mainly downregulation of miRNAs during megakaryocytopoiesis, we hypothesized that these miRNAs may unblock target genes involved in differentiation. In line with this hypothesis, miRNAs that are sharply downregulated in our system are predicted to target genes with important roles in megakaryocytic differentiation. Among the transcription factors with well-known function in megakaryocytopoiesis, RUNX-1 (Elagib, K. E., et al. (2003) Blood, 101:4333-4341), Fli-1 (Athanasoiu, M., et al. (1996) Cell Growth Differ. 7, 1525-1534), FLT1 (Casella, I., et al. (2003) Blood 101, 1316-1323), ETV6 (Hock, H., et al. (2004) Genes Dev. 18:2336-2341), TAL1

TABLE 2 miRNAs downregulated during in vitro CD34+ megakaryocytic differentiation.
All differentially expressed miRNAs have q value < 0.01 (false-positive rate).

| miRNA | Chromosomal Location | T-test (†) | Fold Change | Putative targets |
|---|---|---|---|---|
| hsa-mir-010a* | 17q21 | −9.10 | 50.00 | HOXA1, HOXA3, HOXD10, CRK, FLT1 |
| hsa-mir-126* | 9q34 | −2.73 | 8.33 | CRK, EVI2, HOXA9, MAFB, CMAF |
| hsa-mir-106* | xq26.2 | −2.63 | 2.86 | TAL1, FLT1, SKI, RUNX1, FOG2, FLI, PDGFRA, CRK |
| hsa-mir-010b* | 2q31 | −2.17 | 11.11 | HOXA1, HOXA3, HOXD10, ETS-1, CRK, FLT1 |
| hsa-mir-130a* | 11q12 | −2.08 | 4.76 | MAFB, MYB, FOG2, CBFB, PDGFRA, SDFR1, CXCL12 |
| hsa-mir-130a-prec* | 11q12 | −2.07 | 7.69 | NA± |
| hsa-mir-124a | 8q23 | −1.81 | 2.78 | TAL1, SKI, FLT1, FOG2, ETS-1, CBFB, RAF1, MYB |
| hsa-mir-032-prec | 9q31 | −1.76 | 3.57 | NA± |
| hsa-mir-101 | 1p31.3 | −1.75 | 3.33 | TAL1, CXCL12, MEIS1, MEIS2, ETS-1 RUNX1, MYB |
| hsa-mir-30c | 6q13 | −1.71 | 2.56 | CBFB, MAFG, HOXA1, SBF1, NCOR2, ERG |
| hsa-mir-213* | 1q31.3 | −1.69 | 2.38 | MAX-SATB2 |
| hsa-mir-132-prec | 17p13 | −1.67 | 4.17 | NA± |

TABLE 2-continued miRNAs downregulated during in vitro CD34+ megakaryocytic differentiation.
All differentially expressed miRNAs have q value < 0.01 (false-positive rate).

| miRNA | Chromosomal Location | T-test (†) | Fold Change | Putative targets |
|---|---|---|---|---|
| hsa-mir-150* | 19q13.3 | −1.63 | 5.26 | MYB, SDFR1 |
| hsa-mir-020 | 13q31 | −1.62 | 2.17 | TAL1, SKI, RUNX-1, FLT1, CRK, FOG2, RARB |
| hsa-mir-339 | 7p22 | −1.60 | 3.03 | SKI, ETV6, GATA2, FLT1, RAP1B, JUNB, MEIS2 |
| hsa-let-7a | 9q22 | −1.58 | 2.94 | HOXA1, HOXA9, MEIS2, ITGB3, PLDN |
| hsa-let-7d | 9q22 | −1.56 | 2.17 | HOXA1, HOXD1, ITGB3, RUNX1, PDGFRA |
| hsa-mir-181c | 19p13 | −1.55 | 2.50 | RUNX-1, KIT, HOXA1, MEIS2, ETS-1 ETV6, PDGFRA |
| hsa-mir-181b | 1q31.3 | −1.53 | 2.13 | RUNX-1, KIT, ITGA3, HOXA1, MEIS2, ETS-1, SDFR1, |
| hsa-mir-017 | 13q31 | −1.38 | 1.82 | TAL1, SKI, FLT1, RUNX1, CRK, FOG1, ETS-1, MEIS1 |

(†) t test p < 0.05.
*These miRNAs were identified by PAM as predictors of a megakaryocytic class with the lowest misclassification error. All, except miR-143 are downregulated during megakaryocytic differentiation.
NA±: miRNA precursor sequence that does not contain the mature miRNA, therefore no putative target is shown.

(Begley, C. G., and Green, A. R. (1999) Blood, 93:2760-2770), ETS1 (Jackers, P., et al. (2004) J. Biol. Chem. 279: 52183-52190) and CRK (Lannutti, B. J., et al. (2003) Exp. Hematol. 12:1268-1274) are putative targets for several miRNAs downregulated in differentiated megakaryocytes. Moreover, each of these transcription factors has more than one miRNA predicted to be its regulator. For example, RUNX1 (AML1) is predicted to be the target of miR-106, miR-181b, miR-101, let7d and the miR-17-92 cluster. The multiplicity of miRNAs predicted to target AML1 suggests a combinatorial model of regulation.

Figure 1C:
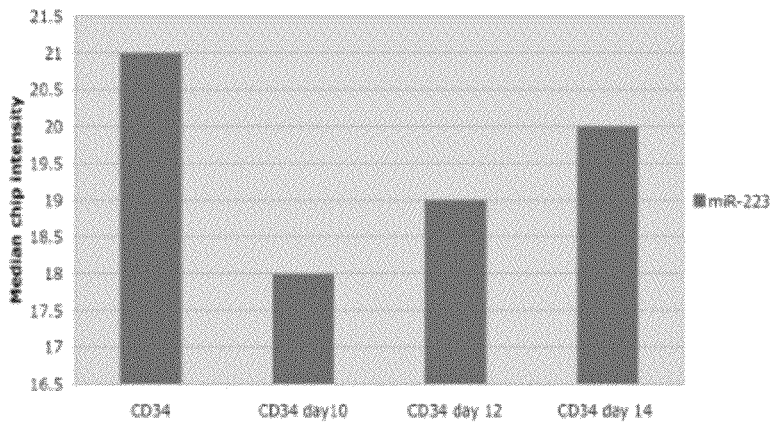
Figure 1D:
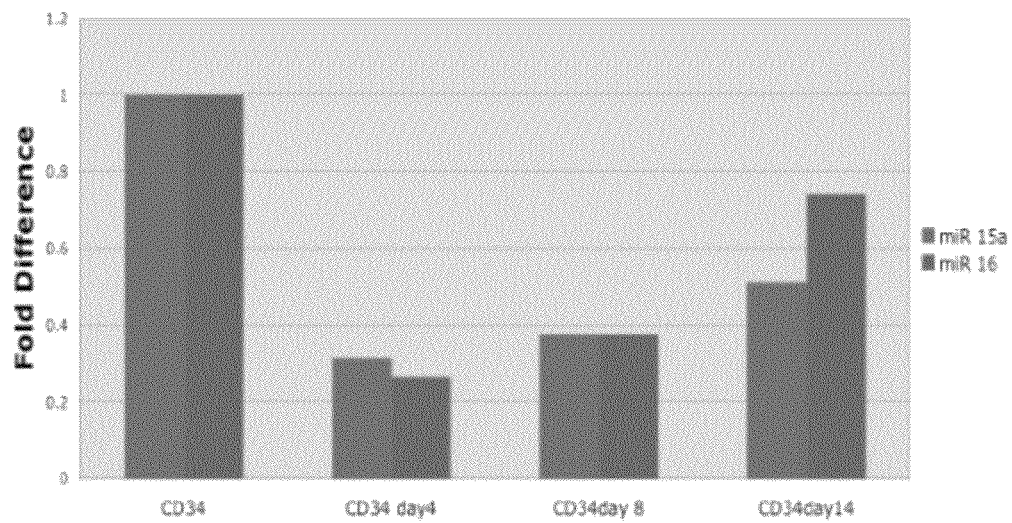
Figure 5:
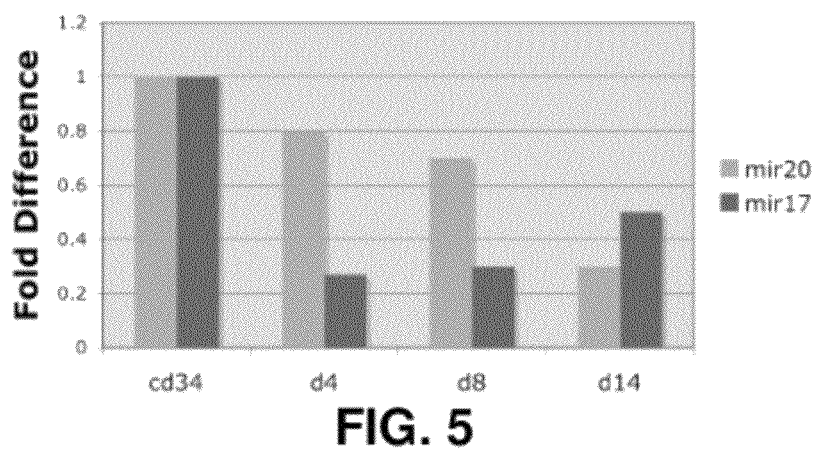
FIG. 5 is a graph depicting RT-PCR expression results for miR-20 and miR-17 in differentiated megakaryocytes. The results are presented as fold difference with respect to CD34$^+$ cells at baseline after normalization with 18S and delta Ct calculations.
Figure 6A:
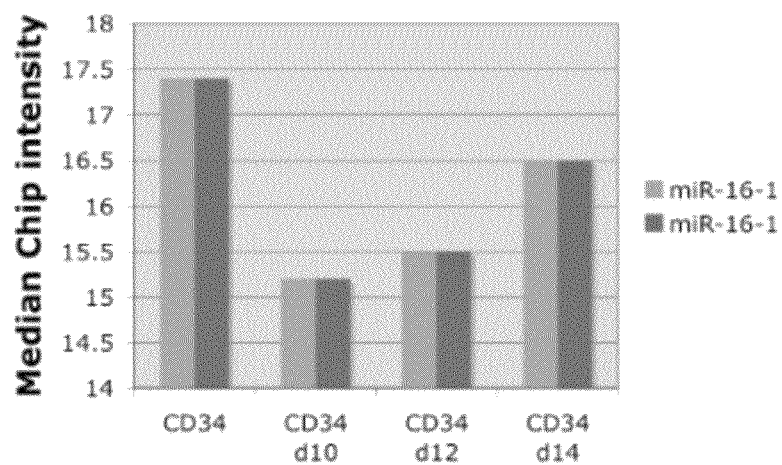
FIG. 6A is a graph depicting temporal expression of miR-16-1 during megakaryocytic differentiation. The absolute expression value of miR-16-1 was determined by a per-chip median normalization.
Figure 6B:
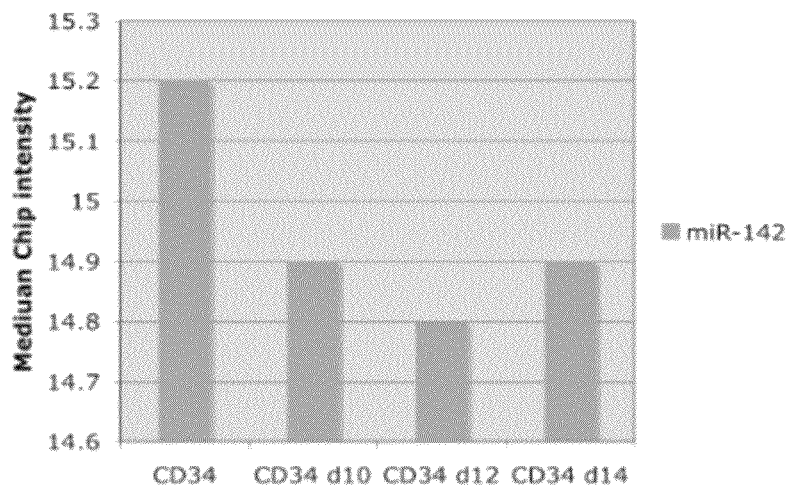
FIG. 6B is a graph depicting temporal expression of miR-142 during megakaryocytic differentiation. The absolute expression value of miR-142 was determined by a per-chip median normalization.
Figure 6C:
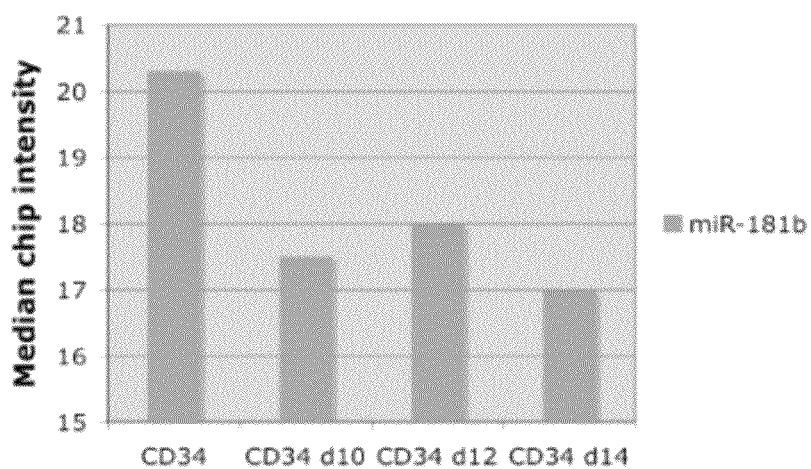
FIG. 6C is a graph depicting temporal expression of miR-181b during megakaryocytic differentiation. The absolute expression value of miR-181b was determined by a per-chip median normalization.

We then looked at the temporal expression of miRNAs during the megakaryocytic differentiation process from CD34+ progenitors. We focused on miRNAs that have been described in hematopoietic tissues, such as miR-223, miR-181, miR-155, miR-142, miR-15a, miR-16, miR-106 and the cluster of miR-17-92 (FIG. 5). We found sequential changes in the expression of miR-223. Initially, miR-223 is downregulated during megakaryocytic differentiation, but after 14 days in culture, its expression returns to levels comparable with that of CD34 progenitors (FIG. 1C). The miR-15a and miR-16-1 cluster also follows the same pattern of expression as miR-223 (FIG. 1D), whereas miR-181b, miR-155, miR-106a, miR-17, and miR-20 were downregulated during differentiation (FIG. 6). The temporal variation of the expression of miR-223 and miR-15a/mir-16-1 suggests a stage-specific function.

EXAMPLE 2

MAFB Transcription Factor is a Target of miR-130a

Figure 2A:
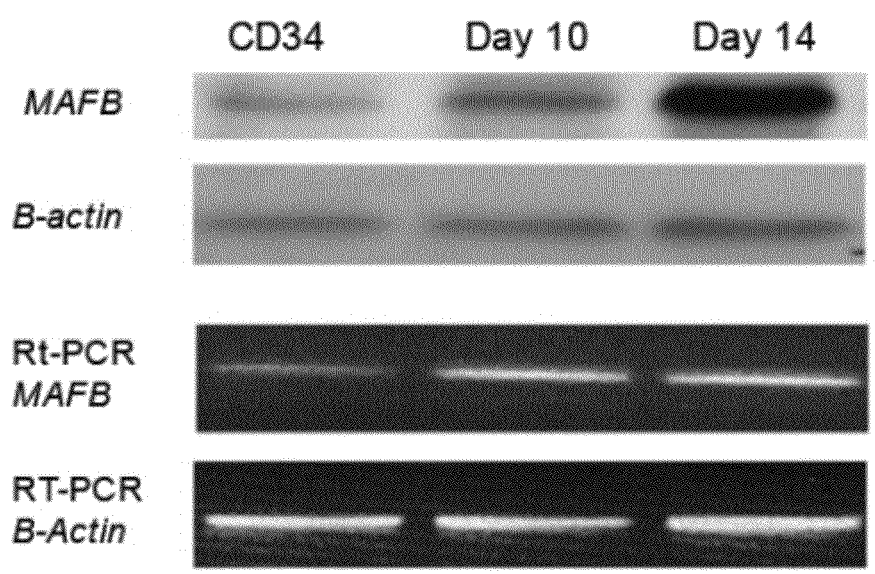

By using three target prediction algorithms (TARGETSCAN (www.genes.mit.edu/targetscan), MIRANDA (www.microrna.org/miranda_new.html), and PICTAR (www.pictar.bio.nyu.edu)), we identified that miR-130a is predicted to target MAFB, a transcription factor that is upregulated during megakaryocytic differentiation and induces the GPIIb gene, in synergy with GATA1, SP1 and ETS-1 (Sevinsky, J. R., et al. (2004) Mol. Cell. Biol. 24, 4534-4545). To investigate this putative interaction, first, we examined MAFB protein and mRNA levels in CD34+ progenitors at baseline and after cytokine stimulation (FIG. 2A). We found that the MAFB protein is upregulated during in vitro megakaryocytic differentiation. Although the mRNA levels for MAFB by PCR increase with differentiation, this increase does not correlate well with the intensity of its protein expression. The inverse pattern of expression of MAFB and miR-130a suggested in vivo interaction that was further investigated.

Figure 2B:
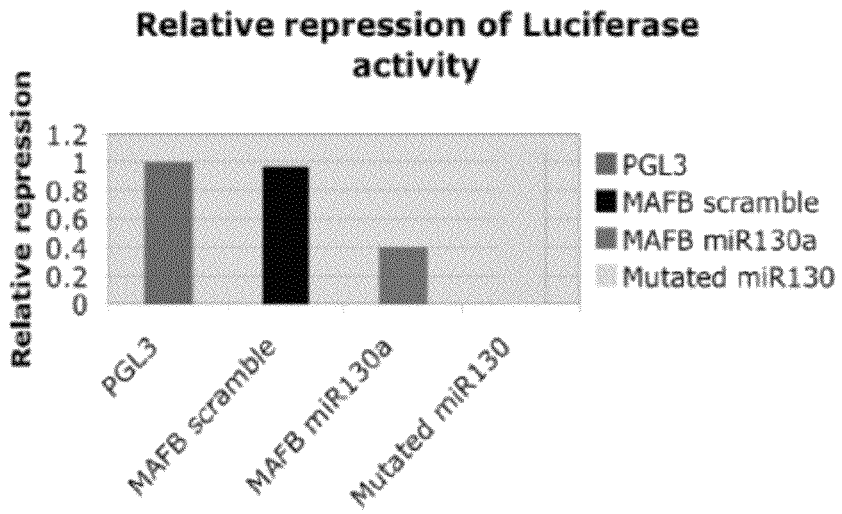

To demonstrate a direct interaction between the 3' UTRs of MAFB with miR-130a, we inserted the 3' UTR regions predicted to interact with this miRNA into a luciferase vector. This experiment revealed a repression of about ~60% of luciferase activity compared with control vector (FIG. 2B). As an additional control experiment, we used a mutated target mRNA sequence for MAFB lacking five of the complementary bases. As expected, the mutations completely abolished the interaction between miR-130a and its target 3'UTRs (FIG. 2B).

Figure 2C:
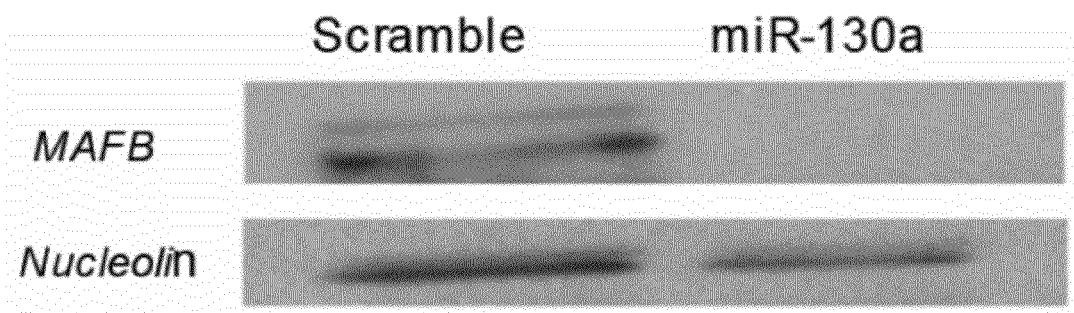
Figure 7:
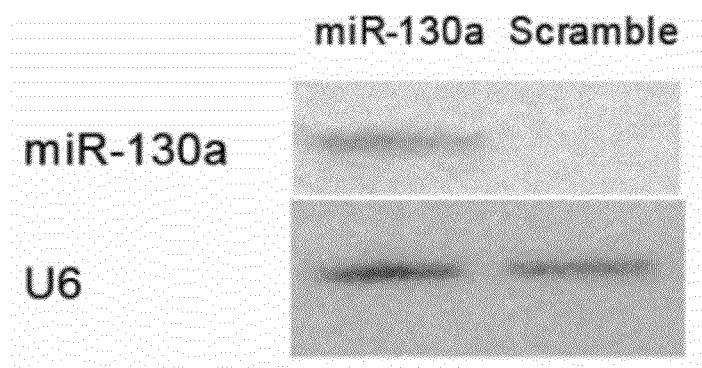
FIG. 7 is a Northern Blot of total RNA obtained from K562 cells transfected with miR-130a precursor and scramble sequences hybridized with the probe for miR-130a. An RNA loading control was performed using U6 hybridization.

We also determined the in vivo consequences of overexpressing miR-130a on MAFB expression. The pre-miR-130a and a negative control were transfected by electroporation into K562 cells, which naturally express MAFB and lack miR-130a. Transfection of the pre-miR-130a, but not the control, resulted in a decrease in the protein levels at 48 hours (FIG. 2C). Northern blotting confirmed successful ectopic expression of miR-130a in K562 cells (FIG. 7).

EXAMPLE 3

MiR-10a Correlates with HOXB Gene Expression

Figure 8:
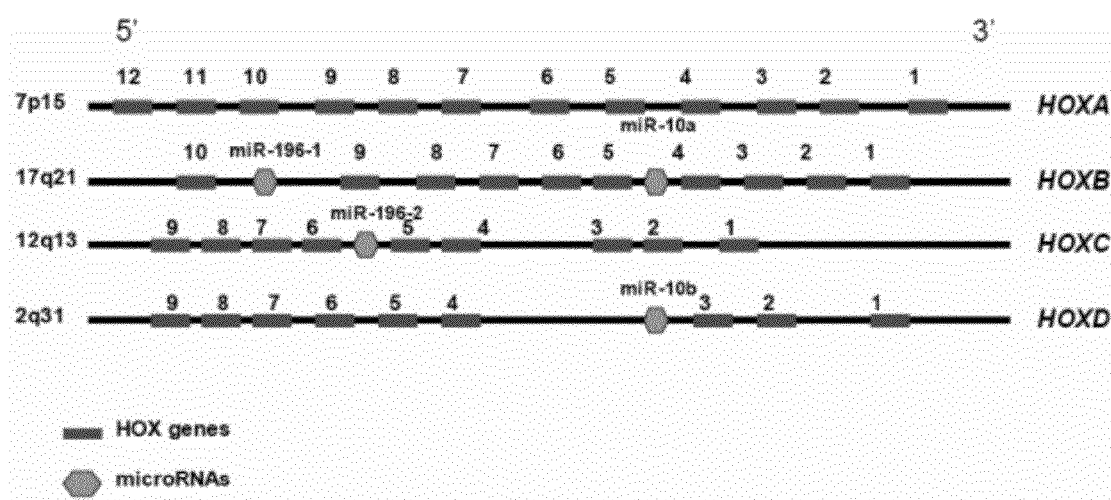
FIG. 8 is a schematic depicting microRNAs that are located in the HOXA, HOXB, HOXC and HOXD gene clusters.

It has been reported that in mouse embryos, miR-10a, miR-10b, and miR-196 are expressed in HOX-like patterns (Mansfield, J. H., et al. (2004) Nature 36, 1079-1083) and closely follow their "host" HOX cluster during evolution (Tanzer, A., et al. (2005) J. Exp. Zool. B Mol. Dev. Evol. 304B, 75-85). These data suggest common regulatory elements across paralog clusters. MiR-10a is located at chromosome 17q21 within the cluster of the HOXB genes (FIG. 8) and miR-10b is located at chromosome 2q31 within the HOXD gene cluster. To determine whether the miR-10a expression pattern correlates with the expression of HOXB genes, we performed RT-PCR for HOXB4 and HOXB5, which are the genes located 5' and 3', respectively, to miR-10a in the HOXB cluster. As shown in FIG. 8, HOXB4 and HOXB5 expression paralleled that of miR-10a, suggesting a common regulatory mechanism.

EXAMPLE 4

MiR-10a Downregulates HOXA1

Figure 3A:
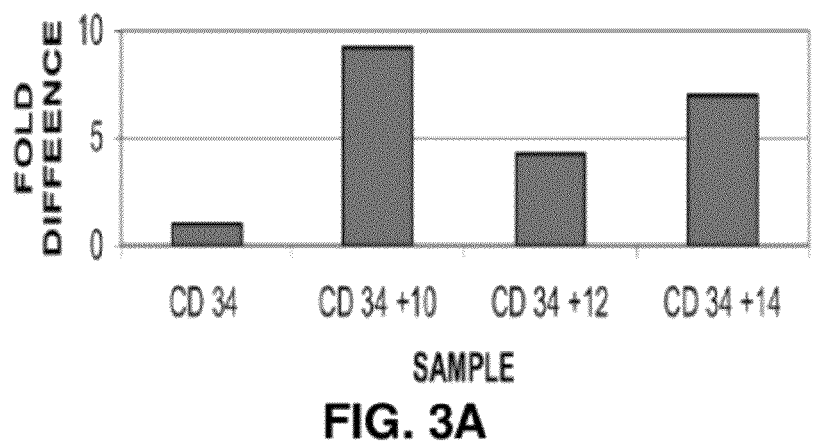
FIGS. 3A-3G demonstrate that MiR-10a downregulates HOXA1 by mediating RNA cleavage.
Figure 3B:
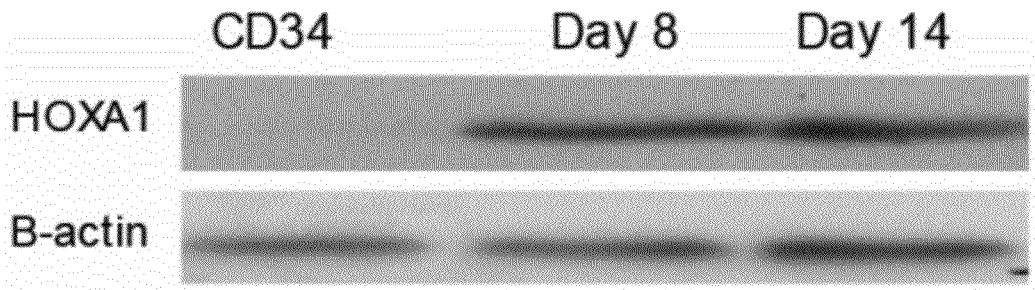
Figure 3C:
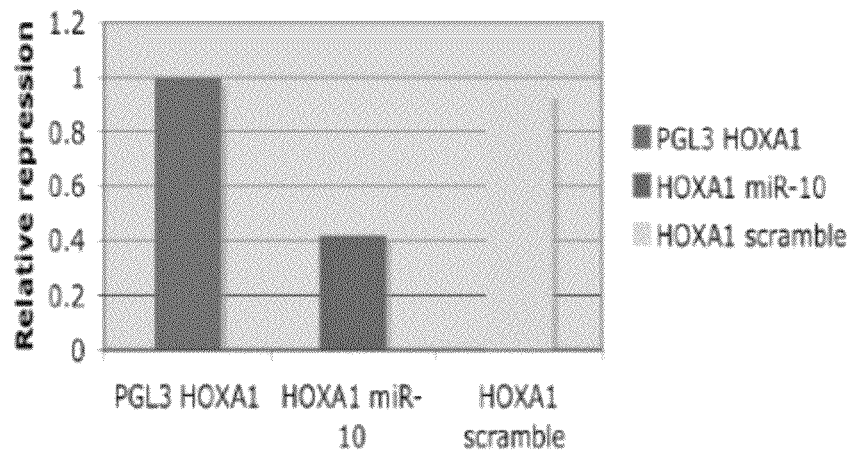
Figure 3D:
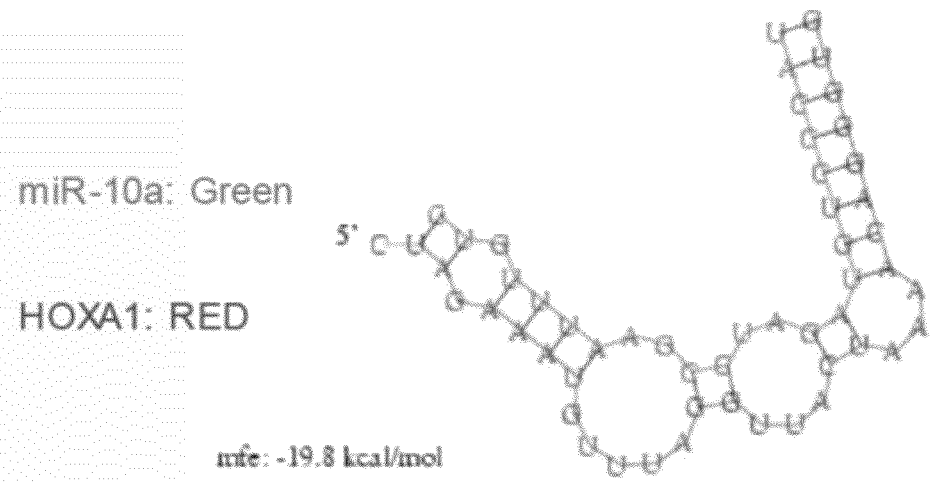
Figure 9A:
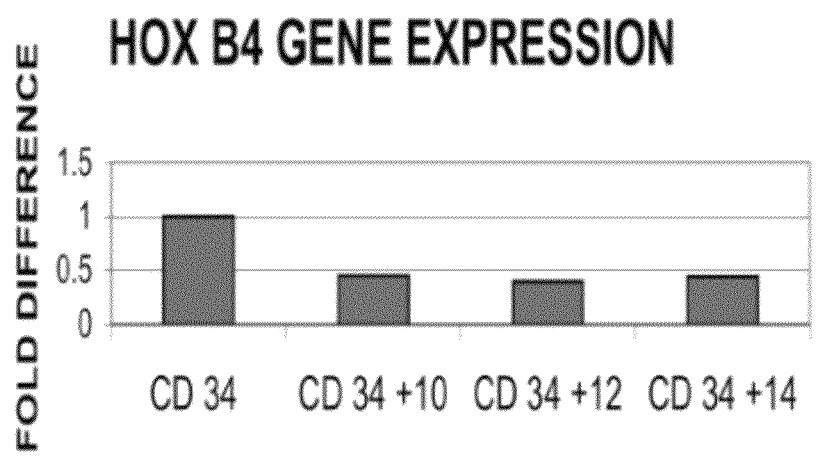
FIG. 9A is a graph depicting HOXB4 gene expression in differentiated megakaryocytes. RT-PCR results for HOXB4 are shown as fold difference in the expression level with respect to CD34+ progenitors at baseline (before culture).
Figure 9B:
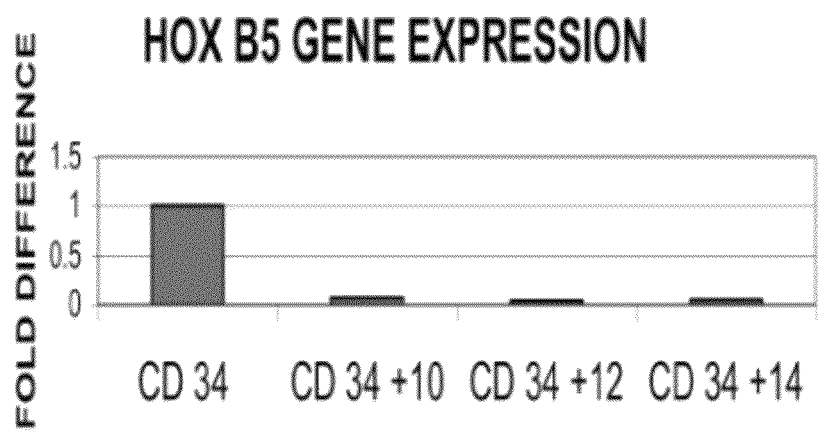
FIG. 9B is a graph depicting HOXB5 gene expression in differentiated megakaryocytes. RT-PCR results for HOXB5 are shown as fold difference in the expression levels with respect to CD34+ progenitors at baseline (before culture).

We determined by miRNA array and Northern blot that miR-10a is sharply downregulated during megakaryocytic differentiation. Interestingly, we found several HOX genes as putative targets for miR-10a (Table 2). We thus investigated whether miR-10a could target a HOX gene. We performed real-time PCR for the predicted HOX targets of miR-10: HOXA1, HOXA3, and HOXD10. After normalization with 18S RNA, we found that HOXA1 mRNA is upregulated 7-fold during megakaryocytic differentiation compared with CD34 progenitors (FIG. 3A; see also FIG. 9). HOXA1 protein levels were also upregulated during megakaryocytic differentiation (FIG. 3B). These results are in sharp contrast with the downregulation of miR-10a in megakaryocytic differentiation, suggesting that miR-10a could be an inhibitor of HOXA1 expression. To demonstrate a direct interaction of miR-10a and the 3' UTR sequences of the HOXA1 gene, we carried out a luciferase reporter assay as described in Material and Methods. When the miRNA precursor miR-10a was introduced in the MEG01 cells along with the reporter plasmid containing the 3' UTR sequence of HOXA1, a 50% reduction in luciferase activity was observed (FIG. 3C). The degree of complementarity between miR-10a and the HOXA1 3' UTR is shown in FIG. 3D, as predicted by PICTAR (www.pictar.bio.nyu.edu).

Figure 3E:
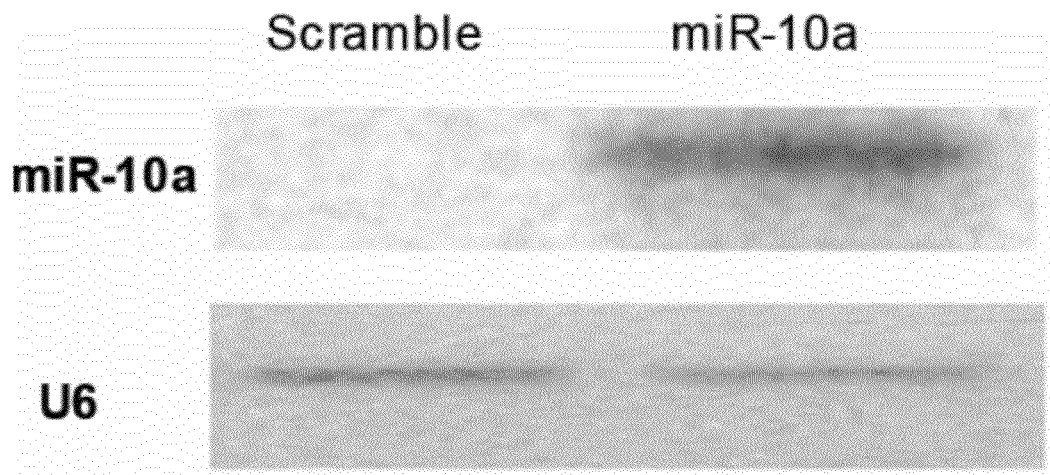
Figure 3F:
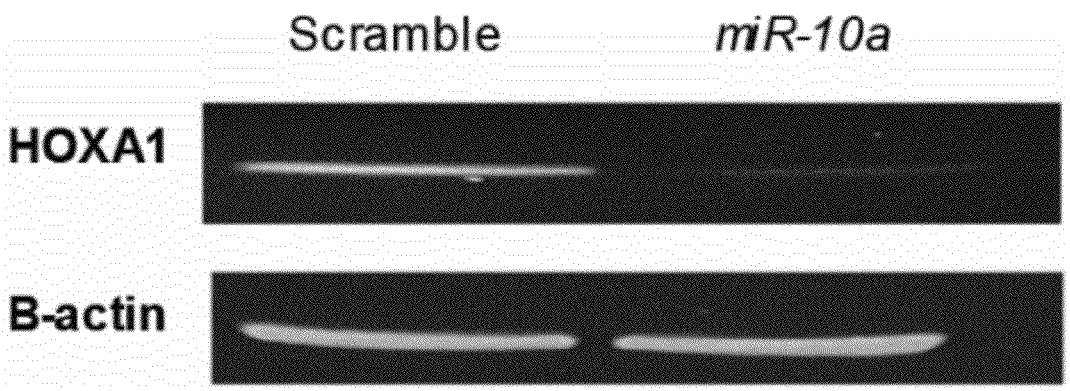
Figure 3G:
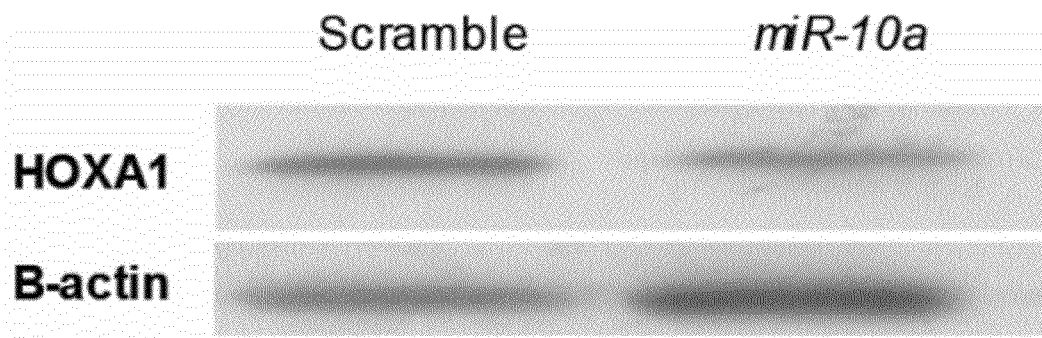
Figure 4A:
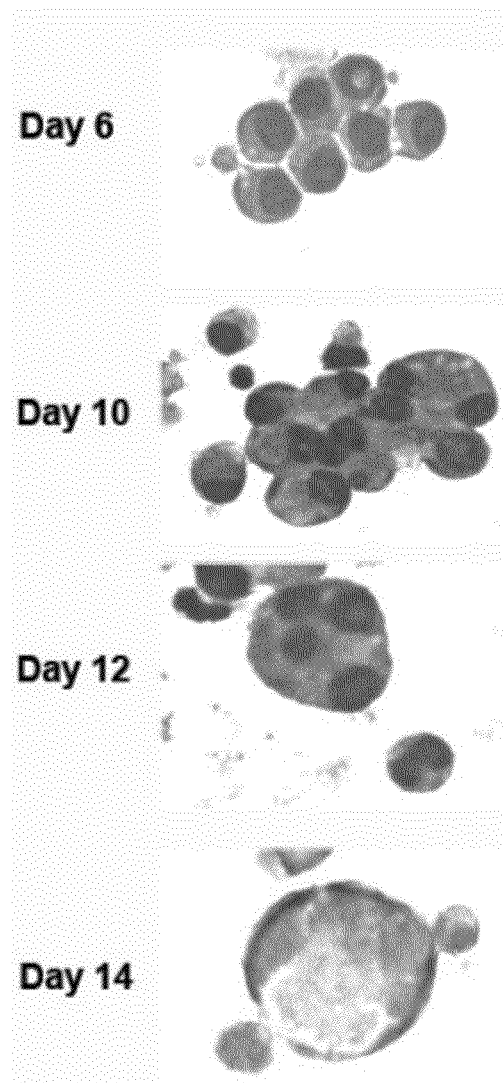
FIGS. 4A and 4B show phenotypic characterization results of in vitro-differentiated CD34$^+$ progenitors.
Figure 4B:
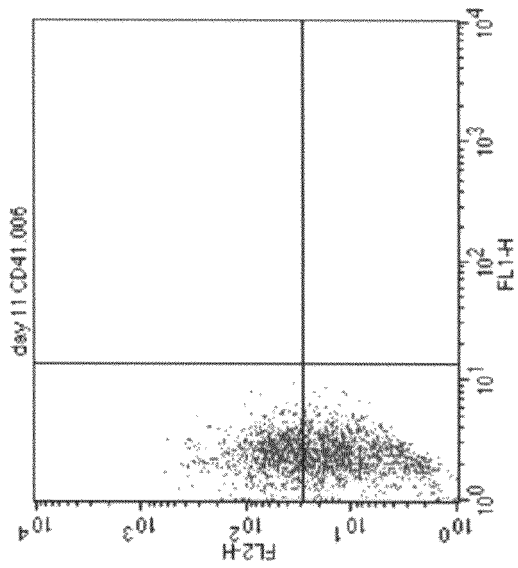
Figure 4B:
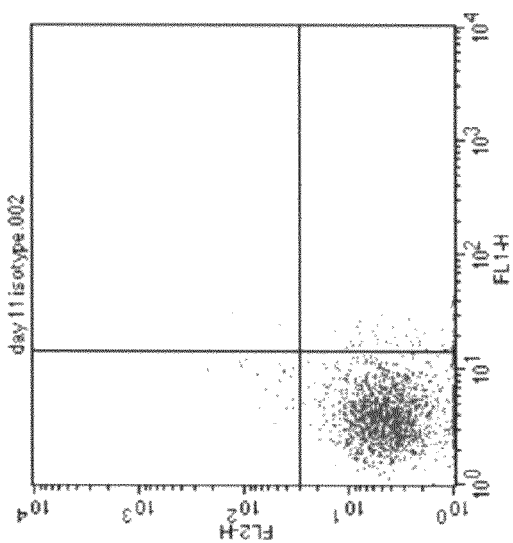
Figure 4B:
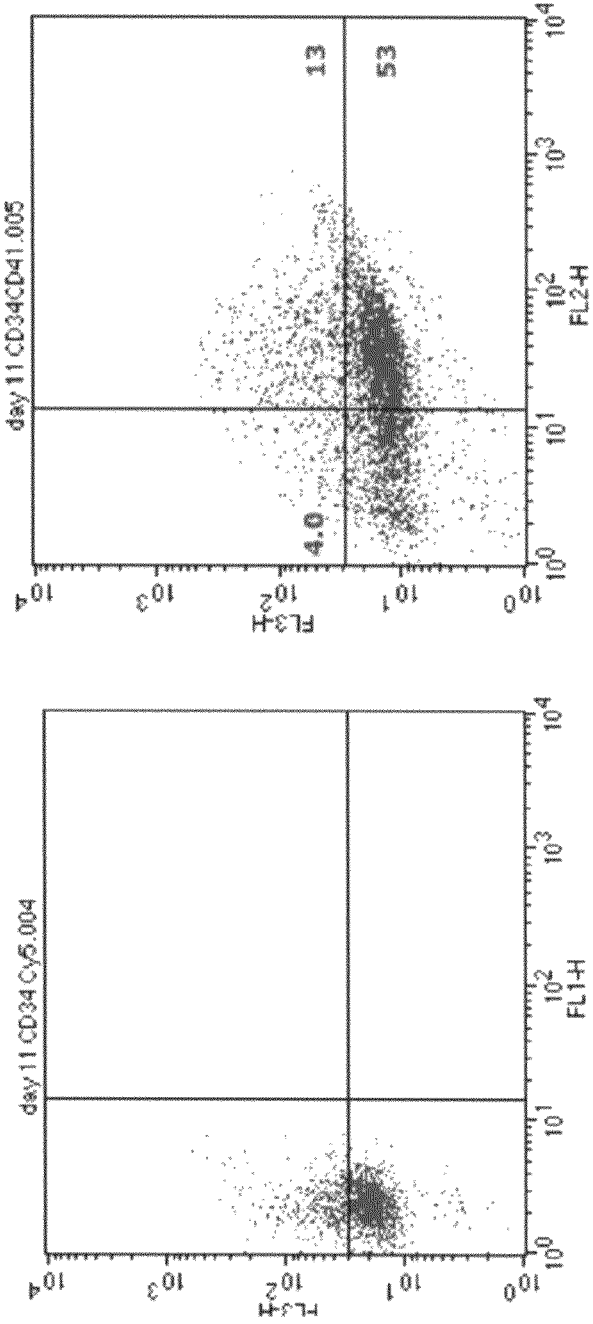
Figure 4B:
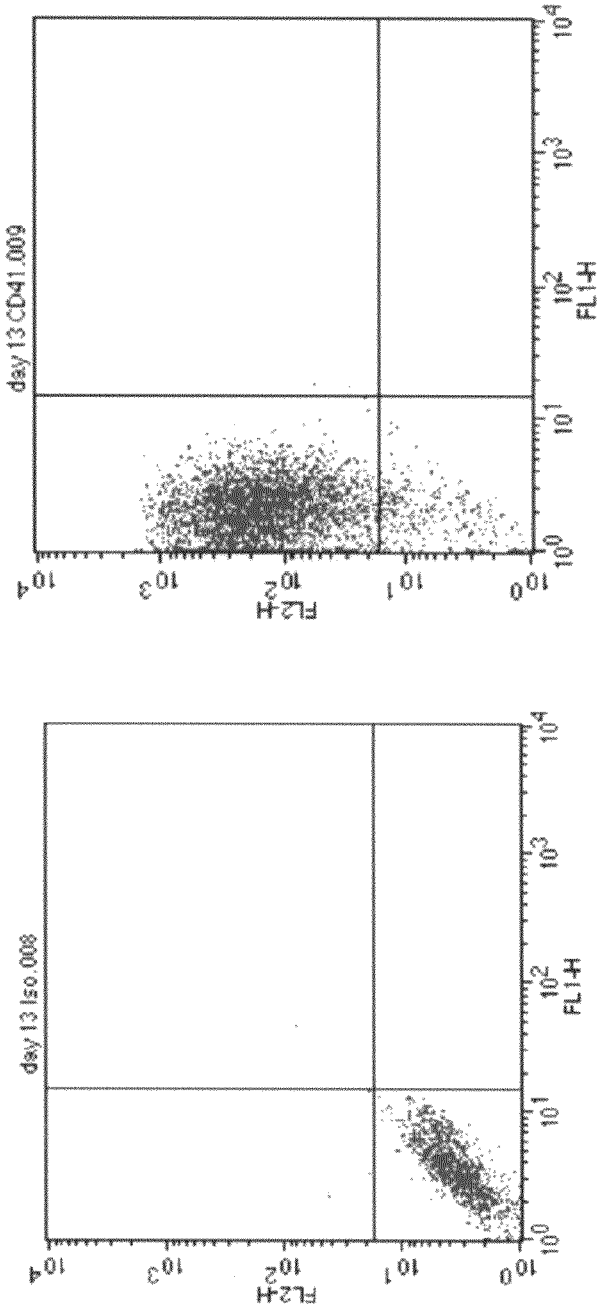
Figure 4B:
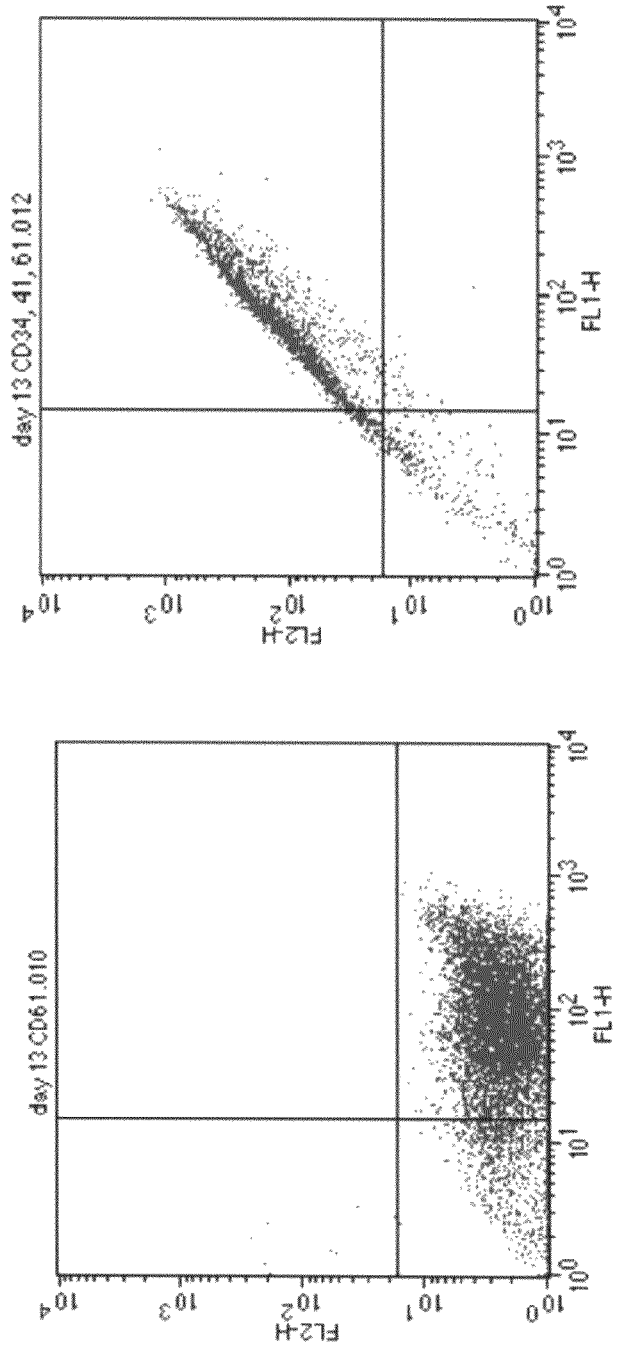
Figure 4B:
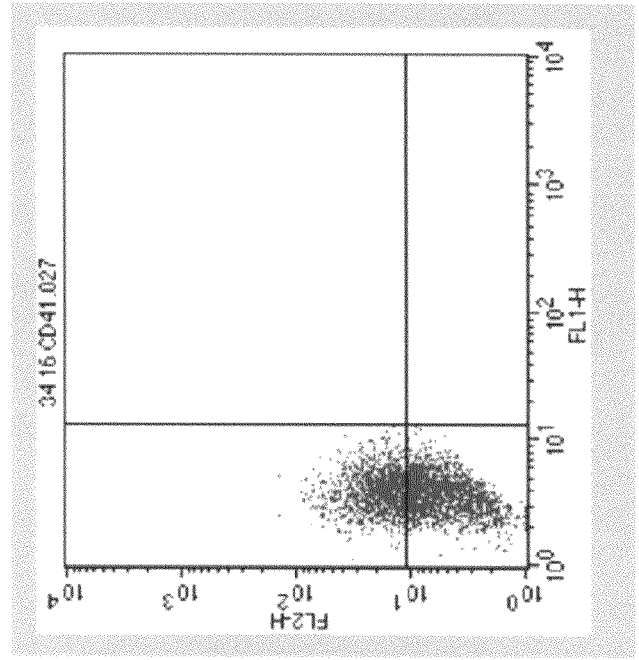
Figure 4B:
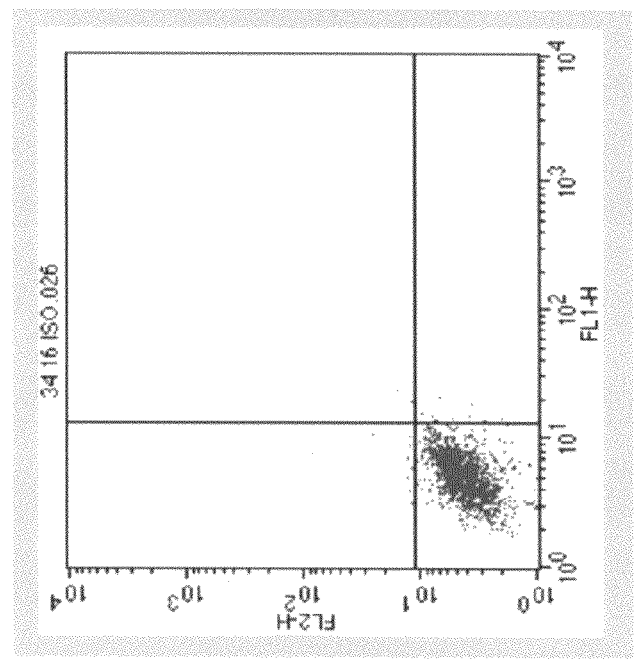
Figure 4B:
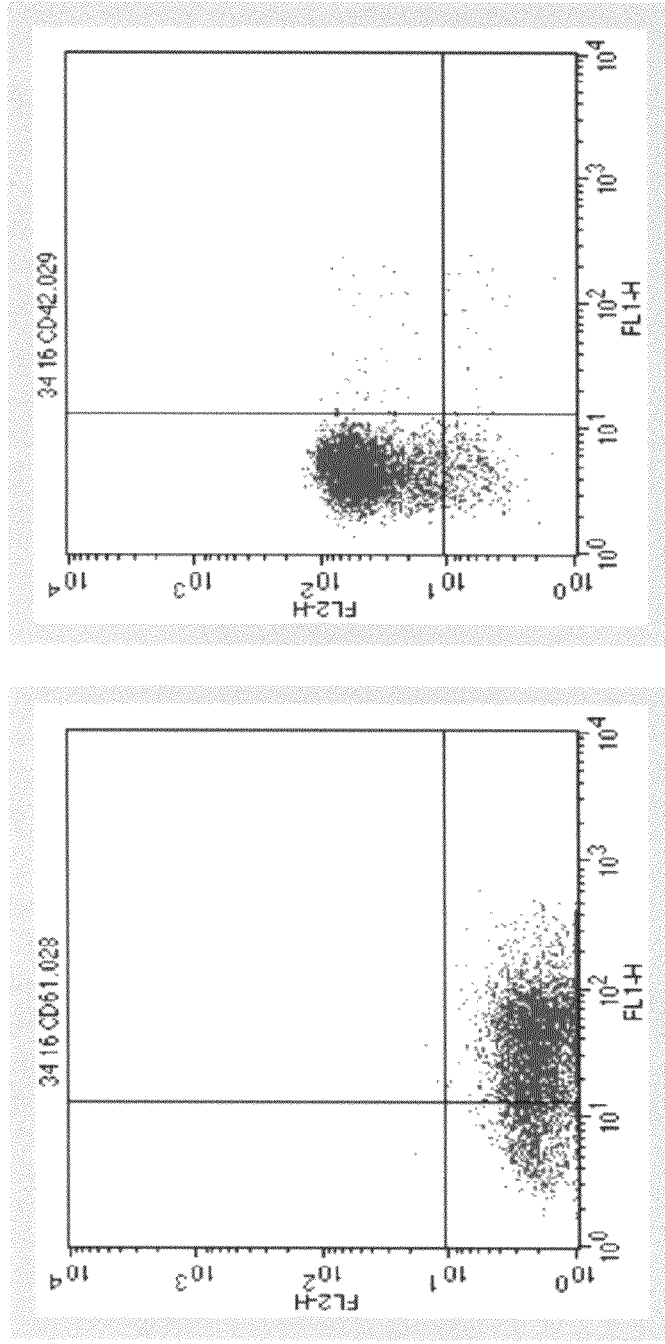

To confirm in vivo these findings, we transfected K562 cells with the pre-miR-10a precursor using nucleoporation and measured HOXA1 mRNA expression by RT-PCR and HOXA1 protein levels by Western blotting. Successful ectopic expression of miR-10a was documented by Northern Blot (FIG. 3E). A significant reduction at the mRNA and protein levels for HOXA1 was found for K562 cells transfected with the miR-10a precursor but not with the negative control (FIGS. 3F and 3G). These data indicate that miR-10a targets HOXA1 in vitro and in vivo.

It has been reported that miR-196 induces cleavage of HOXB8 mRNA, pointing to a posttranscriptional restriction mechanism of HOX gene expression (Yekta, S., et al. (2004) *Science*, 304:594-596). Contrary to the miR-196-HOXB8 interaction, where an almost perfect complementarity exists, the degree of pairing between miR-10a and the human HOXA1 3' UTR is suboptimal (FIG. 4). Although our results indicated target mRNA degradation, further studies are needed to determine whether cleavage or translational repression is the primary mechanism of downregulation of the HOXA1 gene in this system. A previous study using microarray analysis showed that a large number of target mRNA genes are downregulated by miRNA at the level of transcription (Lim, L. P., et al. (2005) *Nature:* 433,769-771). These data raise the question whether target degradation is a consequence of translational repression and subsequent relocalization of the miR-target complexes to cytoplasmic processing bodies or is a primary event (Pillai, R. (2005) *RNA* 11, 1753-1761).

EXAMPLE 5 miRNA Profiling in Acute Megakaryoblastic Leukemia (AMKL) Cell Lines

Figure 10:
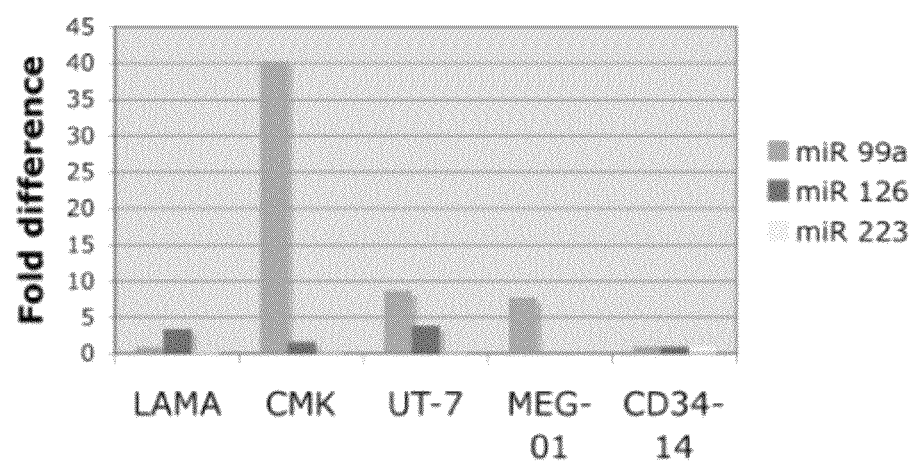
FIG. 10 is a graph depicting microRNA expression in acute megakaryoblastic cell lines by RT-PCR. Results are expressed as fold difference with respect to CD34-differentiated megakaryocytes after normalization with 18S and delta Ct calculations.

After the identification of the microRNA expression profile of CD34+ cells during megakaryocytic differentiation, we then investigated miRNA expression in AMKL cell lines with the goal to identify differentially expressed miRNAs that could have a pathogenic role in megakaryoblastic leukemia. We initially compared miRNA expression in four AMKL cell lines with that of in vitro CD34+-differentiated megakaryocytes. Using significance analysis of microarray (SAM), we identified 10 miRNAs upregulated in AMKL cell lines compared with that of CD34 in vitro-differentiated megakaryocytes (Table 3; see also Table 4). These miRNAs are as follows (in order of the fold increase with respect to differentiated megakaryocytes): miR-101, miR-126, miR-99a, miR-99-prec, miR-106, miR-339, miR-99b, miR-149, miR-33 and miR-135. Results were validated by RT-PCR as shown in FIG. 10. Using PAM, we compared miRNA expression in CD34+ cells with in vitro-differentiated megakaryocytes and AMKL cell lines (FIG. 10). Interestingly, we found five miRNAs involved in the megakaryocytic differentiation signature (miR-101, miR-126, miR-106, miR-20, and miR-135) that were upregulated in the leukemic cell lines (Tables 3, 5 and 6). Whether this profile represents merely a differentiation state of the cells or has a truly pathogenic role remains to be elucidated. Supporting the second hypothesis, miR-106, miR-135, and miR-20 are predicted to target RUNX1, which is one of the genes most commonly associated with leukemia (Nakao, M., et al. (2004) *Oncogene* 125, 709-719). Moreover, mutations of RUNX1 have been described in familial thrombocytopenias with a propensity to develop acute myeloid leukemia (Song, W. J., et al. (1999) *Nat. Genet.* 23, 166-175).

TABLE 3 microRNAs upregulated in acute megakaryoblastic cell lines compared with in vitro-differentiated megakaryocytes.

| microRNA | Chromosomal Location | t test Score | Fold Change | Putative Targets |
|---|---|---|---|---|
| hsa-mir-101 | 1p31.3 | 6.14 | 11.85 | MEIS2, RUNX1, ETS-1, C-MYB, FOS, RARB, NFE2L2 |
| hsa-mir-126 | 9q34 | 4.91 | 11.97 | V-CRK |
| hsa-mir-099a | 21q21 | 3.30 | 6.83 | HOXA1, EIF2C, FOXA1 |
| hsa-mir-099b-prec | 21q21 | 2.85 | 7.59 | NA |
| hsa-mir-106 | xq26.2 | 2.79 | 3.33 | FLT1, SKI, E2F1, NCOA3, PDGFRA, CRK |
| hsa-mir-339 | 7p22 | 2.58 | 3.36 | HOXA1, FLT1, PTP4A1, RAP1B |
| hsa-mir-099b | 19q13 | 2.46 | 4.19 | HOXA1, MYCBP2 |
| hsa-mir-149 | 2q37 | 2.29 | 3.53 | RAP1A, MAFF, PDGFRA, SP1, NFIB |
| hsa-mir-033 | 2q13 | 2.27 | 3.23 | PDGFRA, HIF1A, MEIS2 |
| hsa-mir-135 | 3p21 | 2.12 | 3.97 | SP1, HIF1A, SP3, HNRPA1, HOXA10, RUNX1 |

All the miRNAs have a q value <0.01 (false discovery rate).

The same miRNAs, except miR-339 and miR-149, were found by using PAM to predict a megakaryoblastic leukemia class with no misclassification error.\

The results described herein demonstrate that there is a downregulation of miRNAs during megakaryocytopoiesis. Hypothetically, the downregulation of miRNAs unblocks target genes involved in differentiation. In line with this hypothesis, miRNAs that are sharply downregulated in our system are predicted to target genes with important roles in megakaryocytic differentiation. Thus, we have shown that miR- 130a targets MAFB and miR-10a modulates HOXA1. The fact that we found several differentially expressed miRNAs during differentiation and leukemia that are predicted to target HOXA1 suggests a function for HOXA1 in megakaryocytopoiesis. Loss and gain studies will ultimately be needed to define the role of HOXA1 in this differentiation process. Our findings delineate the expression of miRNAs in megakaryocytic differentiation and suggest a role for miRNA modulation of this lineage by targeting megakaryocytic transcription factors. Furthermore, in megakaryoblastic leukemia cell lines, we have found inverse expression of miRNAs involved in normal megakaryocytic differentiation. These data provide a starting point for future studies of miRNAs in megakaryocytopoiesis and leukemia.

TABLE 4

Signature of megakaryocytic differentiation.

| microRNA | CD34 Expression | Megakaryocytic Expression |
|---|---|---|
| hsa-mir-010a | up | Down |
| hsa-mir-126 | up | Down |
| hsa-mir-130a-prec | up | Down |
| hsa-mir-010b | up | Down |
| hsa-mir-106 | up | Down |
| hsa-mir-130a | up | Down |
| hsa-mir-132 | up | Down |
| hsa-mir-30c | up | Down |
| hsa-mir-143-prec | Down | up |

PAM selected microRNAs with a very low misclassification error.

TABLE 5

Signature of megakaryoblastic leukemia cell lines

| MicroRNA | t test Score | Fold Change | Level of Expression in AML M7 | Putative Targets |
|---|---|---|---|---|
| hsa-mir-101- | 6.14 | 11.85 | up | MEIS2, RUNX1, C-MYB, FOS, RARb, NFE2L2 |
| hsa-mir-126 | 4.91 | 11.97 | up | V-CRK |
| hsa-mir-099a | 3.30 | 6.83 | up | HOXA1, EIF2C, FOXA1 |
| hsa-mir-095 | | | up | SHOX2 |
| hsa-mir-033 | 2.27 | 3.23 | up | PDGFRA, HIF1A, MEIS2 |
| hsa-mir-135 | 2.12 | 3.97 | up | SP1, HIF1A, SP3, HNRPA1, HOXA10, RUNX1 |
| hsa-mir-099b | 2.85 | 7.59 | up | HOXA1, MYCBP2 |
| hsa-mir-339 | 2.58 | 3.36 | up | HOXA1, FLT1, PTP4A1, RAP1B |
| hsa-mir-106 | 2.79 | 3.33 | up | HOXA1, EIF2C, FOXA1 |
| hsa-mir-124a | 2.07 | 2.78 | up | SDFR1, RXRa |
| hsa-mir-155 | | | down | ETS-1 |
| hsa-mir-020 | 2.00 | 3.09 | up | TAL1, SKI, RUNX-1, FLT1, CRK, FOG2, RARB |
| hsa-mir-025 | 1.98 | 4.24 | up | GATA2, |
| hsa-mir-140 | | | down | GATA1 |

AM selected microRNAs. The fold change of miRNA expression is shown alongside t test score (SAM) and putative targets.

Table 6 Three class analysis showing the different regulated microRNAs among the three cell types: CD34$^+$ progenitors, acute megakaryoblastic leukemia cell lines(AMKL) and in vitro-differentiated megakaryocytes.

TABLE 6

| microRNA | Chromosomal Location | CD34$^+$ Score | AML M7 cell lines score | In Vitro-differentiated Megakaryocytes Score |
|---|---|---|---|---|
| hsa-mir-010a | 17q21 | 1.0198 | 0 | −0.3562 |
| hsa-mir-101 | 1p31.3 | 0 | 0.814 | −0.432 |
| hsa-mir-126 | 9q34 | 0.0621 | 0.4882 | −0.4514 |
| hsa-mir-099a | 21q21 | 0 | 0.4685 | −0.2875 |
| hsa-mir-033 | 22q13 | 0 | 0.4258 | −0.2294 |
| hsa-mir-095 | 4p16 | 0 | 0.4142 | −0.3567 |
| hsa-mir-010b | 2q31 | 0.3308 | 0 | 0 |
| hsa-mir-155 | 21q21 | 0 | −0.3217 | 0 |
| hsa-mir-130a | 11q12 | 0.2755 | 0 | 0 |
| hsa-let-7d | 9q22 | 0.263 | −0.274 | 0 |
| hsa-mir-099b-prec | 21q21 | 0 | 0.266 | −0.1078 |
| hsa-mir-135-2-prec | 12q23 | 0 | 0.2279 | −0.2566 |
| hsa-mir-339 | 7p22 | 0 | 0.2456 | −0.1176 |
| hsa-mir-099b | 19q13 | 0 | 0.2275 | −0.1025 |
| hsa-mir-106 | xq26 | 0 | 0.0575 | −0.1891 |
| hsa-let-7c | 21q21 | 0.0289 | −0.1753 | 0 |
| hsa-mir-148 | 7p15 | 0 | −0.1748 | 0 |
| hsa-mir-132-prec | 17p13 | 0.1721 | 0 | 0 |
| hsa-mir-020 | 13q31 | 0 | 0.0374 | −0.1509 |

There are three patterns of miRNA expression among the three different cell types. The first pattern is defined by miRNA highly expressed in CD34$^+$ cells and downregulated in AMKL and differentiated megakaryocytes. miR-10a and miR-130a follow this pattern of expression; however, miR-10a is upregulated in AMKL relative to differentiated megakaryocytes. The second pattern is miRNA that is upregulated in AMKL, downregulated in CD34$^+$ cells and differentiated megakaryocytes and includes the following miRNAs: miR-126, miR-99, miR-101, let 7A, and miR-100. The last two miRNAs are equally expressed in CD34$^+$ and differentiated megakaryocytes, rather than showing a gradual decline in expression, as evidenced by miR-126, miR-99 and miR-101. The last pattern includes miRNA-106 and miRNA-135-2, which are upregulated in CD34$^+$cells and AMKL, but low in differentiated megakaryocytes.

MicroRNAs are a highly conserved class of non-coding RNAs with important regulatory functions in proliferation, apoptosis, development and differentiation. As described herein, to discover novel regulatory pathways during megakaryocytic differentiation, we performed microRNA expression profiling of in vitro-differentiated megakaryocytes derived from CD34$^+$ hematopoietic progenitors. One major finding was downregulation of miR-10a, miR-126, miR-106, miR-10b, miR-17 and miR-20. Without wishing to be bound to any theory, it is believed that the downregulation of microRNAs unblocks target genes involved in differentiation. It was confirmed in vitro and in vivo that miR-130a targets the transcription factor MAFB, which is involved in the activation of the GPIIB promoter, a key protein for platelet physiology. In addition, it was shown that miR-10a expression in differentiated megakaryocytes is inverse to that of HOXA1, and HOXA1 is a direct target of miR-10a. Finally, the microRNA expression of megakaryoblastic leukemic cell lines was compared to that of in vitro-differentiated megakaryocytes and CD34$^+$progenitors. This analysis revealed upregulation of miR-101, miR-126, miR-99a, miR-135, and miR-20 in the cancerous cell line. The data and results described herein delineate the expression of microRNAs during megakaryocytopoiesis and demonstrate a regulatory role of microRNAs in this process by targeting megakaryocytic transcription factors.

The relevant teachings of all publications cited herein that have not explicitly been incorporated by reference, are incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

---

What is claimed is:

1. A method of decreasing expression of a transcription factor gene product from the homeobox gene family (HOXA1) in a subject having a cancer and/or myeloproliferative disorder associated with overexpression of a HOXA1 gene product, comprising administering an effective amount of at least one miR-10a gene product or an isolated variant or biologically-active fragment thereof to the subject sufficient to decrease expression of the HOXA1 gene product in the subject, wherein the cancer and/or myeloproliferative disorder is selected from the group consisting of: acute myeloid leukemia (AML), acute megakaryoblastic leukemia (AMKL), multiple myeloma (MM), and chronic myelogenous leukemia (CML).

2. The method of claim 1, wherein the at least one miR-10a gene product or isolated variant or biologically-active fragment thereof comprises a nucleotide sequence that is complementary to a nucleotide sequence in the HOXA1 gene product.

3. The method of claim 1 wherein the cancer and/or myeloproliferative disorder is acute myeloid leukemia.

4. The method of claim 3, wherein the acute myeloid leukemia is acute megakaryoblastic leukemia.

5. The method of claim 1, wherein the cancer and/or myeloproliferative disorder is multiple myeloma.

6. The method of claim 1, wherein the cancer and/or myeloproliferative disorder is chronic myelogenous leukemia (CML).

7. The method of claim 1, wherein the subject is a human.

* * * * *

UNITED STATES PATENT AND TRADEMARK OFFICE
CERTIFICATE OF CORRECTION

PATENT NO. : 8,486,913 B2
APPLICATION NO. : 13/595204
DATED : July 16, 2013
INVENTOR(S) : Carlo M. Croce, Ramiro Garzon and George A. Calin Page 1 of 1

It is certified that error appears in the above-identified patent and that said Letters Patent is hereby corrected as shown below:

In the Specification

Column 1, Lines 22-26 replace the Government Support Clause with:
--This invention was made with government support under grant numbers P01 CA076259, P01 CA081534, P01 CA016058, and P01 CA016672 awarded by the National Institutes of Health. The government has certain rights in the invention.--

Signed and Sealed this
Fourth Day of August, 2020

Andrei Iancu
*Director of the United States Patent and Trademark Office*